US011202825B2

(12) United States Patent
Bickerton et al.

(10) Patent No.: US 11,202,825 B2
(45) Date of Patent: Dec. 21, 2021

(54) ATTENUATED INFECTIOUS BRONCHITIS VIRUS

(71) Applicant: The Pirbright Institute, Wo

(56) References Cited

OTHER PUBLICATIONS

Phillips et al., Changes in nonstructural protein 3 are associated with attenuation in avian coronavirus infectious bronchitis virus, Virus Genes, 44(1):63-74 (2012).
Shen et al., Emergence of a coronavirus infectious bronchitis virus mutant with a truncated 3b gene: functional characterization of the 3b protein in pathogenesis and replication, Virology, 311(1):16-27 (2003).
Tatusova et al., BLAST 2 Sequences, a new tool for comparing protein and nucleotide sequences, FEMS Microbiol. Lett., 174(2):247-50 (1999).
Ausubel et al., Short Protocols in Molecular Biology, 1999, 4th edition, chapter 18 (BLAST package).
Ausubel et al., Short Protocols in Molecular Biology, 1999, 4th edition, pp. 7-58 to 7-60.
Devereux J et al., A comprehensive set of sequence analysis programs for the VAX, Nucl. Acid Res., 12:387-395 (1984).
Haijema B J et al., "Live, Attenuated Coronavirus Vaccines through the Directed Deletion of Group-Specific Genes Provide Protection against Feline Infectious Peritonitis", Journal of Virology., US, (Apr. 15, 2004), vol. 78, No. 8, doi:10.1128/JVI.78.8.3863-3871. 2004, ISSN 0022-538X, pp. 3863-3871, XP055374651.
Hale and Margham, The Harper Collins Dictionary of Biology, Harper Perennial, NY, 1991.
Larkin et al., "Clustal W and Clustal X version 2.0", Bioinformatics, (2007), vol. 23, pp. 2947-2948.
Remington: the Science and Practice of Pharmacy, p. 1905, 20th ed, Lippincott Williams & Wilkins, pub., 2000.
Rowe R C et al. (editors) The Handbook of Pharmaceutical Excipients, 4.sup.th edit., APhA Publications, 2003.
Xu Y et al., Crystal Structures of two Coronavirus ADP-Ribose-1"-Monophophatases and their complexes with ADP-Ribose: a systematic structural analysis of the Virol ADRP domain, Journal of Virology, Jan. 2009, vol. 83, No. 2, pp. 1083-1092.
Egloff et al., Structural and Functional Basis for ADP-Ribose and Poly(ADP-Ribose) Binding by Viral Macro Domains, J. Virol., Sep. 2006, vol. 80, No. 17, pp. 8493-8502.
Gorbalenya et al., Putative papain-related thiol proteases of positive-strand RNA viruses, FEBS Letters, 10058, Aug. 19, 1991, vol. 288, No. 1-2, pp. 201-205.
Kuri et al., The ADP-ribose-1"-monophosphatase domains of severe acute respiratory syndrome coronavirus and human coronavirus 229E mediate resistance to antiviral interferon responses, J. Gen. Virol., 2011, vol. 92, pp. 1899-1905.
Piotrowski et al., Crystal structures of the X-domains of a Group-1 and a Group-3 coronavirus reveal that ADP-ribose-binding may not be a conserved property, Protein Sci., 2009, pp. 6-16.
Putics et al., ADP-Ribose-1"-Monophosphatase: a conserved coronavirus enzyme that is dispensable for viral replication in tissue culture, J. Virol., Oct. 2005, vol. 79, No. 20, pp. 12721-12731.
Saikatendu et al., Structure Basis of Severe Acute Respiratory Syndrome Coronavirus ADP-Ribose-1"-Phosphate Dephosporylation by a Conserved Domain of nsP3, Structure, Nov. 2005, vol. 12, pp. 1665-1675.
Wojdyla et al., Structure of the X (ADRP) domain of nsp3 from feline conronavirus, Acta Crystallographica Section D, Biological Crystallography, 2009, D65, pp. 1292-1300.
Li et al., Attenuation of chicken kidney-type infectious bronchititis virus with cold adaptation, Chinese Journal of Veterinary Medicine, Mar. 22, 2002, issue 3, pp. 3-7.
Jiao et al., DNA Vaccine of Chicken infectious bronchitis virus s1 gene delivered by attenuated salmonella thyphimurium and its protective efficacy, Chinese Journal of Virology, May 15, 2007. issue 3.

* cited by examiner

Summary of clinical signs, virus detection and isolation on day 4 post-infection

| Virus | Rales % of birds with rales | Snicking average number of snicks/minute/bird | Rales | Wheezing | Ciliary activity 4 = 100%, 0 = 0% | Virus presence: RT-PCR (nsp 10) | | | | Replicating virus: RT-PCR for sgmRNA | | | | Virus re-isolated from trachea |
|---|---|---|---|---|---|---|---|---|---|---|---|---|---|---|
| | | | | | | Trachea | Eyelid | Beak | | Eyelid | Beak | Trachea | | |
| mock | 0 | 0.01 | | | 3.9 | N | N | N | | N | N | N/A | N |
| | | | | | 3.7 | N | N | N | | N | N | N/A | N |
| | | | | | 4 | N | N | N | | N | N | N/A | N |
| M41-K-A-ADRP | 11.1 | 0.19 | Y | | 3.8 | Y | Y | Y | | Y | Y | N/A | Y |
| | | | | | 3.4 | Y | Y | Y | | Y | - | N/A | Y |
| | | | | | 2.5 | Y | Y | Y | | Y | Y | N/A | Y |
| M41-K-S-ADRP | 0 | 0.1 | | | 3.6 | Y | Y | Y | | N | Y | N/A | Y |
| | | | | | 2.9 | Y | N | Y | | Y | Y | N/A | Y |
| | | | | | 3.7 | Y | N | Y | | Y | Y | N/A | Y |
| M41-K-del-3ab | 0 | 0.15 | | Y | 3 | Y | Y | Y | | N | Y | N/A | N |
| | | | | | 3.8 | N | N | Y | | N | N | N/A | N |
| | | | | | 4 | N | Y | Y | | N | Y | N/A | N |
| M41-K | 30.8 | 0.54 | | Y | 0 | Y | Y | Y | | Y | Y | N/A | N |
| | | | | | 2.6 | Y | Y | Y | | Y | - | N/A | Y |
| | | | | | 2.7 | Y | Y | Y | | Y | Y | N/A | Y |

FIGURE 6

Summary of clinical signs, virus detection and isolation on day 6 post-infection

| Virus | Rales % of birds with rales | Snicking average number of snicks/minute/bird | Rales | Wheezing | Ciliary activity 4=100%, 0=0% | Virus presence: RT-PCR (nsp 10) | | | Replicating virus: RT-PCR for sgmRNA | | | Virus re-isolated from trachea |
|---|---|---|---|---|---|---|---|---|---|---|---|---|
| | | | | | | Trachea | Eyelid | Beak | Eyelid | Beak | Trachea | |
| mock | 0 | 0.08 | | | 4 | N | N | N | N | N | N/A | N |
| | | | | | 3.9 | N | N | N | N | N | N/A | N |
| | | | | | 4 | N | N | N | N | N | N/A | |
| M41-K-A-ADRP | 0 | 0.22 | | Y | 3.9 | N | Y | Y | Y | Y | N/A | N |
| | | | | | 3.6 | N | Y | Y | Y | Y | N/A | N |
| | | | | | 3.1 | N | Y | Y | Y | N | N/A | N |
| M41-K-S-ADRP | 11.1 | 0.31 | Y | Y | 2 | Y | Y | Y | Y | Y | N/A | Y |
| | | | Y | | 2.7 | Y | Y | Y | Y | Y | N/A | |
| | | | | | 0.1 | Y | Y | N | N | Y | N/A | N |
| M41-K-del-3ab | 0 | 0 | | | 3.8 | N | Y | N | N | Y | N/A | N |
| | | | | | 3.9 | Y | N | N | Y | N | N/A | Y |
| | | | | | 3.3 | Y | N | N | N | N | N/A | Y |
| M41-K | 30 | 0.57 | Y | | 2.3 | Y | Y | Y | Y | N | N/A | N |
| | | | Y | | 0 | Y | N | Y | Y | N | N/A | |
| | | | | | 0.9 | Y | Y | Y | Y | Y | N/A | |

ATTENUATED INFECTIOUS BRONCHITIS VIRUS

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "53150_Seqlisting.txt", which was created on Jul. 18, 2018 and is 58,657 bytes in size. The subject matter of the Sequence Listing is incorporated herein in its entirety by reference.

FIELD OF THE INVENTION

The present invention relates to an attenuated coronavirus comprising a mutation which causes the virus to have reduced pathogenicity. The present invention also relates to the use of such a coronavirus in a vaccine to prevent and/or treat a disease.

BACKGROUND TO THE INVENTION

Avian infectious bronchitis virus (IBV), the aetiological agent of infectious bronchitis (IB), is a highly infectious and contagious pathogen of domestic fowl that replicates primarily in the respiratory tract but also in epithelial cells of the gut, kidney and oviduct. IBV is a member of the Order Nidovirales, Family Coronaviridae, Subfamily Coronavirinae and Genus *Gammacoronavirus*; genetically very similar coronaviruses cause disease in turkeys, guinea fowl and pheasants.

Clinical signs of IB include sneezing, tracheal rales, nasal discharge and wheezing. Meat-type birds have reduced weight gain, whilst egg-laying birds lay fewer eggs and produce poor quality eggs. The respiratory infection predisposes chickens to secondary bacterial infections which can be fatal in chicks. The virus can also cause permanent damage to the oviduct, especially in chicks, leading to reduced egg production and quality; and kidney, sometimes leading to kidney disease which can be fatal.

IBV has been reported to be responsible for more economic loss to the poultry industry than any other infectious disease. Although live attenuated vaccines and inactivated vaccines are universally used in the control of IBV, the protection gained by use of vaccination can be lost either due to vaccine breakdown or the introduction of a new IBV serotype that is not related to the vaccine used, posing a risk to the poultry industry.

Further, there is a need in the industry to develop vaccines which are suitable for use in ovo, in order to improve the efficiency and cost-effectiveness of vaccination programmes. A major challenge associated with in ovo vaccination is that the virus must be capable of replicating in the presence of maternally-derived antibodies against the virus, without being pathogenic to the embryo. Current IBV vaccines are derived following multiple passage in embryonated eggs, this results in viruses with reduced pathogenicity for chickens, so that they can be used as live attenuated vaccines. However such viruses almost always show an increased virulence to embryos and therefore cannot be used for in ovo vaccination as they cause reduced hatchability. A 70% reduction in hatchability is seen in some cases.

Attenuation following multiple passages in embryonated eggs also suffers from other disadvantages. It is an empirical method, as attenuation of the viruses is random and will differ every time the virus is passaged, so passage of the same virus through a different series of eggs for attenuation purposes will lead to a different set of mutations leading to attenuation. There are also efficacy problems associated with the process: some mutations will affect the replication of the virus and some of the mutations may make the virus too attenuated. Mutations can also occur in the S gene which may also affect immunogenicity so that the desired immune response is affected and the potential vaccine may not protect against the required serotype. In addition there are problems associated with reversion to virulence and stability of vaccines.

It is important that new and safer vaccines are developed for the control of IBV. Thus there is a need for IBV vaccines which are not associated with these issues, in particular vaccines which may be used for in ovo vaccination.

SUMMARY OF ASPECTS OF THE INVENTION

The present inventors have used a reverse genetics approach in order to rationally attenuate IBV. This approach is much more controllable than random attenuation following multiple passages in embryonated eggs because the position of each mutation is known and its effect on the virus, i.e. the reason for attenuation, can be derived.

Using their reverse genetics approach, the present inventors have identified various mutations which cause the virus to have reduced levels of pathogenicity. The levels of pathogenicity may be reduced such that when the virus is administered to an embryonated egg, it is capable of replicating without being pathogenic to the embryo. Such viruses may be suitable for in ovo vaccination, which is a significant advantage over attenuated IBV vaccines produced following multiple passage in embryonated eggs.

Thus in a first aspect, the present invention provides a live, attenuated coronavirus comprising a mutation in non-structural protein nsp-3 and/or deletion of accessory proteins 3a and/or 3b.

The mutation in nsp-3 may be in the adenosine diphosphate-ribose-1'-phosphatase (ADRP) region.

The modified nsp-3 gene may encode a protein comprising one or more amino acid mutations selected from the list of:
  a) Asn (N) to Ala (A) at position 373 in SEQ ID NO: 6; and
  b) Gly (G) to Ser (S) at position 379 in SEQ ID NO: 6.

The modified nsp-3 gene may encode a protein comprising the amino acid mutation Asn (N) to Ala (A) at position 373 in SEQ ID NO: 6.

The modified nsp-3 gene may encode a protein comprising the amino acid mutation Gly (G) to Ser (S) at position 379 in SEQ ID NO: 6.

The modified nsp-3 gene may comprise one or more nucleotide substitutions selected from the list of:
  a) A to G at nucleotide position 1116 and A to C at nucleotide position 1117 compared to the sequence shown as SEQ ID NO: 5; and
  b) G to A at nucleotide position 1138 compared to the sequence shown as SEQ ID NO: 5.

The live attenuated coronavirus may comprise a deletion from nucleotide position 37 to 384 of the sequence shown as SEQ ID NO: 2.

The coronavirus may be an infectious bronchitis virus (IBV).

The coronavirus may be IBV M41.

The coronavirus may comprise an S protein wherein at least part of which is from an IBV serotype other than M41.

For example, the S1 subunit or the entire S protein may be from an IBV serotype other than M41.

The coronavirus according to the first aspect of the invention may have reduced pathogenicity compared to a wild-type coronavirus, such that when the virus is administered to an embryonated egg, it is capable of replicating without being pathogenic to the embryo.

In a second aspect, the present invention provides a modified nsp-3 gene as defined in connection with the first aspect of the invention.

In a third aspect, the present invention provides a protein encoded by a modified nsp-3 gene according to the second aspect of the invention.

In a fourth aspect, the present invention provides a plasmid comprising a modified nsp-3 gene according to the second aspect of the invention or a modified gene 3 with a deletion of accessory protein 3a and/or 3b.

In a fifth aspect, the present invention provides a method for making the coronavirus according to the first aspect of the invention which comprises the following steps:
(i) transfecting a plasmid according to the fourth aspect of the invention into a host cell;
(ii) infecting the host cell with a recombining virus comprising the genome of a coronavirus strain with a nsp-3 gene and/or gene 3;
(iii) allowing homologous recombination to occur between the gene sequences in the plasmid and the corresponding sequences in the recombining virus genome to produce a modified gene; and
(iv) selecting for recombining virus comprising the modified gene.

The recombining virus may be a vaccinia virus.

The method may also include the step:
(v) recovering recombinant coronavirus comprising the modified gene from the DNA from the recombining virus from step (iv).

In a sixth aspect, the present invention provides a cell capable of producing a coronavirus according to the first aspect of the invention.

In a seventh aspect, the present invention provides a vaccine comprising a coronavirus according to the first aspect of the invention and a pharmaceutically acceptable carrier.

In an eighth aspect, the present invention provides a method for treating and/or preventing a disease in a subject which comprises the step of administering a vaccine according to the seventh aspect of the invention to the subject.

Further aspects of the invention provide:
the vaccine according to the seventh aspect of the invention for use in treating and/or preventing a disease in a subject.
use of a coronavirus according to the first aspect of the invention in the manufacture of a vaccine for treating and/or preventing a disease in a subject.

The disease may be infectious bronchitis (IB).

The method of administration of the vaccine may be selected from the group consisting of; eye drop administration, intranasal administration, drinking water administration, post-hatch injection and in ovo injection.

Vaccination may be by in ovo vaccination.

The present invention also provides a method for producing a vaccine according to the seventh aspect of the invention, which comprises the step of infecting a cell according to the sixth aspect of the invention with a coronavirus according to the first aspect of the invention.

DESCRIPTION OF THE FIGURES

FIG. 4A-D—FIG. 4A) Rales;
FIG. 4B) Combined respiratory symptoms (wheezing and rales);
FIG. 4C) Snicking and FIG. 4D) Ciliary activity in birds infected with rIBV M41K-S-ADRP, rIBV M41K-A-ADRP or rIBV M41K-del3ab compared to M41-K (all bar charts are shown as Mock, rIBV M41K-A-ADRP, rIBV M41K-S-ADRP, rIBV M41K-del3ab, M41-K from left to right).
FIG. 5—Summary of clinical signs, virus detection and isolation on day 4 post-infection.
FIG. 6—Summary of clinical signs, virus detection and isolation on day 6 post-infection.
FIG. 7—Growth kinetics of mutant M41K-S-ADRP 4, M41K-S-ADRP 2 (replicates of the S-ADRP mutation) and M41K-A-ADRP compared to wild type M41-K6 and M41-CK EP4 on CK cells
FIG. 8—Growth kinetics of mutant M41K-del3ab 10 and M41K-del3ab 1 compared to wild type M41-CK and M41-K on CK cells

DETAILED DESCRIPTION

Figure 1:
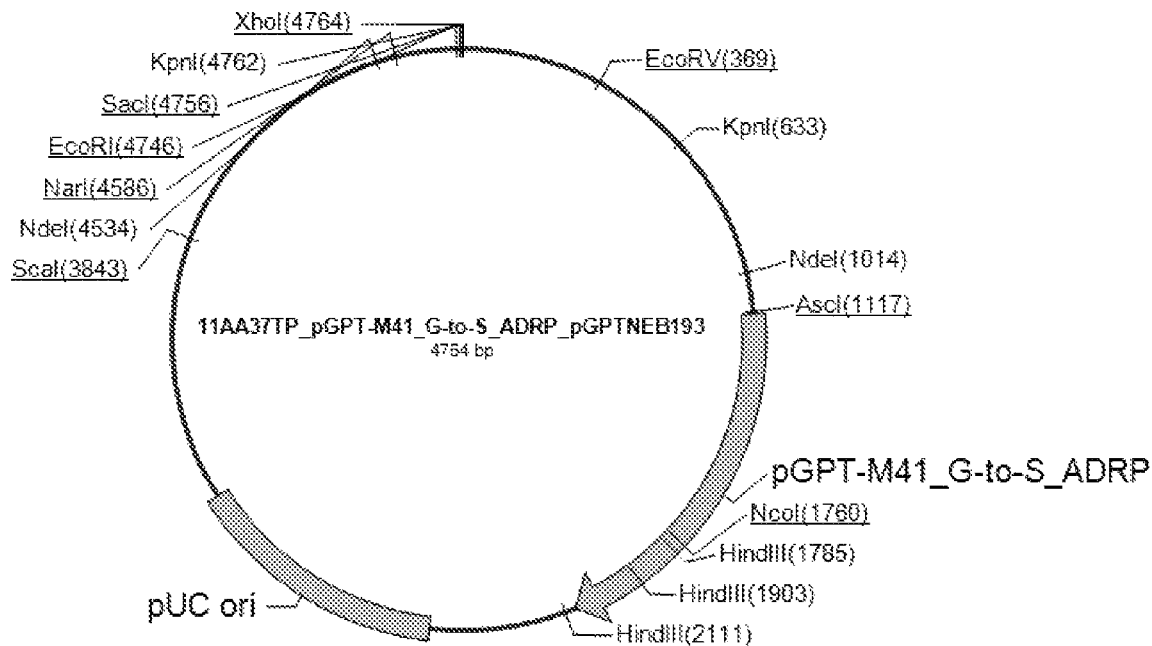
FIG. 1—plasmid used to produce rIBV M41K-S-ADRP.

The present invention provides a mutant coronavirus which has reduced pathogenicity compared to a corresponding wild type coronavirus.

Coronavirus

*Gammacoronavirus* is a genus of animal virus belonging to the family Coronaviridae. Coronaviruses are enveloped viruses with a positive-sense single-stranded RNA genome and a helical symmetry.

The genomic size of coronaviruses ranges from approximately 27 to 32 kilobases, which is the longest size for any known RNA virus.

Coronaviruses primarily infect the upper respiratory or gastrointestinal tract of mammals and birds. Five to six different currently known strains of coronaviruses infect humans. The most publicized human coronavirus, SARS-CoV which causes severe acute respiratory syndrome (SARS), has a unique pathogenesis because it causes both upper and lower respiratory tract infections and can also cause gastroenteritis. Middle East respiratory syndrome coronavirus (MERS-CoV) also causes a lower respiratory tract infection in humans. Coronaviruses are believed to cause a significant percentage of all common colds in human adults.

Coronaviruses also cause a range of diseases in livestock animals and domesticated pets, some of which can be serious and are a threat to the farming industry. Economically significant coronaviruses of livestock animals include infectious bronchitis virus (IBV) which mainly causes respiratory disease in chickens and seriously affects the poultry industry worldwide; porcine coronavirus (transmissible gastroenteritis, TGE) and bovine coronavirus, which both result in diarrhoea in young animals. Feline coronavirus has two forms, feline enteric coronavirus is a pathogen of minor clinical significance, but spontaneous mutation of this virus can result in feline infectious peritonitis (FIP), a disease associated with high mortality.

There are also two types of canine coronavirus (CCoV), one that causes mild gastrointestinal disease and one that has been found to cause respiratory disease.

Mouse hepatitis virus (MHV) is a coronavirus that causes an epidemic murine illness with high mortality, especially among colonies of laboratory mice.

Coronaviruses are divided into four groups, as shown below:

Alpha
  Canine coronavirus (CCoV)
  Feline coronavirus (FeCoV)
  Human coronavirus 229E (HCoV-229E)
  Porcine epidemic diarrhoea virus (PEDV)
  Transmissible gastroenteritis virus (TGEV)
  Human Coronavirus NL63 (NL or New Haven)
Beta
  Bovine coronavirus (BCoV)
  Canine respiratory coronavirus (CRCoV)—Common in SE Asia and Micronesia
  Human coronavirus OC43 (HCoV-OC43)
  Mouse hepatitis virus (MHV)
  Porcine haemagglutinating encephalomyelitis virus (HEV)
  Rat coronavirus (RCV). Rat Coronavirus is quite prevalent in Eastern Australia where, as of March/April 2008, it has been found among native and feral rodent colonies.
  (No common name as of yet) (HCoV-HKU1)
  Severe acute respiratory syndrome coronavirus (SARS-CoV)
  Middle East respiratory syndrome coronavirus (MERS-CoV)
Gamma
  Infectious bronchitis virus (IBV)
  Turkey coronavirus (Bluecomb disease virus)
  Pheasant coronavirus
  Guinea fowl coronavirus
Delta
  Bulbul coronavirus (BuCoV)
  Thrush coronavirus (ThCoV)
  Munia coronavirus (MuCoV)
  Porcine coronavirus (PorCov) HKU15

The recombinant coronavirus of the present invention may be derived from an alphacoronavirus such as TGEV; a betacoronavirus such as MHV; or a gammacoronavirus such as IBV.

As used herein the term "derived from" means that the recombinant coronavirus comprises substantially the same nucleotide sequence as the wild-type coronavirus. For example, the recombinant coronavirus of the present invention may have at least 80%, 85%, 90%, 95%, 98% or 99% identity with the wild type coronavirus sequence.

IBV

Avian infectious bronchitis (IB) is an acute and highly contagious respiratory disease of chickens which causes significant economic losses. The disease is characterized by respiratory signs including gasping, coughing, sneezing, tracheal rales, and nasal discharge. In young chickens, severe respiratory distress may occur. In layers, respiratory distress, nephritis, decrease in egg production, and loss of internal egg quality and egg shell quality are common.

In broilers, coughing and rattling are common clinical signs, rapidly spreading in all the birds of the premises. Morbidity is 100% in non-vaccinated flocks. Mortality varies depending on age, virus strain, and secondary infections but may be up to 60% in non-vaccinated flocks.

The first IBV serotype to be identified was Massachusetts, but in the United States several serotypes, including Arkansas and Delaware, are currently circulating, in addition to the originally identified Massachusetts type.

The IBV strain Beaudette was derived following at least 150 passages in chick embryos. IBV Beaudette is no longer pathogenic for hatched chickens but rapidly kills embryos.

H120 is a commercial live attenuated IBV Massachusetts serotype vaccine strain, attenuated by approximately 120 passages in embryonated chicken eggs. H52 is another Massachusetts vaccine, and represents an earlier and slightly more pathogenic passage virus (passage 52) during the development of H120. Vaccines based on H120 are commonly used.

IB QX is a virulent field isolate of IBV. It is sometimes known as "Chinese QX" as it was originally isolated following outbreaks of disease in the Qingdao region in China in the mid 1990s. Since that time the virus has crept towards Europe. From 2004, severe egg production issues have been identified with a very similar virus in parts of Western Europe, predominantly in the Netherlands, but also reported from Germany, France, Belgium, Denmark and in the UK.

The virus isolated from the Dutch cases was identified by the Dutch Research Institute at Deventer as a new strain that they called D388. The Chinese connection came from further tests which showed that the virus was 99% similar to the Chinese QX viruses. A live attenuated QX-like IBV vaccine strain has now been developed.

IBV is an enveloped virus that replicates in the cell cytoplasm and contains an non-segmented, single-stranded, positive sense RNA genome. IBV has a 27.6 kb RNA genome and like all coronaviruses contains the four structural proteins; spike glycoprotein (S), small membrane protein (E), integral membrane protein (M) and nucleocapsid protein (N) which interacts with the genomic RNA.

The genome is organised in the following manner: 5'UTR-polymerase (replicase) gene-structural protein genes (S-E-M-N)-UTR 3'; where the UTR are untranslated regions (each ~500 nucleotides in IBV).

The lipid envelope contains three membrane proteins: S, M and E. The IBV S protein is a type I glycoprotein which oligomerizes in the endoplasmic reticulum and is assembled into homotrimer inserted in the virion membrane via the transmembrane domain and is associated through non-covalent interactions with the M protein. Following incorporation into coronavirus particles, the S protein is responsible for binding to the target cell receptor and fusion of the viral and cellular membranes. The S glycoprotein consists of four domains: a signal sequence that is cleaved during synthesis; the ectodomain, which is present on the outside of the virion particle; the transmembrane region responsible for anchoring the S protein into the lipid bilayer of the virion particle; and the cytoplasmic tail.

The recombinant coronavirus of the present invention may be derived from an IBV. For example the IBV may be IBV Beaudette, H120, H52, IB QX, D388 or M41.

The IBV may be IBV M41. M41 is a prototypic Massachusetts serotype that was isolated in the USA in 1941. It is an isolate used in many labs throughout the world as a pathogenic lab stain and can be obtained from ATCC (VR-21™). Attenuated variants are also used by several vaccine producers as IBV vaccines against Massachusetts serotypes causing problems in the field. The present inventors chose to use this strain as they had worked for many years on this virus, and because the sequence of the complete virus genome is available. The M41 isolate, M41-CK, used by the present inventors was adapted to grow in primary chick kidney (CK) cells and was therefore deemed amenable for recovery as an infectious virus from a cDNA of the complete genome. It is representative of a pathogenic IBV and therefore can be analysed for mutations that cause either loss or reduction in pathogenicity.

The genome sequence of IBV M41-CK is provided as SEQ ID NO: 1.

IBV M41-CK Sequence

SEQ ID NO: 1

ACTTAAGATAGATATTAATATATATCTATCACACTAGCCTTGCGCTAGATTTCCAACTTAACAAAACGGACTTAAATACCTACAGCTGGTCCT
CATAGGTGTTCCATTGCAGTGCACTTTAGTGCCCTGGATGGCACCTGGCCACCTGTCAGGTTTTTGTTATTAAAATCTTATTGTTGCTGGTAT
CACTGCTTGTTTTGCCGTGTCTCACTTTATACATCCGTTGCTTGGGCTACCTAGTATCCAGCGTCCTACGGGCGCCGTGGCTGGTTCGAGTGC
GAAGAACCTCTGGTTCATCTAGCGGTAGGCGGGTGTGTGGAAGTAGCACTTCAGACGTACCGGTTCTGTTGTGTGAAATACGGGGTCACCTCC
CCCCACATACCTCTAAGGGCTTTTGAGCCTAGCGTTGGGCTACGTTCTCGCATAAGGTCGGCTATACGACGTTTGTAGGGGGTAGTGCCAAAC
AACCCCTGAGGTGACAGGTTCTGGTGGTGTTTAGTGAGCAGACATACAATAGACAGTGACAACATGGCTTCAAGCCTAAAACAGGGAGTATCT
CCCAAACTAAGGGATGTCATTCTTGTATCCAAAGACATTCCTGAACAACTTTGTGACGCTTTGTTTTTCTATACGTCACACAACCCTAAGGAT
TACGCTGATGCTTTTGCAGTTAGGCAGAAGTTTGATCGTAATCTGCAGACTGGGAAACAGTTCAAATTTGAAACTGTGTGTGGTCTCTTCCTC
TTGAAGGGAGTTGACAAAATAACACCTGGCGTCCCAGCAAAAGTCTTAAAAGCCACTTCTAAGTTGGCAGATTTAGAAGACATCTTTGGTGTC
TCTCCCTTTGCAAGAAAATATCGTGAACTTTTGAAGACAGCATGCCAGTGGTCTCTTACTGTAGAAACACTGGATGCTCGTGCACAAACTCTT
GATGAAATTTTTGACCCTACTGAAATACTTTGGCTTCAGGTGGCAGCAAAAATCCAAGTTTCGGCTATGGCGATGCGCAGGCTTGTTGGAGAA
GTAACTGCAAAAGTCATGGATGCTTTGGGCTCAAATATGAGTGCTCTTTTCCAGATTTTTAAACAACAAATAGTCAGAATTTTTCAAAAAGCG
CTGGCTATTTTTGAGAATGTGAGTGAATTACCACAGCGTATTGCAGCACTTAAGATGGCTTTTGCTAAGTGTGCCAAGTCCATTACTGTTGTG
GTTATGGAGAGGACTCTAGTTGTTAGAGAGTTCGCAGGAACTTGTCTTGCAAGCATTAATGGTGCTGTTGCAAAATTCTTTGAAGAACTCCCA
AATGGTTTCATGGGTGCTAAAATTTTCACTACACTTGCCTTCTTTAGGGAGGCTGCAGTGAAAATTGTGGATAACATACCAAATGCACCGAGA
GGCACTAAAGGGTTTGAAGTCGTTGGTAATGCCAAAGGTACACAAGTTGTTGTGCGTGGCATGCGAAATGACTTAACACTGCTTGACCAAAAA
GCTGAAATTCCTGTGGAGTCAGAAGGTTGGTCTGCAATTTTGGGTGGACATCTTTGCTATGTCTTTAAGAGTGGTGATCGCTTTTACGCGGCA
CCTCTTTCAGGAAATTTTGCATTGCATGATGTGCATTGTTGTGAGCGTGTTGTCTGTCTTTCTGATGGTGTAACACCGGAGATAAATGATGGA
CTTATTCTTGCAGCAATCTACTCTTCTTTTAGTGTCGCAGAACTTGTGGCAGCCATTAAAAGGGGTGAACCATTTAAGTTTCTGGGTCATAAA
TTTGTGTATGCAAAGGATGCAGCAGTTTCTTTTACATTAGCGAAGGCTGCTACTATTGCAGATGTTTTGAAGCTGTTTCAATCAGCGCGTGTG
AAAGTAGAAGATGTTTGGTCTTCACTTACTGAAAAGTCTTTTGAATTCTGGAGGCTTGCATATGGAAAAGTGCGTAATCTCGAAGAATTTGTT
AAGACTTGTTTTTGTAAGGCTCAAATGGCGATTGTGATTTTAGCGACAGTGCTTGGAGAGGGCATTTGGCATCTTGTTTCGCAAGTCATCTAT
AAAGTAGGTGGTCTTTTTACTAAAGTTGTTGACTTTTGTGAAAAATATTGGAAAGGTTTTTGTGCACAGTTGAAAAGAGCTAAGCTCATTGTC
ACTGAAACCCTCTGTGTTTTGAAAGGAGTTGCACAGCATTGTTTTCAACTATTGCTGGATGCAATACAGTTTATGTATAAAAGTTTTAAGAAG
TGTGCACTTGGTAGAATCCATGGAGACTTGCTCTTCTGGAAAGGAGGTGTGCACAAAATTATTCAAGAGGGCGATGAAATTTGGTTTGACGCC
ATTGATAGTATTGATGTTGAAGATCTGGGTGTTGTTCAAGAAAAATTGATTGATTTTGATGTTTGTGATAATGTGACACTTCCAGAGAACCAA
CCCGGTCATATGGTTCAAATCGAGGATGACGGAAAGAACTACATGTTCTTCCGCTTCAAAAAGGATGAGAACATTTATTATACACCAATGTCA
CAGCTTGGTGCTATTAATGTGGTTTGCAAAGCAGGCGGTAAAACTGTCACCTTTGGAGAAACTACTGTGCAAGAAATACCACCACCTGATGTT
GTGTTTATTAAGGTTAGCATTGAGTGTTGTGGTGAACCATGGAATACAATCTTCAAAAAGGCTTATAAGGAGCCCATTGAAGTAGAGACAGAC
CTCACAGTTGAACAATTGCTCTCTGTGGTCTATGAGAAAATGTGTGATGATCTCAAGCTGTTTCCGGAGGCTCCAGAACCACCACCATTTGAG
AATGTCACACTTGTTGATAAGAATGGTAAAGATTTGGATTGCATAAAATCATGCCATCTGATCTATCGTGATTATGAGAGCGATGATGACATC
GAGGAAGAAGATGCAGAAGAATGTGACACGGATTCAGGTGATGCTGAGGAGTGTGACACTAATTCAGAATGTGAAGAAGAAGATGAGGATACT
AAAGTGTTGGCTCTTATACAAGACCCGGCAAGTAACAAATATCCTCTGCCTCTTGATGATGATTATAGCGTCTACAATGGATGTATTGTTCAT
AAGGACGCTCTCGATGTTGTGAATTTACCATCTGGTGAAGAAACCTTTGTTGTCAATAACTGCTTTGAAGGGGCTGTTAAAGCTCTTCCGCAG
AAAGTTATTGATGTTCTAGGTGACTGGGGTGAGGCTGTTGATGCGCAAGAACAATTGTGTCAACAAGAATCAACTCGGGTCATATCTGAGAAA
TCAGTTGAGGGTTTTACTGGTAGTTGTGATGCAATGGCTGAACAAGCTATTGTTGAAGAGCAGGAAATAGTACCTGTTGTTGAACAAAGTCAG
GATGTAGTTGTTTTTACACCTGCAGACCTAGAAGTTGTTAAAGAAACAGCAGAAGAGGTTGATGAGTTTATTCTCATTTCTGCTGTCCCTAAA
GAAGAAGTTGTGTCTCAGGAGAAAGAGGAGCCACAGGTTGAGCAAGAGCCTACCCTAGTTGTTAAAGCACAACGTGAGAAGAAGGCTAAAAAG
TTCAAAGTTAAACCAGCTACATGTGAAAAACCCAAATTTTTGGAGTACAAAACATGTGTGGGTGATTTGGCTGTTGTAATTGCCAAAGCATTG
GATGAGTTTAAAGAGTTCTGCATTGTAAACGCTGCAAATGAGCACATGTCGCATGGTGGTGGCGTTGCAAAGGCAATTGCAGACTTTTGTGGA

-continued

```
CCGGACTTTGTTGAATATTGCGCGGACTATGTTAAGAAACATGGTCCACAGCAAAAACTTGTCACACCTTCATTTGTTAAAGGCATTCAATGT
GTGAATAATGTTGTAGGACCTCGCCATGGAGACAGCAACTTGCGTGAGAAGCTTGTTGCTGCTTACAAGAGTGTTCTTGTAGGTGGAGTGGTT
AACTATGTTGTGCCAGTTCTCTCATCAGGGATTTTTGGTGTAGATTTTAAAATATCAATAGATGCTATGCGCGAAGCTTTTAAAGGTTGTGCC
ATACGCGTTCTTTTATTTTCTCTGAGTCAAGAACACATCGATTATTTCGATGCAACTTGTAAGCAGAAGACAATTTATCTTACGGAGGATGGT
GTTAAATACCGCTCTGTTGTTTTAAAACCTGGTGATTCTTTGGGTCAATTTGGACAGGTTTTTGCAAGAAATAAGGTAGTCTTTTCGGCTGAT
GATGTTGAGGATAAAGAAATCCTCTTTATACCCACAACTGACAAGACTATTCTTGAATATTATGGTTTAGATGCGCAAAAGTATGTAACATAT
TTGCAAACGCTTGCGCAGAAATGGGATGTTCAATATAGAGACAATTTTGTTATATTAGAGTGGCGTGACGGAAATTGCTGGATTAGTTCAGCA
ATAGTTCTCCTTCAAGCTGCTAAAATTAGATTTAAAGGTTTTCTTGCAGAAGCATGGGCTAAACTGTTGGGTGGAGATCCTACAGACTTTGTT
GCCTGGTGTTATGCAAGTTGCAATGCTAAAGTAGGTGATTTTTCAGATGCTAATTGGCTTTTGGCCAATTTAGCAGAACATTTTGACGCAGAT
TACACAAATGCACTTCTTAAGAAGTGTGTGTCGTGCAATTGTGGTGTTAAGAGTTATGAACTTAGGGGTCTTGAAGCCTGTATTCAGCCAGTT
CGAGCACCTAATCTTCTACATTTTAAAACGCAATATTCAAATTGCCCAACCTGTGGTGCAAGTAGTACGGATGAAGTAATAGAAGCTTCATTA
CCGTACTTATTGCTTTTTGCTACTGATGGTCCTGCTACAGTTGATTGTGATGAAAATGCTGTAGGGACTGTTGTTTTCATTGGCTCTACTAAT
AGTGGCCATTGTTATACACAAGCCGATGGTAAGGCTTTTGACAATCTTGCTAAGGATAGAAAATTTGGAAGGAAGTCGCCTTACATTACAGCA
ATGTATACACGTTTTTCTCTTAGGAGTGAAAATCCCCTACTTGTTGTTGAACATAGTAAGGGTAAAGCTAAAGTAGTAAAAGAAGATGTTTCT
AACCTTGCTACTAGTTCTAAAGCCAGTTTTGACGATCTTACTGACTTTGAACAGTGGTATGATAGCAACATCTATGAGAGTCTTAAAGTGCAG
GAGACACCTGATAATCTTGATGAATATGTGTCATTTACGACAAAGGAAGATTCTAAGTTGCCACTGACACTTAAAGTTAGAGGTATCAAATCA
GTTGTTGACTTTAGGTCTAAGGATGGTTTTACTTATAAGTTAACACCTGATACTGATGAAAATTCAAAAACACCAGTCTACTACCCAGTCTTG
GATTCTATTAGTCTTAGGGCAATATGGGTTGAAGGCAGTGCTAATTTTGTTGTTGGGCATCCAAATTATTATAGTAAGTCTCTCCGAATTCCC
ACGTTTTGGGAAAATGCCGAGAGCTTTGTTAAAATGGGTTATAAAATTGATGGTGTAACTATGGGCCTTTGGCGTGCAGAACACCTTAATAAA
CCTAATTTGGAGAGAATTTTTAACATTGCTAAGAAAGCTATTGTTGGATCTAGTGTTGTTACTACGCAGTGTGGTAAAATACTAGTTAAAGCA
GCTACATACGTTGCCGATAAAGTAGGTGATGGTGTAGTTCGCAATATTACAGATAGAATTAAGGGTCTTTGTGGATTCACACGTGGCCATTTT
GAAAAGAAAATGTCCCTACAATTTCTAAAGACACTTGTGTTCTTTTTCTTTTATTTCTTAAAGGCTAGTGCTAAGAGTTTAGTTTCTAGCTAT
AAGATTGTGTTATGTAAGGTGGTGTTTGCTACCTTACTTATAGTGTGGTTTATATACACAAGTAATCCAGTAGTGTTTACTGGAATACGTGTG
CTAGACTTCCTATTTGAAGGTTCTTTATGTGGTCCTTATAATGACTACGGTAAAGATTCTTTTGATGTGTTACGCTATTGTGCAGGTGATTTT
ACTTGTCGTGTGTTTACATGATAGAGATTCACTTCATCTGTACAAACATGCTTATAGCGTAGAACAAATTTATAAGGATGCAGCTTCTGGC
ATTAACTTTAATTGGAATTGGCTTTATTTGGTCTTTCTAATATTATTTGTTAAGCCAGTGGCAGGTTTTGTTATTATTTGTTATTGTGTTAAG
TATTTGGTATTGAGTTCAACTGTGTTGCAAACTGGTGTAGGTTTTCTAGATTGGTTTGTAAAAACAGTTTTTACCCATTTTAATTTTATGGGA
GCGGGATTTTATTTCTGGCTCTTTTACAAGATATACGTACAAGTGCATCATATATTGTACTGTAAGGATGTAACATGTGAAGTGTGCAAGAGA
GTTGCACGCAGCAACAGGCAAGAGGTTAGCGTTGTAGTTGGTGGACGCAAGCAAATAGTGCATGTTTACACTAATTCTGGCTATAACTTTTGT
AAGAGACATAATTGGTATTGTAGAAATTGTGATGATTATGGTCACCAAAATACATTTATGTCCCCTGAAGTTGCTGGCGAGCTTTCTGAAAAG
CTTAAGCGCCATGTTAAACCTACAGCATATGCTTACCACGTTGTGTATGAGGCATGCGTGGTTGATGATTTTGTTAATTTAAAATATAAGGCT
GCAATTCCTGGTAAGGATAATGCATCTTCTGCTGTTAAGTGTTTCAGTGTTACAGATTTTTAAAGAAAGCTGTTTTTCTTAAGGAGGCATTG
AAATGTGAACAAATATCTAATGATGGTTTTATAGTGTGTAATACACAGAGTGCGCATGCACTAGAGGAAGCAAAGAATGCAGCCGTCTATTAT
GCGCAATATCTGTGTAAGCCAATACTTATACTTGACCAGGCACTTTATGAGCAATTAATAGTAGAGCCTGTGTCTAAGAGTGTTATAGATAAA
GTGTGTAGCATTTTGTCTAATATAATATCTGTAGATACTGCAGCTTTAAATTATAAGGCAGGCACACTTCGTGATGCTCTGCTTTCTATTACT
AAAGACGAAGAAGCCGTAGATATGGCTATCTTCTGCCACAATCATGAAGTGGAATACACTGGTGACGGTTTTACTAATGTGATACCGTCATAT
GGTATGGACACTGATAAGTTGACACCTCGTGATAGAGGGTTTTTGATAAATGCAGATGCTTCTATTGCTAATTTAAGAGTCAAAAATGCTCCT
CCGGTAGTATGGAAGTTTTCTGATCTTATTAAATTGTCTGACAGTTGCCTTAAATATTTAATTTCAGCTACTGTCAAGTCAGGAGGTCGTTTC
TTTATAACAAAGTCTGGTGCTAAACAAGTTATTTCTTGTCATACCCAGAAACTGTTGGTAGAGAAAAAGGCAGGTGGTGTTATTAATAACACT
TTTAAATGGTTTATGAGTTGTTTTAAATGGCTTTTTGTCTTTTATATACTTTTTACAGCATGTTGTTTGGGTTACTACTATATGGAGATGAAT
```

-continued

```
AAAAGTTTTGTTCACCCCATGTATGATGTAAACTCCACACTGCATGTTGAAGGGTTCAAAGTTATAGACAAAGGTGTTATTAGAGAGATTGTG
TCAGAAGATAATTGTTTCTCTAATAAGTTTGTTAATTTTGACGCCTTTTGGGGTAAATCATATGAAAATAATAAAAACTGTCCAATTGTTACA
GTTGTTATAGATGGTGACGGGACAGTAGCTGTTGGTGTTCCTGGTTTTGTATCATGGGTTATGGATGGTGTTATGTTTGTGCATATGACACAG
ACTGATCGTAGACCTTGGTACATTCCTACCTGGTTTAATAGAGAAATTGTTGGTTACACTCAGGATTCAATTATCACTGAGGGTAGTTTTTAT
ACATCTATAGCATTATTTTCTGCTAGATGTTTATATTTAACAGCCAGCAATACACCTCAATTGTATTGTTTTAATGGCGACAATGATGCACCT
GGAGCCTTACCATTTGGTAGTATTATTCCTCATAGAGTATACTTCCAACCTAATGGTGTTAGGCTTATAGTTCCACAACAAATACTGCATACA
CCCTACATAGTGAAGTTTGTTTCAGACAGCTATTGTAGAGGTAGTGTATGTGAGTATACTAAACCAGGTTACTGTGTGTCACTAGACTCCCAA
TGGGTTTTGTTTAATGATGAATACATTAGTAAACCTGGCGTTTTCTGTGGTTCTACTGTTAGAGAACTTATGTTTAATATGGTTAGTACATTC
TTTACTGGTGTCAACCCTAATATTTATATTCAGCTAGCAACTATGTTTTAATACTAGTTGTTATTGTGTTAATTTTTGCAATGGTTATAAAG
TTTCAAGGTGTTTTTAAAGCTTATGCGACCATTGTGTTTACAATAATGTTAGTTTGGGTTATTAATGCATTTGTTTTGTGTGTACATAGTTAT
AATAGTGTTTTAGCTGTTATATTATTAGTACTCTATTGCTATGCATCATTGGTTACAAGTCGCAATACTGCTATAATAATGCATTGTTGGCTT
GTTTTTACCTTTGGTTTAATAGTACCCACATGGTTGGCTTGTTGCTATCTGGGATTTATTCTTTATATGTACACACCGTTGGTTTTCTGGTGT
TACGGTACTACTAAAAATACTCGTAAGTTGTATGATGGCAACGAGTTTGTTGGTAATTATGACCTTGCTGCGAAGAGCACTTTTGTTATTCGT
GGTACTGAATTTGTTAAGCTTACGAATGAGATAGGTGATAAATTTGAAGCCTATCTTTCTGCGTATGCTAGACTTAAATACTATTCAGGCACT
GGTAGTGAGCAAGATTACTTGCAAGCTTGTCGTGCATGGTTAGCTTATGCTTTGGACCAATATAGAAATAGTGGTGTTGAGGTTGTTTATACC
CCACCGCGTTACTCTATTGGTGTTAGTAGACTACACGCTGGTTTTAAAAAACTAGTTTCTCCTAGTAGTGCTGTTGAGAAGTGCATTGTTAGT
GTCTCTTATAGAGGCAATAATCTTAATGGACTGTGGCTGGGTGATTCTATTTACTGCCCACGCCATGTGTTAGGTAAGTTTAGTGGTGACCAG
TGGGGTGACGTACTAAAACCTTGCTAATAATCATGAGTTTGAAGTTGTAACTCAAAATGGTGTTACTTTGAATGTTGTCAGCAGGCGGCTTAAA
GGAGCAGTTTTAATTTTACAAACTGCAGTTGCCAATGCTGAAACTCCTAAGTATAAGTTTGTTAAAGCTAATTGTGGTGATAGTTTCACTATA
GCTTGTTCTTATGGTGGTACAGTTATAGGACTTTACCCTGTCACTATGCGTTCTAATGGTACTATTAGAGCATCTTTCCTAGCAGGAGCCTGT
GGCTCAGTTGGTTTTAATATAGAAAAGGGTGTAGTTAATTTCTTTTATATGCACCATCTTGAGTTACCTAATGCATTACACACTGGAACTGAC
CTAATGGGTGAGTTTTATGGTGGTTATGTAGATGAAGAGGTTGCGCAAAGAGTGCCACCAGATAATCTAGTTACTAACAATATTGTAGCATGG
CTCTATGCGGCAATTATTAGTGTTAAAGAAAGTAGTTTTTCACAACCTAAATGGTTGGAGAGTACTACTGTTTCTATTGAAGATTACAATAGG
TGGGCTAGTGATAATGGTTTTACTCCATTTTCCACTAGTACTGCTATTACTAAATTAAGTGCTATAACTGGGGTTGATGTTTGTAAACTCCTT
CGCACTATTATGGTAAAAAGTGCTCAATGGGGTAGTGATCCCATTTTAGGACAATATAATTTTGAAGACGAATTGACACCAGAATCTGTATTT
AATCAAGTTGGTGGTGTTAGGTTACAGTCTTCTTTTGTAAGAAAAGCTACATCTTGGTTTTGGAGTAGATGTGTATTAGCTTGCTTCTTGTTT
GTGTTGTGTGCTATTGTCTTATTTACGGCAGTGCCACTTAAGTTTTATGTACATGCAGCTGTTATTTTGTTGATGGCTGTGCTCTTTATTTCT
TTTACTGTTAAACATGTTATGGCATACATGGACACTTTCCTATTGCCTACATTGATTACAGTTATTATTGGAGTTTGTGCTGAAGTCCCTTTC
ATATACAATACTCTAATTAGTCAAGTTGTTATTTTCTTAAGCCAATGGTATGATCCTGTAGTCTTTGATACTATGGTACCATGGATGTTATTG
CCATTAGTGTTGTACACTGCTTTTAAGTGTGTACAAGGCTGCTATATGAATTCTTTCAATACTTCTTTGTTAATGCTGTATCAGTTTATGAAG
TTAGGTTTTGTTATTTACACCTCTTCAAACACTCTTACTGCATATACAGAAGGTAATTGGGAGTTATTCTTTGAGTTGGTTCACACTATTGTG
TTGGCTAATGTTAGTAGTAATTCCTTAATTGGTTTAATTGTTTTTAAGTGTGCTAAGTGGATTTTATATTATTGCAATGCAACATACTTTAAT
AATTATGTGTTAATGGCAGTCATGGTTAATGGCATAGGCTGGCTTTGCACCTGTTACTTTGGATTGTATTGGTGGGTTAATAAAGTTTTTGGT
TTAACCTTAGGTAAATACAATTTTAAAGTTTCAGTAGATCAATATAGGGTATATGTGTTTGCATAAGGTAAATCCACCTAAAACTGTGTGGGAG
GTCTTTACTACAAATATACTTATACAAGGAATTGGAGGCGATCGTGTGTTGCCTATAGCTACAGTGCAATCTAAATTGAGTGATGTAAAGTGT
ACAACTGTTGTTTAATGCAGCTTTTGACTAAGCTTAATGTTGAAGCAAATTCAAAAATGCATGCTTATCTTGTTGAGTTACACAATAAAATC
CTCGCATCTGATGATGTTGGAGAGTGCATGGATAATTTATTGGGTATGCTTATAACACTATTTTGTATAGATTCTACTATTGATTTGGGTGAG
TATTGTGATGATATACTTAAGAGGTCAACTGTATTACAATCGGTTACTCAAGAGTTTTCGCACATACCCTCGTATGCTGAATATGAAAGAGCT
AAGAGTATTTATGAAAAGGTTTTAGCCGATTCTAAAAATGGTGGTGTAACACAGCAAGAGCTTGCTGCATATCGTAAAGCTGCCAATATTGCA
AAGTCAGTTTTTGATAGAGACTTGGCTGTTCAAAAGAAGTTAGATAGCATGGCAGAACGTGCTATGACAACAATGTATAAAGAGGCGCGTGTA
ACTGATAGAAGAGCAAAATTAGTTTCATCATTACATGCACTACTTTTTTCAATGCTTAAGAAAATAGATTCTGAGAAGCTTAATGTCTTATTT
```

-continued

```
GACCAGGCGAATAGTGGTGTTGTACCCCTAGCAACTGTTCCAATTGTTTGTAGTAATAAGCTTACCCTTGTTATACCAGACCCAGAGACGTGG
GTCAAGTGTGTGGAGGGTGTGCATGTTACATATTCAACAGTTGTTTGGAATATAGACTGTGTTACTGATGCCGATGGCACAGAGTTACACCCC
ACTTCTACAGGTAGTGGATTGACTTACTGTATAAGTGGTGATAATATAGCATGGCCTTTAAAGGTTAACTTGACTAGGAATGGGCATAATAAG
GTTGATGTTGCCTTGCAAAATAATGAGCTTATGCCTCACGGTGTAAAGACAAAGGCTTGCGTAGCAGGTGTAGATCAAGCACATTGTAGCGTT
GAGTCTAAATGTTATTATACAAGTATTAGTGGCAGTTCAGTTGTAGCTGCTATTACCTCTTCAAATCCTAATCTGAAAGTAGCCTCTTTTTTG
AATGAGGCAGGTAATCAGATTTATGTAGACTTAGACCCACCATGTAAATTTGGTATGAAAGTGGGTGATAAGGTTGAAGTTGTTTACCTGTAT
TTTATAAAAAATACGAGGTCTATTGTAAGAGGTATGGTACTTGGTGCTATATCTAATGTTGTTGTGTTACAATCTAAAGGTCATGAGACAGAG
GAAGTGGATGCTGTAGGCATTCTCTCACTTTGTTCTTTTGCAGTAGATCCTGCGGATACATATTGTAAATATGTGGCAGCAGGTAATCAACCT
TTAGGTAACTGTGTTAAAATGTTGACAGTACATAATGGTAGTGGTTTTGCAATAACATCAAAGCCAAGTCCAACTCCGGATCAGGATTCTTAT
GGAGGAGCTTCTGTGTGTCTTTATTGTAGAGCACATATAGCACACCCTGGCGGAGCAGGAAATTTAGATGGACGCTGTCAATTTAAAGGTTCT
TTTGTGCAAATACCTACTACGGAGAAAGATCCTGTTGGATTCTGTCTACGTAACAAGGTTTGCACTGTTTGTCAGTGTTGGATTGGTTATGGA
TGTCAGTGTGATTCACTTAGACAACCTAAACCTTCTGTTCAGTCAGTTGCTGTTGCATCTGGTTTTGATAAGAATTATTTAAACGGGTACGGG
GTAGCAGTGAGGCTCGGCTGATACCCCTAGCTAATGGATGTGACCCCGATGTTGTAAAGCGAGCCTTTGATGTTTGTAATAAGGAATCAGCCG
GTATGTTTCAAAATTTGAAGCGTAACTGTGCACGATTCCAAGAAGTACGTGATACTGAAGATGGAAATCTTGAGTATTGTGATTCTTATTTTG
TGGTTAAACAAACCACTCCTAGTAATTATGAACATGAGAAAGCTTGTTATGAAGACTTAAAGTCAGAAGTAACAGCTGATCATGATTTCTTTG
TGTTCAATAAGAACATTTATAATATTAGTAGGCAGAGGCTTACTAAGTATACATGATGGATTTTGCTATGCTTTGCGGCACTTTGACCCAA
AGGATTGCGAAGTTCTTAAAGAAATACTTGTCACTTATGGTTGTATAGAAGATTATCACCCTAAGTGGTTTGAAGAGAATAAGGATTGGTACG
ACCCAATAGAAAACCCTAAATATTATGCCATGTTGGCTAAAATGGGACCTATTGTACGACGTGCTTTATTGAATGCTATTGAGTTCGGAAACC
TCATGGTTGAAAAGGTTATGTTGGTGTTATTACACTTGATAACCAAGATCTTAATGGCAAATTTTATGATTTTGGTGATTTTCAGAAGACAG
CGCCTGGTGCTGGTGTTCCTGTTTTTGATACGTATTATTCTTACATGATGCCCATCATAGCCATGACTGATGCGTTGGCACCTGAGAGGTATT
TTGAATATGATGTGCATAAGGGTTATAAATCTTATGATCTCCTCAAGTATGATTATACTGAGGAGAAACAAGATTTGTTTCAGAAGTACTTTA
AGTATTGGGATCAAGAGTATCACCCTAACTGTCGCGACTGTAGTGATGACAGGTGTTTGATACATTGTGCAAACTTCAACATCTTGTTTTCTA
CACTTGTACCGCAGACTTCTTTCGGTAATTTGTGTAGAAAGGTTTTTGTTGATGGTGTACCATTTATAGCTACTTGTGGCTATCATTCTAAGG
AACTTGGTGTTATTATGAATCAAGATAACACCATGTCATTTTCAAAAATGGGTTTGAGTCAACTCATGCAGTTTGTTGGAGATCCTGCCTTGT
TAGTGGGACATCCAATAAATTAGTGGATCTTAGAACGTCTTGTTTTAGTGTTTGTGCTTTAGCGTCTGGTATTACTCATCAAACGGTAAAAC
CAGGTCACTTTAACAAGGATTTCTACGATTTTGCAGAGAAGGCTGGTATGTTTAAGGAAGGTTCTTCTATACCACTTAAACATTTCTTCTACC
CACAGACTGGTAATGCTGCTATAAACGATTATGATTATTATCGTTATAACAGGCCTACCATGTTTGATATACGTCAACTTTTATTTTGTTTAG
AAGTGACTTCTAAATATTTTGAATGTTATGAAGGCGGCTGTATACCAGCAAGCCAAGTTGTAGTTAACAATTTAGATAAGAGTGCAGGTTATC
CGTTCAATAAGTTTGGAAAGGCCCGTCTCTATTATGAAATGAGTCTAGAGGAGCAGGACCAACTCTTTGAGAGTACAAAGAAGAACGTCCTGC
CTACTATAACTCAGATGAATTTAAAATATGCCATATCCGCGAAAAATAGAGCGCGTACAGTGGCAGGTGTGTCTATCCTTTCTACTATGACTA
ATAGGCAGTTTCATCAGAAGATTCTTAAGTCTATAGTCAACACTAGAAACGCTCCTGTAGTTATTGGAACAACCAAGTTTTATGGCGGTTGGG
ATAACATGTTGAGAAACCTTATTCAGGGTGTTGAAGACCCGATTCTTATGGGTTGGGATTATCCAAAGTGTGATAGAGCAATGCCTAATTTGT
TGCGTATAGCAGCATCTTTAGTACTCGCTCGTAAACACACTAATTGTTGTACTTGGTCTGAACGCGTTTATAGGTTGTATAATGAATGCGCTC
AGGTTTTATCTGAAACTGTCTTAGCTACAGGTGGTATATATGTGAAACCTGGTGGTACTAGCAGTGGAGATGCTACTACTGCTTATGCAAACA
GTGTTTTCAACATAATACAAGCCACATCTGCTAATGTTGCGCGTCTTTTGAGTGTTATAACGCGTGATATTGTATATGATGACATTAAGAGCT
TGCAGTATGAATTGTACCAGCAGGTTTATAGGCGAGTCAATTTTGACCCAGCATTTGTTGAAAAGTTTTATTCTTATTGTGTAAGAATTTCT
CATTGATGATCTTGTCTGACGACGGTGTTGTTTGTTATAACAACACATTAGCCAAACAAGGTCTTGTAGCAGATATTTCTGGTTTTAGAGAAG
TTCTCTACTATCAGAACAATGTTTTTATGGCTGATTCTAAATGTTGGGTTGAACCAGATTTAGAAAAAGGCCCACATGAATTTTGTTCACAGC
ACACAATGTTAGTGGAGGTTGATGGTGAGCCTAGATACTTGCCATATCCAGACCCATCACGTATTTTGTGTGCATGTGTTTTTGTAGATGATT
TGGATAAGACAGAATCTGTGGCTGTTATGGAGCGTTATATCGCTCTTGCCATAGATGCGTACCCACTAGTACATCATGAAAATGAGGAGTACA
```

-continued

```
AGAAGGTATTCTTTGTGCTTCTTTCATACATCAGAAAACTCTATCAAGAGCTTTCTCAGAATATGCTTATGGACTACTCTTTTGTAATGGATA
TAGATAAGGGTAGTAAATTTTGGGAACAGGAGTTCTATGAAAATATGTATAGAGCCCCTACAACATTACAGTCTTGTGGCGTTTGTGTAGTGT
GTAATAGTCAAACTATATTGCGCTGTGGTAATTGTATTCGCAAACCATTTTTGTGTTGTAAGTGTTGCTATGACCATGTCATGCACACAGACC
ACAAAAATGTTTTGTCTATAAATCCTTACATTTGCTCACAGCCAGGTTGTGGTGAAGCAGATGTTACTAAATTGTACCTCGGAGGTATGTCAT
ACTTCTGCGGTAATCATAAACCAAAGTTATCAATACCGTTAGTATCTAATGGTACAGTGTTTGGAATTTACAGGGCTAATTGTGCAGGTAGCG
AAAATGTTGATGATTTTAATCAACTAGCTACTACTAATTGGTCTACTGTGGAACCTTATATTTTGGCAAATCGTTGTGTAGATTCGTTGAGAC
GCTTTGCTGCAGAGACAGTAAAAGCTACAGAAGAATTACATAAGCAACAATTTGCTAGTGCAGAAGTGAGAGAAGTACTCTCAGATCGTGAAT
TGATTCTGTCTTGGGAGCCAGGTAAAACCAGGCCTCCATTGAATAGAAATTATGTTTTCACTGGCTTTCACTTTACTAGAACTAGTAAAGTTC
AGCTCGGTGATTTTACATTTGAAAAAGGTGAAGGTAAGGACGTTGTCTATTATCGAGCGACGTCTACTGCTAAATTGTCTGTTGGAGACATTT
TTGTTTTAACCTCACACAATGTTGTTTCTCTTATAGCGCCAACGTTGTGTCCTCAGCAAACCTTTTCTAGGTTTGTGAATTTAAGACCTAATG
TGATGGTACCTGCGTGTTTTGTAAATAACATTCCATTGTACCATTTAGTAGGCAAGCAGAAGCGTACTACAGTACAAGGCCCTCCTGGCAGTG
GTAAATCCCATTTTGCTATAGGATTGGCGGCTTACTTTAGTAACGCCCGTGTCGTTTTTACTGCATGCTCTCATGCAGCTGTTGATGCTTTAT
GTGAAAAAGCTTTTAAGTTTCTTAAAGTAGATGATTGCACTCGTATAGTACCTCAAAGGACTACTATCGATTGCTTCTCTAAGTTTAAAGCTA
ATGACACAGGCAAAAAGTACATTTTTAGTACTATTAATGCCTTGCCAGAAGTTAGTTGTGACATTCTTTTGGTTGACGAGGTTAGTATGTTGA
CCAATTACGAATTGTCTTTTATTAATGGTAAGATAAACTATCAATATGTTGTGTATGTAGGTGATCCTGCTCAATTACCGGCGCCTCGTACGT
TGCTTAACGGTTCACTCTCTCCAAAGGATTATAATGTTGTCACAAACCTTATGGTTTGTGTTAAACCTGACATTTTCCTTGCAAAGTGTTACC
GTTGTCCTAAAGAAATTGTAGATACTGTTTCTACTCTTGTATATGATGGAAAGTTTATTGCAAATAACCCGGAATCACGTCAGTGTTTCAAGG
TTATAGTTAATAATGGTAATTCTGATGTAGGACATGAAAGTGGCTCAGCCTACAACATAACTCAATTAGAATTTGTGAAAGATTTTGTCTGTC
GCAATAAGGAATGGCGGGAAGCAACATTCATTTCACCTTATAATGCTATGAACCAGAGAGCCTACCGTATGCTTGGACTTAATGTTCAGACAG
TAGACTCGTCTCAAGGTTCGGAGTATGATTATGTTATCTTTTGTGTTACTGCAGATTCGCAGCATGCACTGAATATTAACAGATTCAATGTAG
CGCTTACAAGAGCCAAGCGTGGTATACTAGTTGTCATGCGTCAGCGTGATGAACTATATTCAGCTCTTAAGTTTATAGAGCTTGATAGTGTAG
CAAGTCTGCAAGGTACAGGCTTGTTTAAAATTTGCAACAAAGAGTTTAGTGGTGTTCACCCAGCTTATGCAGTCACAACTAAGGCTCTTGCTG
CAACTTATAAAGTTAATGATGAACTTGCTGCACTTGTTAACGTGGAAGCTGGTTCAGAAATAACATATAAACATCTTATTTCTTTGTTAGGGT
TTAAGATGAGTGTTAATGTTGAAGGCTGCCACAACATGTTTATAACACGTGATGAGGCTATCCGCAACGTAAGAGGTTGGGTAGGTTTTGATG
TAGAAGCAACACATGCTTGCGGTACTAACATTGGTACTAACCTGCCTTTCCAAGTAGGTTTCTCTACTGGTGCAGACTTTGTAGTTACGCCTG
AGGGACTTGTAGATACTTCAATAGGCAATAATTTTGAGCCTGTGAATTCTAAAGCACCTCCAGGTGAACAATTTAATCACTTGAGAGCGTTAT
TCAAAAGTGCTAAACCTTGGCATGTTGTAAGGCCAAGGATTGTGCAAATGTTAGCGGATAACCTGTGCAACGTTTCAGATTGTGTAGTGTTTG
TCACGTGGTGTCATGGCCTAGAACTAACCACTTTGCGCTATTTTGTTAAAATAGGCAAGGACCAAGTTTGTTCTTGCGGTTCTAGAGCAACAA
CTTTTAATTCTCATACTCAGGCTTATGCTTGTTGGAAGCATTGCTTGGGTTTTGATTTTGTTTATAATCCACTCTTAGTGGATATTCAACAGT
GGGGTTATTCTGGTAACCTACAATTTAACCATGATTTGCATTGTAATGTGCATGGACACGCACATGTAGCTTCTGCGGATGCTATTATGACGC
GTTGTCTTGCAATTAATAATGCATTTTGTCAAGATGTCAACTGGGATTTAACTTACCCTCATATAGCAAATGAGGATGAAGTCAATTCTAGCT
GTAGATATTTACAACGCATGTATCTTAATGCATGTGTTGATGCTCTTAAAGTTAACGTTGTCTATGATATAGGCAACCCTAAAGGTATAAAAT
GTGTTAGACGTGGAGACTTAAATTTTAGATTCTATGATAAGAATCCAATAGTACCCAATGTCAAGCAGTTTGAGTATGACTATAATCAGCACA
AAGATAAGTTTGCTGATGGTCTTTGTATGTTTTGGAATTGTAATGTGGATTGTTATCCCGACAATTCCTTAGTTTGTAGGTACGACACACGAA
ATTTGAGTGTGTTTAACCTACCTGGTTGTAATGGTGGTAGCTTGTATGTTAACAAGCATGCATTCCACACACCTAAATTTGATCGCACTAGCT
TTCGTAATTTGAAAGCTATGCCATTCTTTTTCTATGACTCATCGCCTTGCGAGACCATTCAATTGGATGGAGTTGCGCAAGACCTTGTGTCAT
TAGCTACGAAAGATTGTATCACAAAATGCAACATAGGCGGTGCTGTTTGTAAAAAGCACGCACAAATGTATGCAGATTTTGTGACTTCTTATA
ATGCAGCTGTTACTGCTGGTTTTACTTTTTGGGTTACTAATAATTTTAACCCATATAATTTGTGGAAAAGTTTTTCAGCTCTCCAGTCTATCG
ACAATATTGCTTATAATATGTATAAGGGTGGTCATTATGATGCTATTGCAGGAGAAATGCCCACTATCGTAACTGGAGATAAAGTTTTTGTTA
TAGATCAAGGCGTAGAAAAAGCAGTTTTTTTTAATCAAACAATTCTGCCTACATCTGTAGCGTTTGAGCTGTATGCGAAGAGAAATATTCGCA
CACTGCCAAACAACCGTATTTTGAAAGGTTTGGGTGTAGATGTGACTAATGGATTTGTAATTTGGGATTACACGAACCAAACACCACTATACC
```

-continued

```
GTAATACTGTTAAGGTATGTGCATATACAGACATAGAACCAAATGGCCTAATAGTGCTGTATGATGATAGATATGGTGATTACCAGTCTTTTC
TAGCTGCTGATAATGCTGTTTTAGTTTCTACACAGTGTTACAAGCGGTATTCGTATGTAGAAATACCGTCAAACCTGCTTGTTCAGAACGGTA
TTCCGTTAAAAGATGGAGCGAACCTGTATGTTTATAAGCGTGTTAATGGTGCGTTTGTTACGCTACCTAACACATTAAACACACAGGGTCGCA
GTTATGAAACTTTTGAACCTCGTAGTGATGTTGAGCGTGATTTTCTCGACATGTCTGAGGAGAGTTTTGTAGAAAAGTATGGTAAAGAATTAG
GTCTACAGCACATACTGTATGGTGAAGTTGATAAGCCCCAATTAGGTGGTTTACACACTGTTATAGGTATGTGCAGACTTTTACGTGCGAATA
AGTTGAACGCAAAGTCTGTTACTAATTCTGATTCTGATGTCATGCAAAATTATTTTGTATTGGCAGACAATGGTTCCTACAAGCAAGTGTGTA
CTGTTGTGGATTTGCTGCTTGATGATTTCTTAGAACTTCTTAGGAACATACTGAAAGAGTATGGTACTAATAAGTCTAAAGTTGTAACAGTGT
CAATTGATTACCATAGCATAAATTTTATGACTTGGTTTGAAGATGGCATTATTAAAACATGTTATCCACAGCTTCAATCAGCATGGACGTGTG
GTTATAATATGCCTGAACTTTATAAAGTTCAGAATTGTGTTATGGAACCTTGCAACATTCCTAATTATGGTGTTGGAATAGCGTTGCCAAGTG
GTATTATGATGAATGTGGCAAAGTATACACAACTCTGTCAATACCTTTCGAAAACAACAATGTGTGTACCGCATAATATGCGAGTAATGCATT
TTGGAGCTGGAAGTGACAAAGGAGTGGCTCCAGGTAGTACTGTTCTTAAACAATGGCTCCCAGAAGGGACACTCCTTGTCGATAATGATATTG
TAGACTATGTGTCTGATGCACATGTTTCTGTGCTTTCAGATTGCAATAAATATAAGACAGAGCACAAGTTTGATCTTGTGATATCTGATATGT
ATACAGACAATGATTCAAAAAGAAAGCATGAAGGCGTGATAGCCAATAATGGCAATGATGACGTTTTCATATATCTCTCAAGTTTTCTTCGTA
ATAATTTGGCTCTAGGTGGTAGTTTTGCTGTAAAAGTGACAGAGACAAGTTGGCACGAAGTTTTATATGACATTGCACAGGATTGTGCATGGT
GGACAATGTTTTGTACAGCAGTGAATGCCTCTTCTTCAGAAGCATTCTTGGTTGGTGTTAATTATTTGGGTGCAAGTGAAAAGGTTAAGGTTA
GTGGAAAAACGCTGCACGCAAATTATATATTTTGGAGGAATTGTAATTATTTACAAACCTCTGCTTATAGTATATTTGACGTTGCTAAGTTTG
ATTTGAGATTGAAAGCAACACCAGTTGTTAATTTGAAAACTGAACAAAAGACAGACTTAGTCTTTAATTTAATTAAGTGTGGTAAGTTACTGG
TAAGAGATGTTGGTAACACCTCTTTTACTAGTGACTCTTTTGTGTGTACTATGTAGTGCTGCTTTGTATGACAGTAGTTCTTACGTTTACTAC
TACCAAAGTGCCTTTAGACCACCTAATGGTTGGCATTTACACGGGGGTGCTTATGCGGTAGTTAATATTTCTAGCGAATCTAATAATGCAGGC
TCTTCACCTGGGTGTATTGTTGGTACTATTCATGGTGGTCGTGTTGTTAATGCTTCTTCTATAGCTATGACGGCACCGTCATCAGGTATGGCT
TGGTCTAGCAGTCAGTTTTGTACTGCACACTGTAACTTTTCAGATACTACAGTGTTTGTTACACATTGTTATAAATATGATGGGTGTCCTATA
ACTGGCATGCTTCAAAAGAATTTTTTACGTGTTTCTGCTATGAAAAATGGCCAGCTTTTCTATAATTTAACAGTTAGTGTAGCTAAGTACCCT
ACTTTTAAATCATTTCAGTGTGTTAATAATTTAACATCCGTATATTTAAATGGTGATCTTGTTTACACCTCTAATGAGACCACAGATGTTACA
TCTGCAGGTGTTTATTTTAAAGCTGGTGGACCTATAACTTATAAAGTTATGAGAGAAGTTAAAGCCCTGGCTTATTTTGTTAATGGTACTGCA
CAAGATGTTATTTTGTGTGATGGATCACCTAGAGGCTTGTTAGCATGCCAGTATAATACTGGCAATTTTTCAGATGGCTTTTATCCTTTTATT
AATAGTAGTTTAGTTAAGCAGAAGTTTATTGTCTATCGTGAAAATAGTGTTAATACTACTTTTACGTTACACAATTTCACTTTTCATAATGAG
ACTGGCGCCAACCCTAATCCTAGTGGTGTTCAGAATATTCAAACTTACCAAACACAAACAGCTCAGAGTGGTTATTATAATTTTAATTTTTCC
TTTCTGAGTAGTTTTGTTTATAAGGAGTCTAATTTTATGTATGGATCTTATCACCCAAGTTGTAATTTTAGACTAGAAACTATTAATAATGGC
TTGTGGTTTAATTCACTTTCAGTTTCAATTGCTTACGGTCCTCTTCAAGGTGGTTGCAAGCAATCTGTCTTTAGTGGTAGAGCAACTTGTTGT
TATGCTTATTCATATGGAGGTCCTTCGCTGTGTAAAGGTGTTTATTCAGGTGAGTTAGATCTTAATTTTGAATGTGGACTGTTAGTTTATGTT
ACTAAGAGCGGTGGCTCTCGTATACAAACAGCCACTGAACCGCCAGTTATAACTCGACACAATTATAATAATATTACTTTAAATACTTGTGTT
GATTATAATATATATGGCAGAACTGGCCAAGGTTTTATTACTAATGTAACCGACTCAGCTGTTAGTTATAATTATCTAGCAGACGCAGGTTTG
GCTATTTTAGATACATCTGGTTCCATAGACATCTTTGTTGTACAAGGTGAATATGGTCTTACTTATTATAAGGTTAACCCTTGCGAAGATGTC
AACCAGCAGTTTGTAGTTTCTGGTGGTAAATTAGTAGGTATTCTTACTTCACGTAATGAGACTGGTTCTCAGCTTCTTGAGAACCAGTTTTAC
ATTAAAATCACTAATGGAACACGTCGTTTTAGACGTTCTATTACTGAAAATGTTGCAAATTGCCCTATGTTAGTTATGGTAAGTTTTGTATA
AAACCTGATGGTTCAATTGCCACAATAGTACCAAAACAATTGGAACAGTTTGTGGCACCTTTACTTAATGTTACTGAAAATGTGCTCATACCT
AACAGTTTTAATTTAACTGTTACAGATGAGTACATACAAACGCGTATGGATAAGGTCCAAATTAATTGTCTGCAGTATGTTTGTGGCAATTCT
CTGGATTGTAGAGATTTGTTTCAACAATATGGGCCTGTTTGTGACAACATATTGTCTGTAGTAAATAGTATTGGTCAAAAGAAGATATGGAA
CTTTTGAATTTCTATTCTTCTACTAAACCGGCTGGTTTTAATACACCATTTCTTAGTAATGTTAGCACTGGTGAGTTTAATATTTCTCTTCTG
TTAACAACTCCTAGTAGTCCTAGAAGGCGTTCTTTTATTGAAGACCTTCTATTTACAAGCGTTGAATCTGTTGGATTACCAACAGATGACGCA
```

-continued

```
TACAAAAATTGCACTGCAGGACCTTTAGGTTTTCTTAAGGACCTTGCGTGTGCTCGTGAATATAATGGTTTGCTTGTGTTGCCTCCCATTATA
ACAGCAGAAATGCAAATTTTGTATACTAGTTCTCTAGTAGCTTCTATGGCTTTTGGTGGTATTACTGCAGCTGGTGCTATACCTTTTGCCACA
CAACTGCAGGCTAGAATTAATCACTTGGGTATTACCCAGTCACTTTTGTTGAAGAATCAAGAAAAAATTGCTGCTTCCTTTAATAAGGCCATT
GGTCGTATGCAGGAAGGTTTTAGAAGTACATCTCTAGCATTACAACAAATTCAAGATGTTGTTAATAAGCAGAGTGCTATTCTTACTGAGACT
ATGGCATCACTTAATAAAAATTTTGGTGCTATTTCTTCTATGATTCAAGAAATCTACCAGCAACTTGACGCCATACAAGCAAATGCTCAAGTG
GATCGTCTTATAACTGGTAGATTGTCATCACTTTCTGTTTTAGCATCTGCTAAGCAGGCGGAGCATATTAGAGTGTCACAACAGCGTGAGTTA
GCTACTCAGAAAATTAATGAGTGTGTTAAGTCACAGTCTATTAGGTACTCCTTTTGTGGTAATGGACGACATGTTCTAACCATACCGCAAAAT
GCACCTAATGGTATAGTGTTTATACACTTTTCTTATACTCCAGATAGTTTTGTTAATGTTACTGCAATAGTGGGTTTTTGTGTAAAGCCAGCT
AATGCTAGTCAGTATGCAATAGTACCCGCTAATGGTAGGGGTATTTTATACAAGTTAATGGTAGTTACTACATCACAGCACGAGATATGTAT
ATGCCAAGAGCTATTACTGCAGGAGATATAGTTACGCTTACTTCTTGTCAAGCAAATTATGTAAGTGTAAATAAGACCGTCATTACTACATTC
GTAGACAATGATGATTTTGATTTTAATGACGAATTGTCAAAATGGTGGAATGACACTAAGCATGAGCTACCAGACTTTGACAAATTCAATTAC
ACAGTACCTATACTTGACATTGATAGTGAAATTGATCGTATTCAAGGCGTTATACAGGGTCTTAATGACTCTTTAATAGACCTTGAAAAACTT
TCAATACTCAAAACTTATATTAAGTGGCCTTGGTATGTGTGGTTAGCCATAGCTTTTGCCACTATTATCTTCATCTTAATACTAGGATGGGTT
TTCTTCATGACTGGATGTTGTGGTTGTTGTTGTGGATGCTTTGGCATTATGCCTCTAATGAGTAAGTGTGGTAAGAAATCTTCTTATTACACG
ACTTTTGATAACGATGTGGTAACTTAACAATACAGACCTAAAAAGTCTGTTTAATGATTCAAAGTCCCACGTCCTTCCTAATAGTATTAATTT
TTCTTTGGTGTAAACTTGTACTAAGTTGTTTTAGAGAGTTTATTATAGCGCTCCAACAACTAATACAAGTTTTACTCCAAATTATCAATAGTA
ACTTACAGCCTAGACTGACCCTTTGTCACAGTCTAGACTAATGTTAAACTTAGAAGCAATTATTGAAACTGGTGAGCAAGTGATTCAAAAAAT
CAGTTTCAATTTACAGCATATTTCAAGTGTATTAAACACAGAAGTATTTGACCCCTTTGACTATTGTTATTACAGAGGAGGTAATTTTTGGGA
AATAGAGTCAGCTGAAGATTGTTCAGGTGATGATGAATTTATTGAATAAGTCGCTAGAGGAAAATGGAAGTTTTCTAACAGCGCTTTATATAT
TTGTAGGATTTTTAGCACTTTATCTTCTAGGTAGAGCACTTCAAGCATTTGTACAGGCTGCTGATGCTTGTTGTTTATTTTGGTATACATGGG
TAGTAATTCCAGGAGCTAAGGGTACAGCCTTTGTATATAAGTATACATATGGTAGAAAACTTAACAATCCGGAATTAGAAGCAGTTATTGTCA
ACGAGTTTCCTAAGAACGGTTGGAATAATAAAAATCCAGCAAATTTTCAAGATGTCCAACGAGACAAATTGTACTCTTGACTTTGAACAGTCA
GTTGAGCTTTTTAAAGAGTATAATTTATTTATAACTGCATTCTTGTTGTTCTTAACCATAATACTTCAGTATGGCTATGCAACAAGAAGTAAG
TTTATTTATATACTGAAAATGATAGTGTTATGGTGCTTTTGGCCCCTTAACATTGCAGTAGGTGTAATTTCATGTATATACCCACCAAACACA
GGAGGTCTTGTCGCAGCGATAATACTTACAGTGTTTGCGTGTCTGTCTTTTGTAGGTTATTGGATCCAGAGTATTAGACTCTTTAAGCGGTGT
AGGTCATGGTGGTCATTTAACCCAGAATCTAATGCCGTAGGTTCAATACTCCTAACTAATGGTCAACAATGTAATTTTGCTATAGAGAGTGTG
CCAATGGTGCTTTCTCCAATTATAAAGAATGGTGTTCTTTATTGTGAGGGTCAGTGGCTTGCTAAGTGTGAACCAGACCACTTGCCTAAAGAT
ATATTTGTTTGTACACCGGATAGACGTAATATCTACCGTATGGTGCAGAAATATACTGGTGACCAAAGCGGAAATAAGAAACGGTTTGCTACG
TTTGTCTATGCAAAGCAGTCAGTAGATACTGGCGAGCTAGAAAGTGTAGCAACAGGAGGGAGTAGTCTTTACACCTAAATGTGTGTGTGTAGA
GAGTATTTAAAATTATTCTTTAATAGTGCCTCTATTTTAAGAGCGCATAATAGTATTATTTTTGAGGATATTAATATAAATCCTCTCTGTTTT
ATACTCTCTTTTCAAGAGCTATTATTTAAAAAACAGTTTTTCCACTCTTTTGTGCCAAAAACTATTGTTGTTAATGGTGTAACCTTTCAAGTA
GATAATGGAAAAGTCTACTACGAAGGAAAACCAATTTTTCAGAAAGGTTGTTGTAGGTTGTGGTTGAGTTATAAAAAAGATTAAACTACCTAC
TACACTTATTTTTATAAGAGGCGTTTTATCTTACAAGCGCTTAATAAATACGGACGATGAAATGGCTGACTAGTTTTGTAAGGGCAGTTATTT
CATGTTATAAACCCCTATTATTAACTCAATTAAGAGTATTAGATAGGTTAATCTTAGATCATGGACCAAAACACATCTTAACGTGTGTTAGGT
GCGTGATTTTGTTTCAATTAGATTTAGTTTATAGGTTGGCGTATACGCCTACTCAATCGCTGGTATGAATAATAGTAAAGATAATCCTTTTTG
CGGAGCAATAGCAAGAAAAGCGCGAATTTATCTGAGAGAAGGATTAGATTGTGTTTACTTTCTTAACAAAGCAGGACAAGCAGAGTCTTGTCC
CGCGTGTACCTCTCTAGTATTCCAGGGGAAAACTTGTGAGGAACACAAATATAATAATAATCTTTTGTCATGGCAAGCGGTAAGGCAACTGGA
AAGACAGATGCCCCAGCTCCAGTCATCAAACTAGGAGGACCAAAGCCACCTAAAGTTGGTTCTTCTGGAAATGTATCTTGGTTTCAAGCAATA
AAAGCCAAGAAGTTAAATTCACCTCCGCCTAAGTTTGAAGGTAGCGGTGTTCCTGATAATGAAAATCTAAAACCAAGTCAGCAGCATGGATAT
TGGAGACGCCAAGCTAGGTTTAAGCCAGGTAAAGGTGGAAGAAAACCAGTCCCAGATGCTTGGTATTTTTACTATACTGGAACAGGACCAGCC
GCTAACCTGAATTGGGGTGATAGCCAAGATGGTATAGTGTGGGTTGCTGGTAAGGGTGCTGATACTAAATTTAGATCTAATCAGGGTACTCGT
```

-continued

GACTCTGACAAGTTTGACCAATATCCGCTACGGTTTTCAGACGGAGGACCTGATGGTAATTTCCGTTGGGATTTCATTCCTCTGAATCGTGGC

AGGAGTGGGAGATCAACAGCAGCTTCATCAGCAGCATCTAGTAGAGCACCATCACGTGAAGTTTCGCGTGGTCGCAGGAGTGGTTCTGAAGAT

GATCTTATTGCTCGTGCAGCAAGGATAATTCAGGATCAGCAGAAGAAGGGTTCTCGCATTACAAAGGCTAAGGCTGATGAAATGGCTCACCGC

CGGTATTGCAAGCGCACTATTCCACCTAATTATAAGGTTGATCAAGTGTTTGGTCCCCGTACTAAAGGTAAGGAGGGAAATTTTGGTGATGAC

AAGATGAATGAGGAAGGTATTAAGGATGGGCGCGTTACAGCAATGCTCAACCTAGTTCCTAGCAGCCATGCTTGTCTTTTCGGAAGTAGAGTG

ACGCCCAGACTTCAACCAGATGGGCTGCACTTGAAATTTGAATTTACTACTGTGGTCCCACGTGATGATCCGCAGTTTGATAATTATGTAAAA

ATTTGTGATCAGTGTGTTGATGGTGTAGGAACACGTCCAAAAGATGATGAACCAAGACCAAAGTCACGCTCAAGTTCAAGACCTGCAACAAGA

GGAAATTCTCCAGCGCCAAGACAGCAGCGCCCTAAGAAGGAGAAAAAGCCAAAGAAGCAGGATGATGAAGTGGATAAAGCATTGACCTCAGAT

GAGGAGAGGAACAATGCACAGCTGGAATTTGATGATGAACCCAAGGTAATTAACTGGGGGGATTCAGCCCTAGGAGAGAATGAACTTTGAGTA

AAATTCAATAGTAAGAGTTAAGGAAGATAGGCATGTAGCTTGATTACCTACATGTCTATCGCCAGGGAAATGTCTAATTTGTCTACTTAGTAG

CCTGGAAACGAACGGTAGACCCTTAGATTTTAATTTAGTTTAATTTTTAGTTTAGTTTAAGTTAGTTTAGAGTAGGTATAAAGATGCCAGTGC

CGGGGCCACGCGGAGTACGACCGAGGGTACAGCACTAGGACGCCCATTAGGGGAAGAGCTAAATTTTAGTTTAAGTTAAGTTTAATTGGCTAT

GTATAGTTAAAATTTATAGGCTAGTATAGAGTTAGAGCAAAAAAAAAAAAAAAAAAAAAAAAA

Accessory Proteins

All coronaviruses encode a set of accessory protein genes of unknown function that are not required for replication in vitro, but may play a role in pathogenesis. IBV encodes two accessory genes, genes 3 and 5, which both express two accessory proteins 3a, 3b and 5a, 5b, respectively.

The nucleotide sequence for gene 3 and amino acid sequences for accessory proteins 3a and 3b in IBV MK41 are provided as SEQ ID NOs: 2-4, respectively.

(gene 3 nucleotide sequence-nucleotides 23831 to 24539 of SEQ ID NO: 1)

SEQ ID NO: 2

CTTAACAATACAGACCTAAAAAGTCTGTTTAATGATTCAAAGTCCCACGT

CCTTCCTAATAGTATTAATTTTTCTTTGGTGTAAACTTGTACTAAGTTGT

TTTAGAGAGTTTATTATAGCGCTCCAACAACTAATACAAGTTTTACTCCA

AATTATCAATAGTAACTTACAGCCTAGACTGACCCTTTGTCACAGTCTAG

ACTAATGTTAAACTTAGAAGCAATTATTGAAACTGGTGAGCAAGTGATTC

AAAAAATCAGTTTCAATTTACAGCATATTTCAAGTGTATTAAACACAGAA

GTATTTGACCCCTTTGACTATTGTTATTACAGAGGAGGTAATTTTTGGGA

AATAGAGTCAGCTGAAGATTGTTCAGGTGATGATGAATTTATTGAATAAG

TCGCTAGAGGAAAATGGAAGTTTTCTAACAGCGCTTTATATATTTGTAGG

ATTTTTAGCACTTTATCTTCTAGGTAGAGCACTTCAAGCATTTGTACAGG

CTGCTGATGCTTGTTGTTTATTTGGTATACATGGGTAGTAATTCCAGGA

GCTAAGGGTACAGCCTTTGTATATAAGTATACATATGGTAGAAAACTTAA

CAATCCGGAATTAGAAGCAGTTATTGTCAACGAGTTTCCTAAGAACGGTT

GGAATAATAAAAATCCAGCAAATTTTCAAGATGTCCAACGAGACAAATTG

TACTCTTGA (accessory protein 3a amino acid sequence)

SEQ ID NO: 3

MIQSPTSFLIVLIFLWCKLVLSCFREFIIALQQLIQVLLQIINSNLQPRL

TLCHSLD

-continued (accessory protein 3b amino acid sequence)

SEQ ID NO: 4

MLNLEAIIETGEQVIQKISFNLQHISSVLNTEVFDPFDYCYYRGGNFWEI

ESAEDCSGDDEFIE

Replicase

In addition to the structural and accessory genes, two-thirds of a coronavirus genome comprises the replicase gene (at the 5' end of the genome), which is expressed as two polyproteins, pp1a and pp1ab, in which pp1ab is an extension product of pp1a as a result of a −1 ribosomal shift mechanism. The two polyproteins are cleaved by two types of virus-encoded proteinases usually resulting in 16 non-structural proteins (nsp1-16); IBV lacks nsp1 thereby encoding nsp2-16.

Thus Gene 1 in IBV encodes 15 (16 in other coronaviruses) non-structural proteins (nsp2-16), which are associated with RNA replication and transcription.

The term 'replicase protein' is used herein to refer to the pp1a and pp1ab polyproteins or individual nsp subunits.

The term 'replicase gene' is used herein to refer to a nucleic acid sequence which encodes for replicase proteins.

A summary of the functions of coronavirus nsp proteins is provided in Table 1.

TABLE 1

| Nsp Protein | Key features |
|---|---|
| 1 | Conserved within but not between *coronavirus* genetic groups; potential regulatory functions in the host cell. |
| 2 | Dispensable for MHV and SARS-CoV replication in tissue culture |
| 3 | Acidic domain; macro domain with ADRP and poly(ADP-ribose)-binding activities; one or two ZBD-containing papain-like proteases; Y domain |
| 4 | Transmembrane domain |
| 5 | 3C-like main protease, homodimer |
| 6 | Transmembrane domain |
| 7 | Interacts with nsp8 to form a hexadecamer complex |
| 8 | Noncannonical RNA polymerase; interacts with nsp7 to form a hexadecameric complex |
| 9 | ssRNA-binding protein, dimer |

TABLE 1-continued

| Nsp Protein | Key features |
|---|---|
| 10 | RNA-binding protein, homododecamer, zinc-binding domain, known to interact with nsp14 and nsp16 |
| 11 | Unknown |
| 12 | RNA-dependent RNA polymerase |
| 13 | Zinc-binding domain, NTPase, dNTPase, 5'-to-3' RNA and DNA helicase, RNA 5'-triphosphate |
| 14 | 3'-to 5' exoribonuclease, zinc-binding domain and N7-methyltransferase |
| 15 | Uridylate-specific endoribonuclease, homohexamer |
| 16 | Putative ribose-2'-O-methyltransferase |

Nsp-3 is a large protein consisting of numerous distinct domains including a ubiquitin-like domain, an acidic domain, a papain-like protease (PL pro) domain, multiple transmembrane domains, and a macrodomain, which are separated by disordered linkers. The macrodomain is a globular domain with central sheets flanked by helices located at the N terminus of nsp-3. It contains ADP-ribose-1-phosphatase (ADRP) activity and binds to various forms of ADP-ribose. This domain is highly conserved in coronaviruses but found in only a few other virus families.

The nucleotide and protein sequences for nsp-3 in IBV M41 are provided as SEQ ID NOs: 5 and 6, respectively.

(nsp-3 nucleotide sequence-nucleotides 2548-7329 of SEQ ID NO: 1)
SEQ ID NO: 5

```
GGTAAAACTGTCACCTTTGGAGAAACTACTGTGCAAGAAATACCACCACCTGATGTTGTGTTTATT
AAGGTTAGCATTGAGTGTTGTGGTGAACCATGGAATACAATCTTCAAAAAGGCTTATAAGGAGCCC
ATTGAAGTAGAGACAGACCTCACAGTTGAACAATTGCTCTCTGTGGTCTATGAGAAAATGTGTGAT
GATCTCAAGCTGTTTCCGGAGGCTCCAGAACCACCACCATTTGAGAATGTCACACTTGTTGATAAG
AATGGTAAAGATTTGGATTGCATAAAATCATGCCATCTGATCTATCGTGATTATGAGAGCGATGAT
GACATCGAGGAAGAAGATGCAGAAGAATGTGACACGGATTCAGGTGATGCTGAGGAGTGTGACACT
AATTCAGAATGTGAAGAAGAAGATGAGGATACTAAAGTGTTGGCTCTTATACAAGACCCGGCAAGT
AACAAATATCCTCTGCCTCTTGATGATGATTATAGCGTCTACAATGGATGTATTGTTCATAAGGAC
GCTCTCGATGTTGTGAATTTACCATCTGGTGAAGAAACCTTTGTTGTCAATAACTGCTTTGAAGGG
GCTGTTAAAGCTCTTCCGCAGAAAGTTATTGATGTTCTAGGTGACTGGGGTGAGGCTGTTGATGCG
CAAGAACAATTGTGTCAACAAGAATCAACTCGGGTCATATCTGAGAAATCAGTTGAGGGTTTTACT
GGTAGTTGTGATGCAATGGCTGAACAAGCTATTGTTGAAGAGCAGGAAATAGTACCTGTTGTTGAA
CAAAGTCAGGATGTAGTTGTTTTTACACCTGCAGACCTAGAAGTTGTTAAAGAAACAGCAGAAGAG
GTTGATGAGTTTATTCTCATTTCTGCTGTCCCTAAAGAAGAAGTTGTGTCTCAGGAGAAAGAGGAG
CCACAGGTTGAGCAAGAGCCTACCCTAGTTGTTAAAGCACAACGTGAGAAGAAGGCTAAAAAGTTC
AAAGTTAAACCAGCTACATGTGAAAAACCCAAATTTTTGGAGTACAAAACATGTGTGGGTGATTTG
GCTGTTGTAATTGCCAAAGCATTGGATGAGTTTAAAGAGTTCTGCATTGTAAACGCTGCAAATGAG
CACATGTCGCATGGTGGTGGCGTTGCAAAGGCAATTGCAGACTTTTGTGGACCGGACTTTGTTGAA
TATTGCGCGGACTATGTTAAGAAACATGGTCCACAGCAAAAACTTGTCACACCTTCATTTGTTAAA
GGCATTCAATGTGTGAATAATGTTGTAGGACCTCGCCATGGAGACAGCAACTTGCGTGAGAAGCTT
GTTGCTGCTTACAAGAGTGTTCTTGTAGGTGGAGTGGTTAACTATGTTGTGCCAGTTCTCTCATCA
GGGATTTTTGGTGTAGATTTTAAAATATCAATAGATGCTATGCGCGAAGCTTTTAAAGGTTGTGCC
ATACGCGTTCTTTTATTTTCTCTGAGTCAAGAACACATCGATTATTTCGATGCAACTTGTAAGCAG
AAGACAATTTATCTTACGGAGGATGGTGTTAAATACCGCTCTGTTGTTTTAAAACCTGGTGATTCT
TTGGGTCAATTTGGACAGGTTTTTGCAAGAAATAAGGTAGTCTTTTCGGCTGATGATGTTGAGGAT
AAAGAAATCCTCTTTATACCCACAACTGACAAGACTATTCTTGAATATTATGGTTTAGATGCGCAA
AAGTATGTAACATATTTGCAAACGCTTGCGCAGAAATGGGATGTTCAATATAGAGACAATTTTGTT
ATATTAGAGTGGCGTGACGGAAATTGCTGGATTAGTTCAGCAATAGTTCTCCTTCAAGCTGCTAAA
ATTAGATTTAAAGGTTTTCTTGCAGAAGCATGGGCTAAACTGTTGGGTGGAGATCCTACAGACTTT
GTTGCCTGGTGTTATGCAAGTTGCAATGCTAAAGTAGGTGATTTTTCAGATGCTAATTGGCTTTTG
GCCAATTTAGCAGAACATTTTGACGCAGATTACACAAATGCACTTCTTAAGAAGTGTGTGTCGTGC
```

-continued

```
AATTGTGGTGTTAAGAGTTATGAACTTAGGGGTCTTGAAGCCTGTATTCAGCCAGTTCGAGCACCT

AATCTTCTACATTTTAAAACGCAATATTCAAATTGCCCAACCTGTGGTGCAAGTAGTACGGATGAA

GTAATAGAAGCTTCATTACCGTACTTATTGCTTTTTGCTACTGATGGTCCTGCTACAGTTGATTGT

GATGAAAATGCTGTAGGGACTGTTGTTTTCATTGGCTCTACTAATAGTGGCCATTGTTATACACAA

GCCGATGGTAAGGCTTTTGACAATCTTGCTAAGGATAGAAAATTTGGAAGGAAGTCGCCTTACATT

ACAGCAATGTATACACGTTTTTCTCTTAGGAGTGAAAATCCCCTACTTGTTGTTGAACATAGTAAG

GGTAAAGCTAAAGTAGTAAAAGAAGATGTTTCTAACCTTGCTACTAGTTCTAAAGCCAGTTTTGAC

GATCTTACTGACTTTGAACAGTGGTATGATAGCAACATCTATGAGAGTCTTAAAGTGCAGGAGACA

CCTGATAATCTTGATGAATATGTGTCATTTACGACAAAGGAAGATTCTAAGTTGCCACTGACACTT

AAAGTTAGAGGTATCAAATCAGTTGTTGACTTTAGGTCTAAGGATGGTTTTACTTATAAGTTAACA

CCTGATACTGATGAAAATTCAAAAACACCAGTCTACTACCCAGTCTTGGATTCTATTAGTCTTAGG

GCAATATGGGTTGAAGGCAGTGCTAATTTTGTTGTTGGGCATCCAAATTATTATAGTAAGTCTCTC

CGAATTCCCACGTTTTGGGAAAATGCCGAGAGCTTTGTTAAAATGGGTTATAAAATTGATGGTGTA

ACTATGGGCCTTTGGCGTGCAGAACACCTTAATAAACCTAATTTGGAGAGAATTTTTAACATTGCT

AAGAAAGCTATTGTTGGATCTAGTGTTGTTACTACGCAGTGTGGTAAAATACTAGTTAAAGCAGCT

ACATACGTTGCCGATAAAGTAGGTGATGGTGTAGTTCGCAATATTACAGATAGAATTAAGGGTCTT

TGTGGATTCACACGTGGCCATTTTGAAAAGAAAATGTCCCTACAATTTCTAAAGACACTTGTGTTC

TTTTTCTTTTATTTCTTAAAGGCTAGTGCTAAGAGTTTAGTTTCTAGCTATAAGATTGTGTTATGT

AAGGTGGTGTTTGCTACCTTACTTATAGTGTGGTTTATATACACAAGTAATCCAGTAGTGTTTACT

GGAATACGTGTGCTAGACTTCCTATTTGAAGGTTCTTTATGTGGTCCTTATAATGACTACGGTAAA

GATTCTTTTGATGTGTTACGCTATTGTGCAGGTGATTTTACTTGTCGTGTGTGTTTACATGATAGA

GATTCACTTCATCTGTACAAACATGCTTATAGCGTAGAACAAATTTATAAGGATGCAGCTTCTGGC

ATTAACTTTAATTGGAATTGGCTTTATTTGGTCTTTCTAATATTATTTGTTAAGCCAGTGGCAGGT

TTTGTTATTATTTGTTATTGTGTTAAGTATTTGGTATTGAGTTCAACTGTGTTGCAAACTGGTGTA

GGTTTTCTAGATTGGTTTGTAAAAACAGTTTTTACCCATTTTAATTTTATGGGAGCGGGATTTTAT

TTCTGGCTCTTTTACAAGATATACGTACAAGTGCATCATATATTGTACTGTAAGGATGTAACATGT

GAAGTGTGCAAGAGAGTTGCACGCAGCAACAGGCAAGAGGTTAGCGTTGTAGTTGGTGGACGCAAG

CAAATAGTGCATGTTTACACTAATTCTGGCTATAACTTTTGTAAGAGACATAATTGGTATTGTAGA

AATTGTGATGATTATGGTCACCAAAATACATTTATGTCCCCTGAAGTTGCTGGCGAGCTTTCTGAA

AAGCTTAAGCGCCATGTTAAACCTACAGCATATGCTTACCACGTTGTGTATGAGGCATGCGTGGTT

GATGATTTTGTTAATTTAAAATATAAGGCTGCAATTCCTGGTAAGGATAATGCATCTTCTGCTGTT

AAGTGTTTCAGTGTTACAGATTTTTTAAAGAAAGCTGTTTTTCTTAAGGAGGCATTGAAATGTGAA

CAAATATCTAATGATGGTTTTATAGTGTGTAATACACAGAGTGCGCATGCACTAGAGGAAGCAAAG

AATGCAGCCGTCTATTATGCGCAATATCTGTGTAAGCCAATACTTATACTTGACCAGGCACTTTAT

GAGCAATTAATAGTAGAGCCTGTGTCAAGAGTGTTATAGATAAAGTGTGTAGCATTTTGTCTAAT

ATAATATCTGTAGATACTGCAGCTTTAAATTATAAGGCAGGCACACTTCGTGATGCTCTGCTTTCT

ATTACTAAAGACGAAGAAGCCGTAGATATGGCTATCTTCTGCCACAATCATGAAGTGGAATACACT

GGTGACGGTTTTACTAATGTGATACCGTCATATGGTATGGACACTGATAAGTTGACACCTCGTGAT

AGAGGGTTTTTGATAAATGCAGATGCTTCTATTGCTAATTTAAGAGTCAAAAATGCTCCTCCGGTA

GTATGGAAGTTTTCTGATCTTATTAAATTGTCTGACAGTTGCCTTAAATATTTAATTTCAGCTACT
```

-continued

```
GTCAAGTCAGGAGGTCGTTTCTTTATAACAAAGTCTGGTGCTAAACAAGTTATTTCTTGTCATACC

CAGAAACTGTTGGTAGAGAAAAAGGCAGGT (nsp-3 amino acid sequence)
                                                              SEQ ID NO: 6
GKTVTFGETTVQEIPPPDVVFIKVSIECCGEPWNTIFKKAYKEPIEVETDLTVEQLLSVVYEKMCD

DLKLFPEAPEPPPFENVTLVDKNGKDLDCIKSCHLIYRDYESDDDIEEEDAEECDTDSGDAEECDT

NSECEEEDEDTKVLALIQDPASNKYPLPLDDDYSVYNGCIVHKDALDVVNLPSGEETFVVNNCFEG

AVKALPQKVIDVLGDWGEAVDAQEQLCQQESTRVISEKSVEGFTGSCDAMAEQAIVEEQEIVPVVE

QSQDVVVFTPADLEVVKETAEEVDEFILISAVPKEEVVSQEKEEPQVEQEPTLVVKAQREKKAKKF

KVKPATCEKPKFLEYKTCVGDLAVVIAKALDEFKEFCIVNAANEHMSHGGGVAKAIADFCGPDFVE

YCADYVKKHGPQQKLVTPSFVKGIQCVNNVVGPRHGDSNLREKLVAAYKSVLVGGVVNYVVPVLSS

GIFGVDFKISIDAMREAFKGCAIRVLLFSLSQEHIDYFDATCKQKTIYLTEDGVKYRSVVLKPGDS

LGQFGQVFARNKVVFSADDVEDKEILFIPTTDKTILEYYGLDAQKYVTYLQTLAQKWDVQYRDNFV

ILEWRDGNCWISSAIVLLQAAKIRFKGFLAEAWAKLLGGDPTDFVAWCYASCNAKVGDFSDANWLL

ANLAEHFDADYTNALLKKCVSCNCGVKSYELRGLEACIQPVRAPNLLHFKTQYSNCPTCGASSTDE

VIEASLPYLLLFATDGPATVDCDENAVGTVVFIGSTNSGHCYTQADGKAFDNLAKDRKFGRKSPYI

TAMYTRFSLRSENPLLVVEHSKGKAKVVKEDVSNLATSSKASFDDLTDFEQWYDSNIYESLKVQET

PDNLDEYVSFTTKEDSKLPLTLKVRGIKSVVDFRSKDGFTYKLTPDTDENSKTPVYYPVLDSISLR

AIWVEGSANFVVGHPNYYSKSLRIPTFWENAESFVKMGYKIDGVTMGLWRAEHLNKPNLERIFNIA

KKAIVGSSVVTTQCGKILVKAATYVADKVGDGVVRNITDRIKGLCGFTRGHFEKKMSLQFLKTLVF

FFFYFLKASAKSLVSSYKIVLCKVVFATLLIVWFIYTSNPVVFTGIRVLDFLFEGSLCGPYNDYGK

DSFDVLRYCAGDFTCRVCLHDRDSLHLYKHAYSVEQIYKDAASGINFNWNWLYLVFLILFVKPVAG

FVIICYCVKYLVLSSTVLQTGVGFLDWFVKTVFTHFNFMGAGFYFWLFYKIYVQVHHILYCKDVTC

EVCKRVARSNRQEVSVVVGGRKQIVHVYTNSGYNFCKRHNWYCRNCDDYGHQNTFMSPEVAGELSE

KLKRHVKPTAYAYHVVYEACVVDDFVNLKYKAAIPGKDNASSAVKCFSVTDFLKKAVFLKEALKCE

QISNDGFIVCNTQSAHALEEAKNAAVYYAQYLCKPILILDQALYEQLIVEPVSKSVIDKVCSILSN

IISVDTAALNYKAGTLRDALLSITKDEEAVDMAIFCHNHEVEYTGDGFTNVIPSYGMDTDKLTPRD

RGFLINADASIANLRVKNAPPVVWKFSDLIKLSDSCLKYLISATVKSGGRFFITKSGAKQVISCHT

QKLLVEKKAG
```

Reduced Pathogenicity

The live, attenuated coronavirus of the present invention comprises at least one mutation which causes the virus to have reduced pathogenicity compared to the corresponding wild-type coronavirus.

The term "attenuated" as used herein refers to a virus that exhibits said reduced pathogenicity and may be classified as non-virulent. A live, attenuated virus is a weakened replicating virus still capable of stimulating an immune response and producing immunity but not causing the actual illness.

The term "pathogenicity" is used herein according to its normal meaning to refer to the potential of the virus to cause disease in a subject. Typically the pathogenicity of a coronavirus is determined by assaying disease associated symptoms, for example wheezing, snicking and reduction in tracheal ciliary activity.

The term "reduced pathogenicity" is used to describe that the level of pathogenicity of a coronavirus is decreased, lessened or diminished compared to a corresponding, wild-type coronavirus.

In one embodiment, the coronavirus of the present invention has a reduced pathogenicity compared to the parental M41-CK virus from which it was derived or a control coronavirus. The control coronavirus may be a coronavirus with a known pathogenicity.

The pathogenicity of a coronavirus may be assessed utilising methods well-known in the art. Typically, pathogenicity is assessed by assaying clinical symptoms in a subject challenged with the virus, for example a chicken.

As an illustration, the chicken may be challenged at 8-24 days old by nasal or ocular inoculation. Clinical symptoms, associated with IBV infection, may be assessed 3-10 days post-infection. Clinical symptoms commonly assessed to determine the pathogenicity of a coronavirus, for example an IBV, include gasping, coughing, wheezing, snicking, depression, ruffled feathers and loss of tracheal ciliary activity.

The attenuated coronavirus of the present invention may cause a reduced level of clinical symptoms compared to the corresponding wild-type coronavirus.

For example an attenuated coronavirus may cause a number of snicks per bird per minute which is less than 90%, less than 80%, less than 70%, less than 60%, less than 50%, less than 40%, less than 30%, less than 20% or less than 10% of the number of snicks caused by a wild type virus.

An attenuated coronavirus according to the present invention may cause wheezing in less than 70%, less than 60%, less than 50%, less than 40%, less than 30%, less than 20% or less than 10% of the number of birds in a flock infected with a wild type virus.

An attenuated coronavirus according to the present invention may result in tracheal ciliary activity which is at least 60%, at least 70%, at least 80%, at least 90% or at least 95% of the level of tracheal ciliary activity in uninfected birds.

An attenuated coronavirus according to the present invention may cause clinical symptoms, as defined in Table 2, at a lower level than a wild type coronavirus.

Reduced pathogenicity in terms of the embryo may mean that the attenuated coronavirus causes less reduction in hatchability compared to a corresponding, wild-type control coronavirus. Thus the term "without being pathogenic to the embryo" in the context of the present invention may mean "without causing reduced hatchability" when compared to a control coronavirus.

A suitable attenuated coronavirus may be identified using methods which are known in the art. For example comparative challenge experiments following in ovo vaccination of embryos with or without maternally-derived antibodies may be performed (i.e. wherein the layer has or has not been vaccinated against IBV).

If the attenuated coronavirus propagates at a level which is too high, the embryo will not hatch or will not be viable

TABLE 2

| IBV severity limits based on clinical signs: | |
|---|---|
| Snicking (sneezing)<br>Nasal exudate<br>Watery eyes<br>Swollen infraorbital sinuses<br>Rales (vibration in trachea or bronchi region) | IBV specific: Mild (N.B. Respiratory signs become apparent from 2-3 dpi if they are going to occur and can continue for up to 7 d). |
| Hunched posture/depressed<br>Fluffed up feathers<br>Eating and drinking less | Mild, if exceed 2 d increase to moderate |
| Drinking in excess: evident by fluid filled crop or measured water intake | IBV specific: Mild, if exceed 24 h increase to moderate for a max of 2 d. If still drinking in excess then kill by schedule 1 method. |
| Less active but still evade capture<br>Weight loss<br>Not eating or drinking | Mild, if exceed 1 d increase to moderate. |
| Birds sit alone and does not evade capture<br>Severe respiratory distress: e.g. excessive gasping<br>Snicking and/or rales for 7 d in total | Moderate: birds at end point. Kill by schedule 1 method. |
| Found dead | Severe: report to project license holder.<br>Full post-mortem to be performed. |

The attenuated coronavirus of the present invention may replicate at non-pathogenic levels in ovo.

While developing vaccines to be administered in ovo to chicken embryos, attention must be paid to two points: the effect of maternal antibodies on the vaccines and the effect of the vaccines on the embryo. Maternal antibodies are known to interfere with active immunization. For example, vaccines with mild strains do not induce protective antibody levels when administered to broiler chickens with maternal antibodies as these strains are neutralized by the maternal antibody pool.

Thus a viral particle must be sufficiently efficient at replicating and propagating to ensure that it is not neutralized by the maternally-derived antibodies against the virus. Maternally-derived antibodies are a finite pool of effective antibodies, which decrease as the chicken ages, and neutralization of the virus in this manner does not equate to the establishment of long-term immunity for the embryo/chick. In order to develop long-term immunity against the virus, the embryo and hatched chicken must develop an appropriate protective immune response which is distinct to the effect of the maternally-derived antibodies.

To be useful for in ovo vaccination, the virus must also not replicate and propagate at a level which causes it to be pathogenic to the embryo.

following hatching (i.e. the virus is pathogenic to the embryo). A virus which is pathogenic to the embryo may kill the embryo.

If the attenuated coronavirus demonstrates a reduction in viral replication and propagation which is too great, the virus will be neutralised by the maternally-derived antibodies. Subsequent challenge of the chick with IBV will therefore result in the development of clinical symptoms (for example wheezing, snicking, loss of ciliary activity) and the onset of disease in the challenged chick as it will have failed to develop effective immunity against the virus.

Variant

As used herein, the term 'variant' is synonymous with 'mutant' and refers to a nucleic acid or amino acid sequence which differs in comparison to the corresponding wild-type sequence.

A variant/mutant sequence may arise naturally, or may be created artificially (for example by site-directed mutagenesis). The mutant may have at least 70, 80, 90, 95, 98 or 99% sequence identity with the corresponding portion of the wild type sequence. The mutant may have 20, 10, 5, 4, 3, 2 or 1 mutation(s) over the corresponding portion of the wild-type sequence.

The term "wild type" is used to mean a gene or protein having a nucleotide or amino acid sequence which is identical with the native gene or protein respectively (i.e. the viral gene or protein).

Identity comparisons can be conducted by eye, or more usually, with the aid of readily available sequence comparison programs. These commercially available computer programs can calculate % identity between two or more sequences. A suitable computer program for carrying out such an alignment is the GCG Wisconsin Bestfit package (University of Wisconsin, U.S.A.; Devereux et al., 1984, Nucleic Acids Research 12:387). Examples of other software that can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools, ClustalX (see Larkin et al. (2007) Clustal W and Clustal X version 2.0. Bioinformatics, 23:2947-2948). Both BLAST and FASTA are available for offline and online searching (see Ausubel et al., 1999 ibid, pages 7-58 to 7-60). However, for some applications, it is preferred to use the GCG Bestfit program. A new tool, called BLAST 2 Sequences is also available for comparing protein and nucleotide sequence (see FEMS Microbiol Lett 1999 174(2): 247-50; FEMS Microbiol Lett 1999 177(1): 187-8 and tatiana@ncbi.nlm.nih.gov).

The sequence may have one or more deletions, insertions or substitutions of amino acid residues which produce a silent change and result in a functionally equivalent molecule. Deliberate amino acid substitutions may be made on the basis of similarity in polarity, charge, solubility, hydrophobicity, hydrophilicity, and/or the amphipathic nature of the residues as long as the activity is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Ammayappan et al (Arch Virol (2009) 154:495-499) reports the identification of sequence changes responsible for the attenuation of IBV strain Arkansas DPI. The study identified 17 amino acid changes in a variety of IBV proteins following multiple passages, approx. 100, of the virus in embryonated eggs. It was not investigated whether the attenuated virus (Ark DPI 101) is capable of replicating in the presence of maternally-derived antibodies against the virus in ovo, without being pathogenic to the embryo. Given that this virus was produced by multiple passage in SPF embryonated eggs, similar methodology for classical IBV vaccines, it is likely that this virus is pathogenic for embryos. The virus may also be sensitive to maternally-derived antibodies if the hens were vaccinated with a similar serotype.

The coronavirus of the present invention comprises a mutation in non-structural protein nsp-3 and/or deletion of accessory proteins 3a and/or 3b, which mutation causes the virus to have reduced pathogenicity compared to a wild-type coronavirus.

The mutation in nsp-3 may comprise a mutation in the adenosine diphosphate-ribose-1'-phophatase (ADRP) region of nsp-3. The ADRP region of nsp-3 may comprise or consist of residues 332 to 491 of SEQ ID NO: 6 (encoded by nucleotides 994 to 1473 of SEQ ID NO: 5, for example). Accordingly, the mutation in nsp-3 may comprise one or more amino acids mutations compared to the amino acids shown as positions 332 to 491 of SEQ ID NO: 6. The mutation in nsp-3 may comprise one or more amino acid mutations compared to the amino acids shown as positions 332 to 491, 350 to 470, 350 to 450, 350 to 425, 350 to 400, 350 to 380, 360 to 380 or 370 to 380 of SEQ ID NO: 6. The mutation in nsp-3 may comprise one or more amino acid mutations compared to the amino acids shown as positions 370 to 380 of SEQ ID NO: 6.

The mutation in nsp-3 may comprise one or more amino acid mutations selected from the list of:
 a) Asn (N) to Ala (A) at position 373 in SEQ ID NO: 6; and
 b) Gly (G) to Ser (S) at position 379 in SEQ ID NO: 6.

The mutation in nsp-3 may comprise one or more nucleotide substitutions which encodes an amino acid mutation as described herein.

The mutation in nsp-3 may comprise one or more nucleotide substitutions selected from the list of:
 a) A to G at nucleotide position 1116 and A to C at nucleotide position 1117 compared to the sequence shown as SEQ ID NO: 5; and
 b) G to A at nucleotide position 1138 compared to the sequence shown as SEQ ID NO: 5.

As used herein, the term "substitution" is synonymous with the term mutation and means that the nucleotide at the identified position differs to that of the wild-type nucleotide sequence.

The mutation in nsp-3 may comprise the amino acid mutation Asn (N) to Ala (A) at position 373 in SEQ ID NO: 3.

The mutation in nsp-3 may comprise the amino acid mutation Gly (G) to Ser (S) at position 379 in SEQ ID NO: 3.

The mutation in nsp-3 may comprise the amino acid mutations Asn (N) to Ala (A) at position 373 and Gly (G) to Ser (S) at position 379 in SEQ ID NO: 3.

The attenuated coronavirus may also be defined at the nucleotide level.

For example the nucleotide sequence of the attenuated coronavirus of the present invention may comprise one or more mutations selected from the list of:
 a) A to G at nucleotide position 1116 and A to C at nucleotide position 1117 compared to the sequence shown as SEQ ID NO: 5; and
 b) G to A at nucleotide position 1138 compared to the sequence shown as SEQ ID NO: 5.

The mutation in nsp-3 may comprise the mutation A to G at nucleotide position 1116 and A to C at nucleotide position 1117 compared to the sequence shown as SEQ ID NO: 5.

The mutation in nsp-3 may comprise the mutation G to A at nucleotide position 1138 compared to the sequence shown as SEQ ID NO: 5.

The mutation in nsp-3 may comprise the mutation A to G at nucleotide position 1116, A to C at nucleotide position 1117 and G to A at nucleotide position 1138 compared to the sequence shown as SEQ ID NO: 5.

The live, attenuated coronavirus of the present invention may comprise deletion of accessory proteins 3a and/or 3b. This mutation may be achieved by partial or full deletion of gene 3. Therefore in one aspect of the invention all or a portion of accessory protein 3a is deleted. According to another aspect of the invention all or a portion of accessory protein 3b is deleted. In a further aspect of the invention all or a portion of both accessory proteins 3a and 3b are deleted. In one aspect of the invention accessory protein 3a is deleted. According to another aspect of the invention accessory protein 3b is deleted. In a further aspect of the invention both accessory proteins 3a and 3b are deleted.

The deletion of accessory proteins 3a and 3b may comprise a deletion from about nucleotide position 37 to about 384 of the gene 3 sequence shown as SEQ ID NO: 2. The deletion of accessory proteins 3a and 3b may comprise a deletion from nucleotide position 37 to 384 of the gene 3 sequence shown as SEQ ID NO: 2.

The deletion of accessory proteins 3a and 3b may comprise a deletion from about nucleotide position 23867 to about 24214 of the IBV M41-CK sequence shown as SEQ ID NO: 1. The deletion of accessory proteins 3a and 3b may comprise a deletion from nucleotide position 23867 to 24214 of the IBV M41-CK sequence shown as SEQ ID NO:

The nucleotide sequence may comprise any combination of the nucleotide mutations listed above.

In one embodiment, the coronavirus of the present invention may comprise a mutation in non-structural protein nsp-3 and deletion of accessory proteins 3a and/or 3b.

In a further embodiment, the coronavirus of the present invention may comprise a mutation in the ADRP region of nsp-3 and deletion of accessory proteins 3a and 3b.

For example the nucleotide sequence of the attenuated coronavirus of the present invention may comprise the following mutations:
 a) A to G at nucleotide position 1116 and A to C at nucleotide position 1117 compared to the sequence shown as SEQ ID NO: 5; and/or
 b) G to A at nucleotide position 1138 compared to the sequence shown as SEQ ID NO: 5; and
 c) deletion from nucleotide position 37 to 384 of the gene 3 sequence shown as SEQ ID NO: 2.

The nucleotide sequence may not comprise a substitution which corresponds to the C12008T substitution reported by Ammayappan et al. (as above).

The nucleotide sequence may be natural, synthetic or recombinant. It may be double or single stranded, it may be DNA or RNA or combinations thereof. It may, for example, be cDNA, PCR product, genomic sequence or mRNA.

The nucleotide sequence may be codon optimised for production in the host/host cell of choice.

It may be isolated, or as part of a plasmid, virus or host cell.

Plasmid

A plasmid is an extra-chromosomal DNA molecule separate from the chromosomal DNA which is capable of replicating independently of the chromosomal DNA. They are usually circular and double-stranded.

Plasmids, or vectors (as they are sometimes known), may be used to express a protein in a host cell. For example a bacterial host cell may be transfected with a plasmid capable of encoding a particular protein, in order to express that protein. The term also includes yeast artificial chromosomes and bacterial artificial chromosomes which are capable of accommodating longer portions of DNA.

The plasmid of the present invention comprises a nucleotide sequence capable of encoding a defined region of the attenuated coronavirus. It may also comprise one or more additional coronavirus nucleotide sequence(s), or nucleotide sequence(s) capable of encoding one or more other coronavirus proteins such as the S gene.

The plasmid may also comprise a resistance marker, such as the guanine xanthine phosphoribosyltransferase gene (gpt) from *Escherichia coli*, which confers resistance to mycophenolic acid (MPA) in the presence of xanthine and hypoxanthine and is controlled by the vaccinia virus P7.5 early/late promoter.

Recombinant Vaccinia Virus

The present invention also relates to a recombinant vaccinia virus (rVV) comprising a variant gene as defined herein.

The recombinant vaccinia virus (rVV) may be made using a vaccinia-virus based reverse genetics system.

In this respect, the present invention also provides a method for making a viral particle by:
 (i) transfecting a plasmid as described in the previous section into a host cell;
 (ii) infecting the host cell with a recombining virus comprising the genome of a coronavirus strain with a nsp-3 gene or gene 3;
 (iii) allowing homologous recombination to occur between the gene sequences in the plasmid and the corresponding sequences in the recombining virus genome to produce a modified gene;
 (iv) selecting for recombining virus comprising the modified gene.

The term 'modified gene' refers to a nsp-3 gene or gene 3 which comprises a mutation as described in connection with the first aspect of the present invention. Specifically, the term refers to a gene which is derived from a wild-type gene but comprises a nucleotide sequence which causes it to encode a variant protein as defined herein, or in the case of gene 3, to not encode part or all of the proteins 3a and 3b The recombination may involve all or part of the modified gene. The recombination may involve a nucleotide sequence which encodes for an amino acid mutation or comprises a nucleotide substitution as defined above.

The genome of the coronavirus strain may lack the part of the protein corresponding to the part provided by the plasmid, so that a modified protein is formed through insertion of the nucleotide sequence provided by the plasmid.

The recombining virus is one suitable to allow homologous recombination between its genome and the plasmid. The vaccinia virus is particularly suitable as homologous recombination is routinely used to insert and delete sequences for the vaccinia virus genome.

The above method optionally includes the step:
 (v) recovery of recombinant coronavirus comprising the modified gene from the DNA from the recombining virus from step (iv).

Methods for recovering recombinant coronavirus, such as recombinant IBV, are known in the art (See Britton et al (2005) see page 24; and PCT/GB2010/001293).

For example, the DNA from the recombining virus from step (iv) may be inserted into a plasmid and used to transfect cells which express cytoplasmic T7 RNA polymerase. The cells may, for example be pre-infected with a fowlpox virus expressing T7 RNA polymerase. Recombinant coronavirus may then be isolated, for example, from the growth medium.

When the plasmid is inserted into the vaccinia virus genome, an unstable intermediate is formed. Recombinants comprising the plasmid may be selected for e.g. using a resistance marker on the plasmid.

Positive recombinants may then be verified to contain the modified gene by, for example, PCR and sequencing.

Large stocks of the recombining virus including the modified gene (e.g. recombinant vaccinia virus, (rVV) may be grown up and the DNA extracted in order to carry out step (v)).

Suitable reverse genetics systems are known in the art (Casais et al (2001) J. Virol 75:12359-12369; Casais et al (2003) J. Virol. 77:9084-9089; Britton et al (2005) J. Virological Methods 123:203-211; Armesto et al (2008) Methods in Molecular Biology 454:255-273).

Cell

The coronavirus may be used to infect a cell.

Coronavirus particles may be harvested, for example from the supernatant, by methods known in the art, and optionally purified.

The cell may be used to produce the coronavirus particle.

Thus the present invention also provides a method for producing a coronavirus which comprises the following steps:
(i) infection of a cell with a coronavirus according to the invention;
(ii) allowing the virus to replicate in the cell; and
(iii) harvesting the progeny virus.

The present invention also provides a cell capable of producing a coronavirus according to the invention using a reverse genetics system. For example, the cell may comprise a recombining virus genome comprising a nucleotide sequence capable of encoding a modified gene of the present invention.

The cell may be able to produce recombinant recombining virus (e.g. vaccinia virus) containing the mutation(s).

Alternatively the cell may be capable of producing recombinant coronavirus by a reverse genetics system. The cell may express or be induced to express T7 polymerase in order to rescue the recombinant viral particle.

Vaccine

The coronavirus may be used to produce a vaccine. The vaccine may be a live attenuated form of the coronavirus of the present invention and may further comprise a pharmaceutically acceptable carrier. As defined herein, "pharmaceutically acceptable carriers" suitable for use in the invention are well known to those of skill in the art. Such carriers include, without limitation, water, saline, buffered saline, phosphate buffer, alcohol/aqueous solutions, emulsions or suspensions. Other conventionally employed diluents and excipients may be added in accordance with conventional techniques. Such carriers can include ethanol, polyols, and suitable mixtures thereof, vegetable oils, and injectable organic esters. Buffers and pH adjusting agents may also be employed. Buffers include, without limitation, salts prepared from an organic acid or base. Representative buffers include, without limitation, organic acid salts, such as salts of citric acid, e.g., citrates, ascorbic acid, gluconic acid, histidine-Hel, carbonic acid, tartaric acid, succinic acid, acetic acid, or phthalic acid, Tris, trimethanmine hydrochloride, or phosphate buffers. Parenteral carriers can include sodium chloride solution, Ringer's dextrose, dextrose, trehalose, sucrose, and sodium chloride, lactated Ringer's or fixed oils. Intravenous carriers can include fluid and nutrient replenishers, electrolyte replenishers, such as those based on Ringer's dextrose and the like. Preservatives and other additives such as, for example, antimicrobials, antioxidants, chelating agents (e.g., EDTA), inert gases and the like may also be provided in the pharmaceutical carriers. The present invention is not limited by the selection of the carrier. The preparation of these pharmaceutically acceptable compositions, from the above-described components, having appropriate pH isotonicity, stability and other conventional characteristics is within the skill of the art. See, e.g., texts such as Remington: The Science and Practice of Pharmacy, 20th ed, Lippincott Williams & Wilkins, pub!., 2000; and The Handbook of Pharmaceutical Excipients, 4.sup.th edit., eds. R. C. Rowe et al, APhA Publications, 2003.

The vaccine of the invention will be administered in a "therapeutically effective amount", which refers to an amount of an active ingredient, e.g., an agent according to the invention, sufficient to effect beneficial or desired results when administered to a subject or patient. An effective amount can be administered in one or more administrations, applications or dosages. A therapeutically effective amount of a composition according to the invention may be readily determined by one of ordinary skill in the art. In the context of this invention, a "therapeutically effective amount" is one that produces an objectively measured change in one or more parameters associated with Infectious Bronchitis condition sufficient to effect beneficial or desired results. An effective amount can be administered in one or more administrations. For purposes of this invention, an effective amount of drug, compound, or pharmaceutical composition is an amount sufficient to reduce the incidence of Infectious Bronchitis. As used herein, the term "therapeutic" encompasses the full spectrum of treatments for a disease, condition or disorder. A "therapeutic" agent of the invention may act in a manner that is prophylactic or preventive, including those that incorporate procedures designed to target animals that can be identified as being at risk (pharmacogenetics); or in a manner that is ameliorative or curative in nature; or may act to slow the rate or extent of the progression of at least one symptom of a disease or disorder being treated.

The present invention also relates to a method for producing such a vaccine which comprises the step of infecting cells, for example Vero cells, with a viral particle comprising a modified protein as defined in connection with the first aspect of the invention.

Vaccination Method

The coronavirus of the present invention may be used to treat and/or prevent a disease.

To "treat" means to administer the vaccine to a subject having an existing disease in order to lessen, reduce or improve at least one symptom associated with the disease and/or to slow down, reduce or block the progression of the disease.

To "prevent" means to administer the vaccine to a subject who has not yet contracted the disease and/or who is not showing any symptoms of the disease to prevent or impair the cause of the disease (e.g. infection) or to reduce or prevent development of at least one symptom associated with the disease.

The disease may be any disease caused by a coronavirus, such as a respiratory disease and and/or gastroenteritis in humans and hepatitis, gastroenteritis, encephalitis, or a respiratory disease in other animals.

The disease may be infectious bronchitis (IB); Porcine epidemic diarrhoea; Transmissible gastroenteritis; Mouse hepatitis virus; Porcine haemagglutinating encephalomyelitis; Severe acute respiratory syndrome (SARS); or Bluecomb disease.

The disease may be infectious bronchitis.

The vaccine may be administered to hatched chicks or chickens, for example by eye drop or intranasal administration. Although accurate, these methods can be expensive e.g. for large broiler flocks. Alternatives include spray inoculation or administration to drinking water but it can be difficult to ensure uniform vaccine application using such methods.

The vaccine may be provided in a form suitable for its administration, such as an eye-dropper for intra-ocular use.

The vaccine may be administered by in ovo inoculation, for example by injection of embryonated eggs. In ovo vaccination has the advantage that it provides an early stage resistance to the disease. It also facilitates the administration of a uniform dose per subject, unlike spray inoculation and administration via drinking water.

The vaccine may be administered to any suitable compartment of the egg, including allantoic fluid, yolk sac, amnion, air cell or embryo. It may be administered below the shell (aircell) membrane and chorioallantoic membrane.

Usually the vaccine is injected into embryonated eggs during late stages of embryonic development, generally during the final quarter of the incubation period, such as 3-4 days prior to hatch. In chickens, the vaccine may be administered between day 15-19 of the 21-day incubation period, for example at day 17 or 18.

The process can be automated using a robotic injection process, such as those described in WO 2004/078203.

The vaccine may be administered together with one or more other vaccines, for example, vaccines for other diseases, such as Newcastle disease virus (NDV). The present invention also provides a vaccine composition comprising a vaccine according to the invention together with one or more other vaccine(s). The present invention also provides a kit comprising a vaccine according to the invention together with one or more other vaccine(s) for separate, sequential or simultaneous administration.

The vaccine or vaccine composition of the invention may be used to treat a human, animal or avian subject. For example, the subject may be a chick, chicken or mouse (such as a laboratory mouse, e.g. transgenic mouse).

Typically, a physician or veterinarian will determine the actual dosage which will be most suitable for an individual subject or group of subjects and it will vary with the age, weight and response of the particular subject(s).

The composition may optionally comprise a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as (or in addition to) the carrier, excipient or diluent, any suitable binder(s), lubricant(s), suspending agent(s), coating agent(s), solubilising agent(s), and other carrier agents that may aid or increase the delivery or immunogenicity of the virus.

Definitions of terms appear throughout the specification. Before the exemplary embodiments are described in more detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise.

Thus, for example, reference to "an enzyme" includes a plurality of such candidate agents and equivalents thereof known to those skilled in the art, and so forth.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The invention will now be further described by way of Examples, which are meant to serve to assist one of ordinary skill in the art in carrying out the invention and are not intended in any way to limit the scope of the invention.

EXAMPLES

Example 1—Generation of an IBV Reverse Genetics System Based on M41-CK

A M41-CK full-length cDNA was produced by replacement of the Beaudette cDNA in the Vaccinia virus reverse genetics system previously described in PCT/GB2010/001293 (herein incorporated by reference) with synthetic cDNA derived from the M41 consensus sequence.

The IBV cDNA within recombinant Vaccinia virus (rVV) rVV-BeauR-Rep-M41 Struct described in Armesto, Cavanagh and Britton (2009). PLoS ONE 4(10): e7384. doi:10.1371/journal.pone.0007384, which consisted of the replicase derived from IBV Beaudette strain and the structural and accessory genes and 3' UTR from IBV M41-CK, was further modified by replacement of the Beaudette 5' UTR-Nsp2-Nsp3 sequence with the corresponding sequence from IBV M41-CK. The resulting IBV cDNA consisted of 5' UTR-Nsp2-Nsp3 from M41, Nsp4-Nsp16 from Beaudette and the structural and accessory genes and 3' UTR from M41. This cDNA was further modified by the deletion of the Beaudette Nsp4-Nsp16 sequence. The resulting cDNA, lacking Nsp4-16, was modified in four further steps in which the deleted Nsps were sequentially replaced with the corresponding sequences from M41-CK, the replacement cDNAs represented M41-CK Nsp4-8, Nsp9-12, Nsp12-14 and finally Nsp15-16. Each replacement cDNA contained approx. 500 nucleotides at the 5' end corresponding to the 3' most M41 sequence previously inserted and approx. 500 nucleotides at the 3' end corresponding to the M41 S gene sequence. This allowed insertion of the M41 cDNA sequence by homologous recombination and sequential addition of contiguous M41 replicase gene sequence. The synthetic cDNAs containing the M41-derived Nsp sequences were added by homologous recombination utilising the inventor's previous described transient dominant selection (TDS) system (see PCT/GB2010/001293).

Example 2—Determining the Pathogenicity of Recombinant M41 Viruses

Three recombinants were produced using the reverse genetics system described in Example 1. These recombinants were named rIBV M41K-S-ADRP, rIBV M41K-A-ADRP and rIBV M41K-del3ab.

Figure 2:
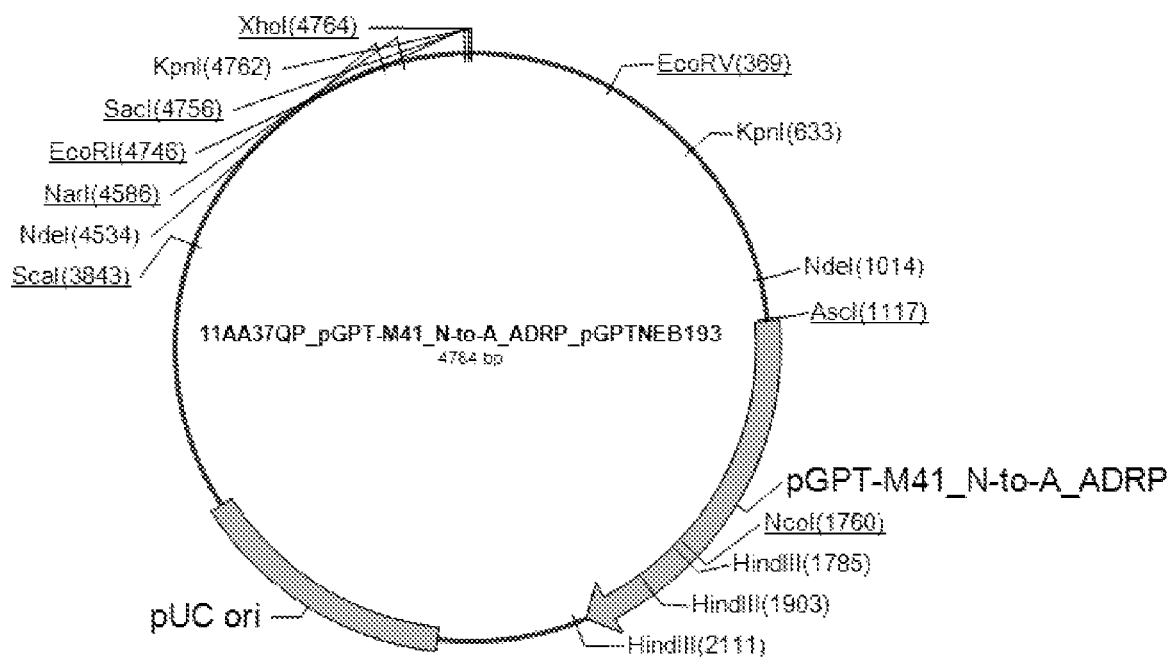
FIG. 2—plasmid used to produce rIBV M41K-A-ADRP.
Figure 3:
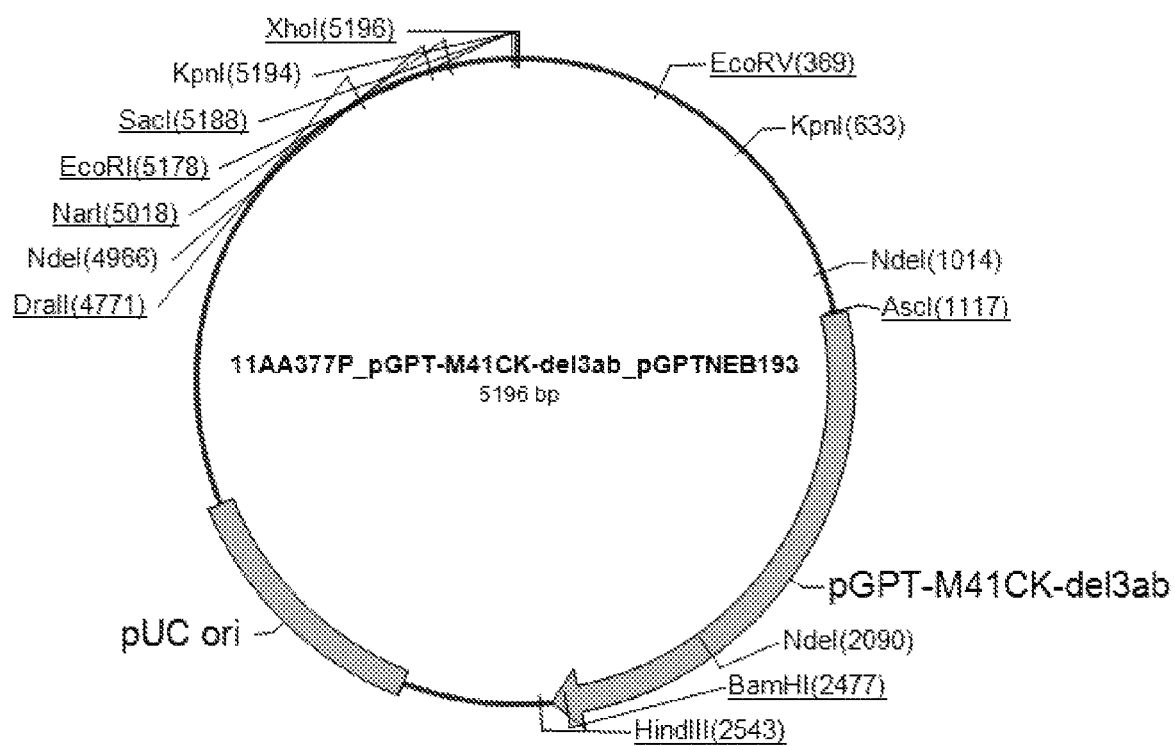
FIG. 3—plasmid used to produce rIBV M41K-del3ab.
Figure 7:
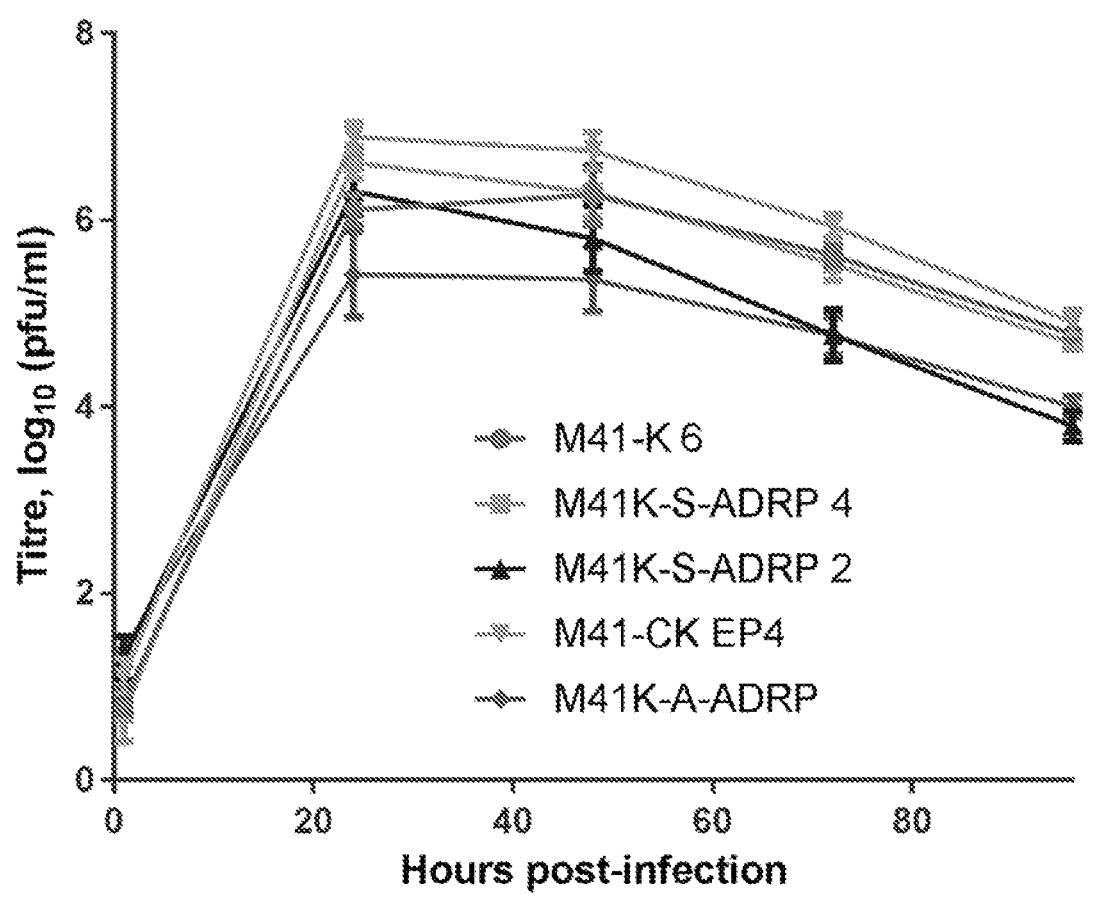
Figure 8:
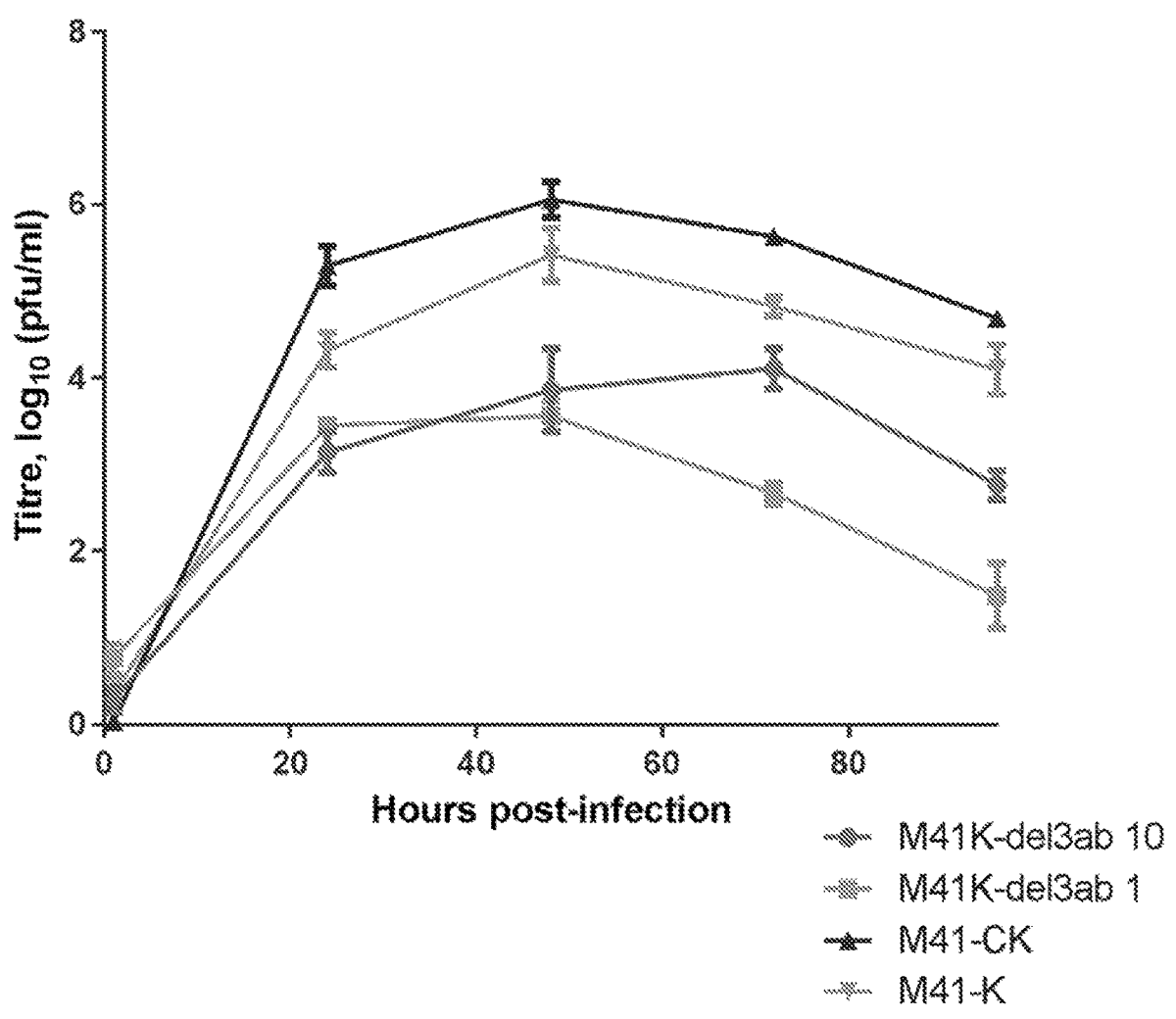

The three recombinants were shown to grow in a similar manner in chicken kidney cells as wild-type M41-CK/M41-K (FIGS. 7 and 8).

rIBV M41K-S-ADRP has a mutation at nucleotide position G3685A in the adenosine diphosphate-ribose-1'-phosphatase (ADRP) region of nsp-3 resulting in an amino acid mutation from G to S. This mutation was introduced into the rVV containing M41-K using the plasmid shown in FIG. 1.

rIBV M41K-A-ADRP has two mutations at nucleotide positions A3664G and A3665C in the ADRP region of nsp-3 resulting in an amino acid mutation from N to A. This mutation was introduced into the rVV containing M41-K using the plasmid shown in FIG. 2.

rIBV M41K-del3ab has a deletion from nucleotide position 23867 to 24214 in gene 3 resulting in a lack of accessory proteins 3a and 3b. This region was deleted from the rVV containing M41-K using the plasmid shown in FIG. 3.

Figure 4A:
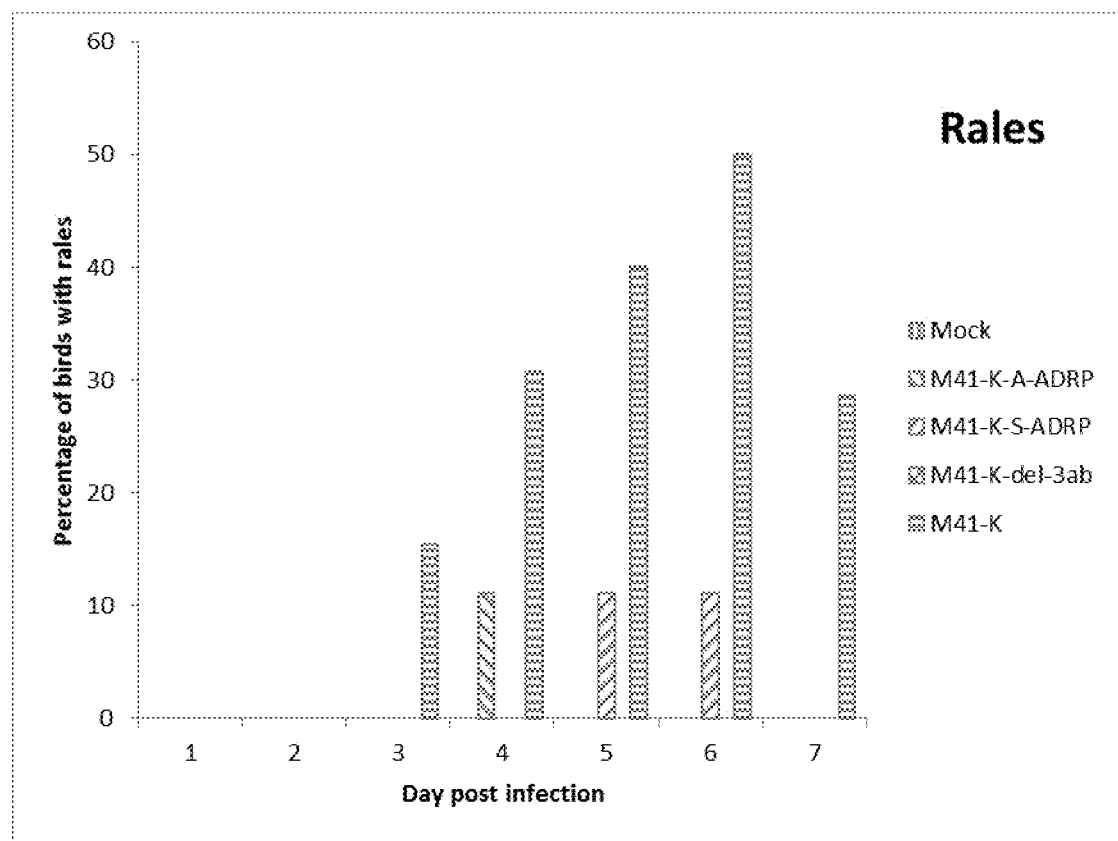
Figure 4B:
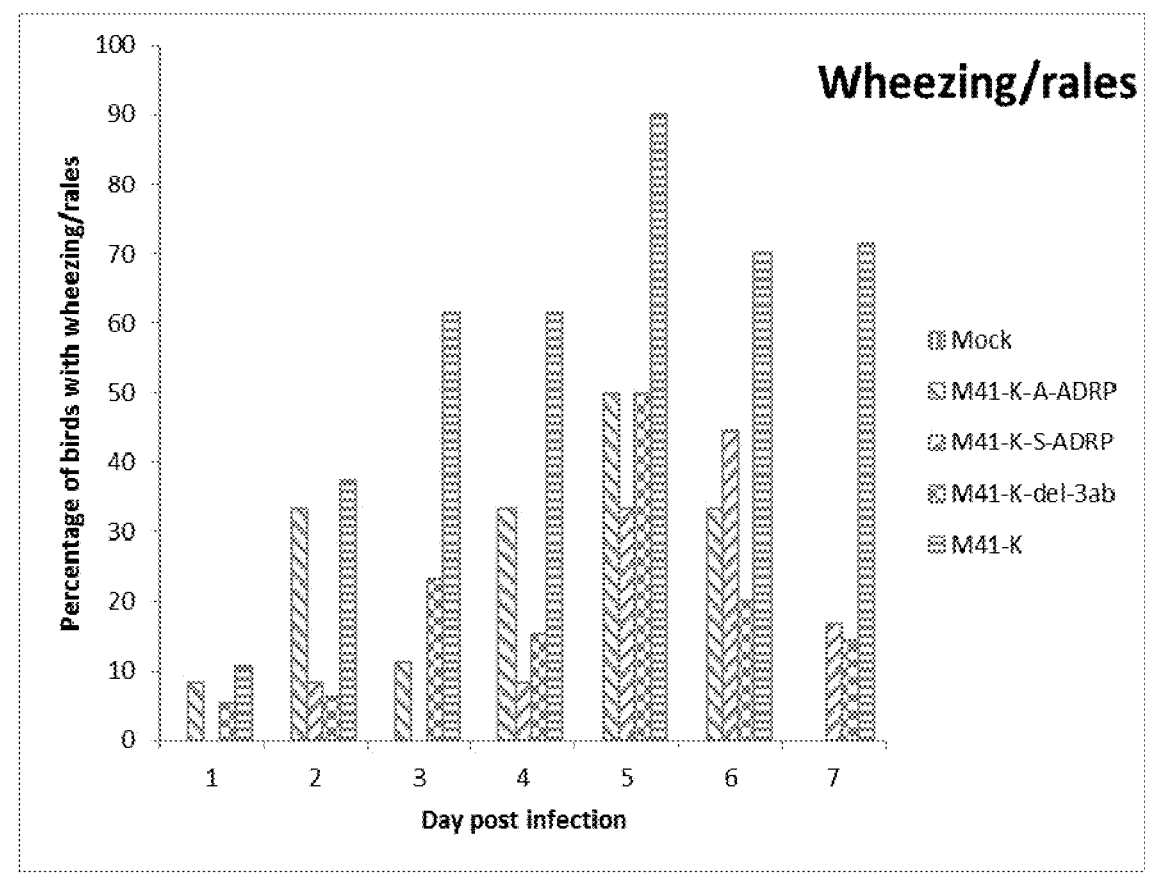
Figure 4C:
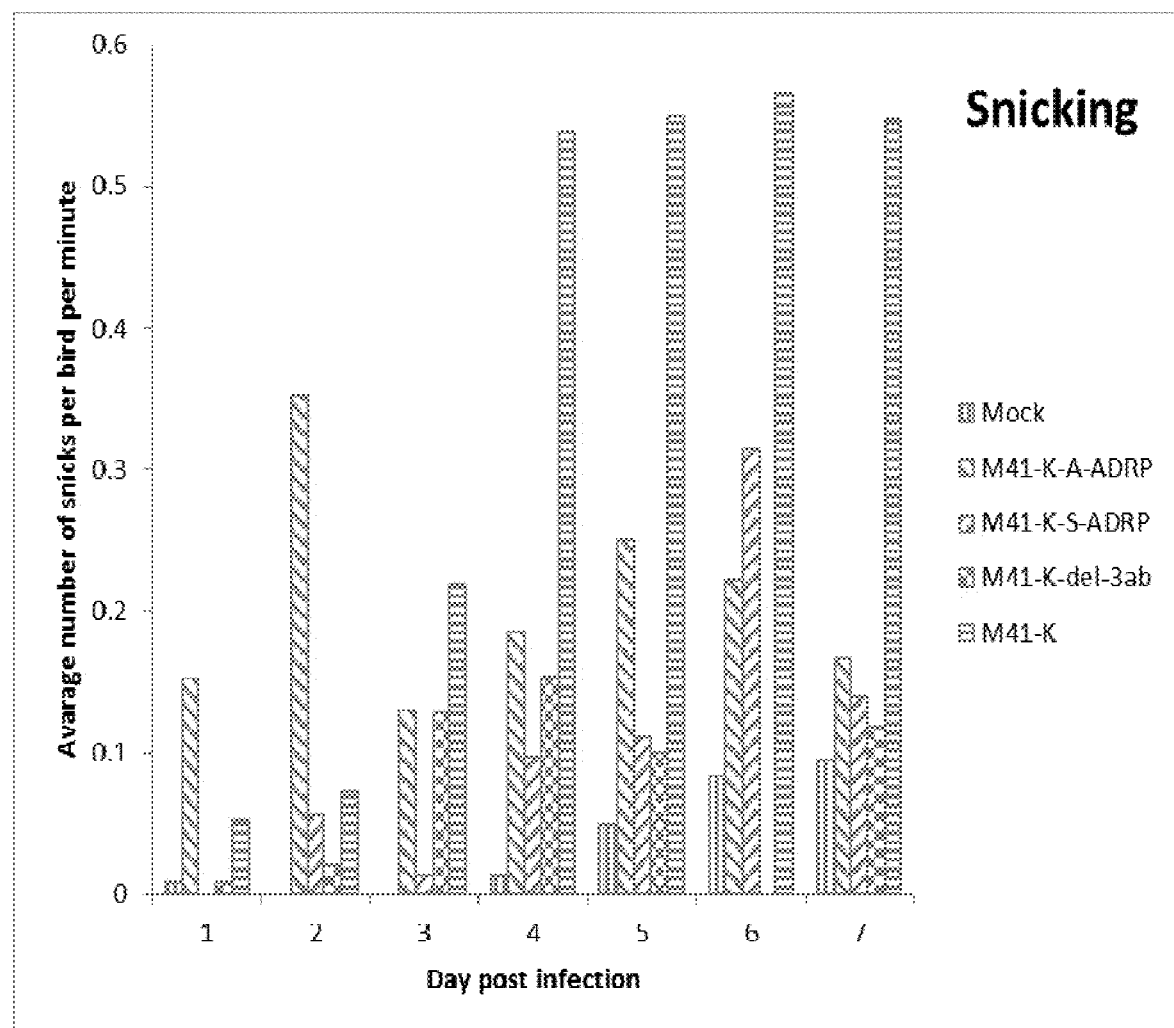
Figure 4D:
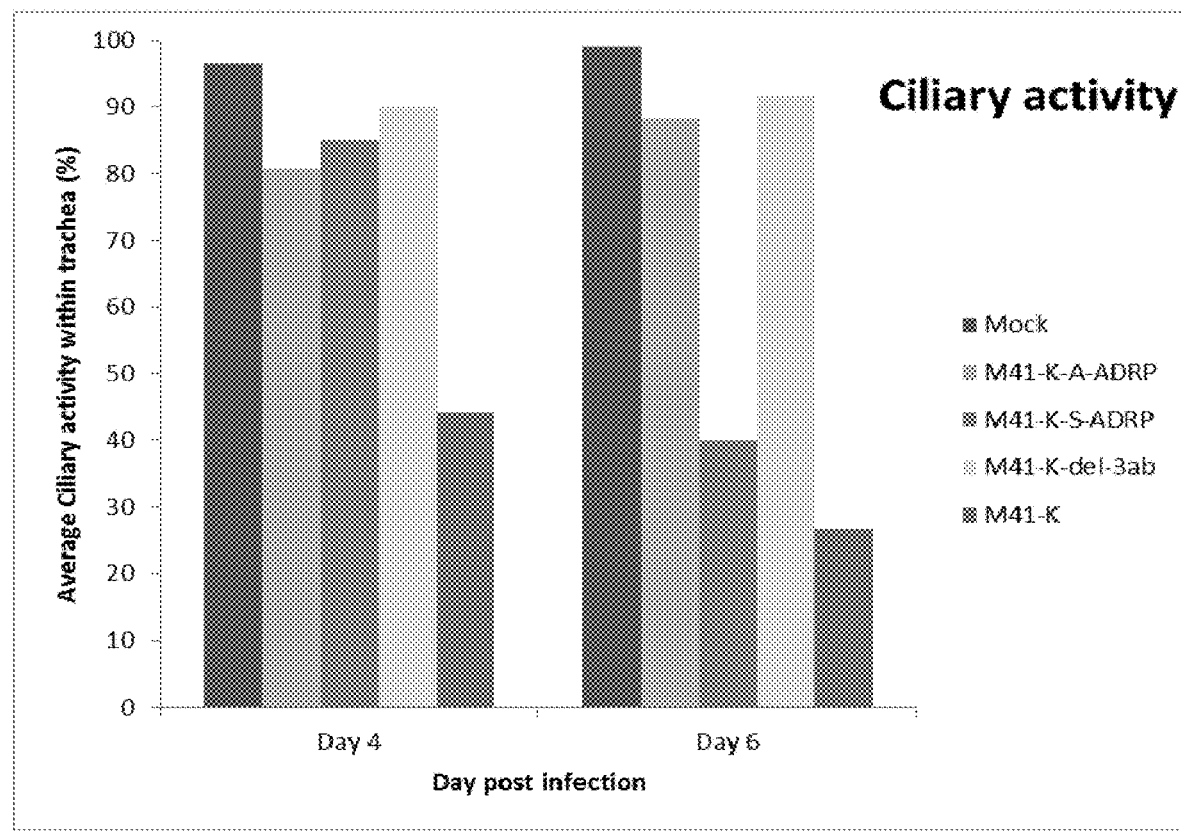

The three recombinant viruses were used to infect 8-day-old specific pathogen free (SPF) chicks by ocular and nasal inoculation to test them for pathogenicity, as observed by clinical signs on a daily basis 3-7 days post-infection and for ciliary activity days 4 and 6 post-infection. Loss of ciliary activity is a well-established method for determining the pathogenicity of IBV. Each of these recombinants were found to be less pathogenic than the parental virus M41-CK as shown in FIGS. 4-6.

Example 3—Vaccination/Challenge Study with M41-R

Candidate vaccine viruses are tested in studies in which fertilized chicken eggs are vaccinated in ovo at 19 days embryonation and in which the hatchability of the inoculated eggs is determined. The clinical health of the chickens is investigated and the chickens are challenged at 21 days of age with a virulent IB M41 challenge virus at $10^{3.65}$ EID$_{50}$ per dose.

Clinical signs are investigated after challenge protection by the vaccine and a ciliostasis test is performed at 5 days after challenge to investigate the effect of the challenge viruses on movement of the cilia and protection by the vaccine against ciliostasis (inhibition of cilia movement).

TABLE 3

| Treatment | Eggs | At hatch | Between hatch and challenge | Challenge | End of study |
|---|---|---|---|---|---|
| Saline | MDA⁻ | Determine hatch percentages | Clinical examination of birds | Chickens at age of 21 days | 5 days post challenge a ciliostasis test will be done |
| IB M41-K-A-ADRP | MDA⁻ | | | | |
| IB M41-K-S-ADRP | MDA⁻ | | | | |
| IB M41-K-3ab | MDA⁻ | | | | |

In ovo vaccination of 19 days embryonated eggs was performed by hand with needles of the same size as the automatic equipment.
After housing the different treatment groups are housed in separate units.
The clinical health of the chickens is examined daily.
After the challenge the clinical health of the chickens will be examined daily.

Results of Hatchability Study

SPF broiler eggs were incubated according to routine incubation procedures. At 19 days incubation 6 groups of 30 eggs were inoculated with $10^4$ EID$^{50}$ per dose of the IB vaccine strains IB M41-K-A-ADRP, IB M41-K-S-ADRP and IB M41-K-3ab. Another group of 30 eggs was inoculated with a placebo, i.e. PBS. At 21 days incubation the eggs hatched and the following results were obtained:

PBS 87% (26/30) hatched, 1 chick died after hatching and 3 eggs remained unopened and unmarked for embryo injection.

M41-K-A-ARDP 97% (29/30) hatched, 1 egg remained unopened and unmarked for embryo injection.

M41-K-S-ARDP 50% (15/30) hatched, 4 eggs remained unopened of which 1 was marked for embryo injection. The other eggs/animals were not viable.

M41-K-3ab 47% (18/30) hatched, 7 eggs remained unopened of which 3 were marked for embryo injection. The other eggs/animals were not viable.

IB M41-K-A-ADRP demonstrated good hatchability of inoculated eggs and so is considered suitable as a vaccine for in ovo vaccination. This strain will be tested for efficacy in a challenge test as detailed above.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, virology or related fields are intended to be within the scope of the following claims.

The invention claimed is:

1. A vaccine for in ovo administration, comprising a live, attenuated infectious bronchitis virus (IBV) comprising a mutation in the non-structural protein 3 (nsp-3) gene, wherein the nsp-3 gene encodes a protein comprising one or more amino acid mutations compared to the nsp-3 sequence shown as SEQ ID NO: 6, wherein the one or more amino acid mutations comprise Asn (N) to Ala (A) at the position corresponding to position 373 of SEQ ID NO: 6, wherein said attenuated IBV has reduced pathogenicity compared to a corresponding wild-type IBV which comprises a nsp-3 protein comprising a sequence shown as SEQ ID NO: 6.

2. The vaccine according to claim 1 wherein the nsp-3 gene comprises one or more nucleotide substitutions compared to the nsp-3 nucleotide sequence shown as SEQ ID NO: 5, wherein the one or more nucleotide substitutions comprise A to G at the position corresponding to nucleotide position 1116 and A to C at the position corresponding to nucleotide position 1117 of the nsp-3 nucleotide sequence shown as SEQ ID NO: 5.

3. The vaccine according to claim 1 wherein the IBV is M41.

4. The vaccine according to claim 3, wherein the IBV comprises an S protein wherein at least part of which is from an IBV serotype other than M41.

5. The vaccine according to claim 4, wherein the S protein comprises the S1 subunit from an IBV serotype other than M41.

6. The vaccine according to claim 1 which has reduced pathogenicity compared to a wild-type coronavirus, such that when the virus is administered to an embryonated egg, it is capable of replicating without being pathogenic to the embryo.

7. A method for treating and/or preventing a disease in a subject which comprises the step of administering a vaccine according to claim 1 to the subject.

8. The method according to claim 7 wherein the disease is infectious bronchitis (IB).

9. The method according to claim 8 wherein the vaccination is in ovo vaccination.

* * * * *

SEQUENCE LISTING

<160> NUMBER OF SEQ ID NOS: 6

<210> SEQ ID NO 1

<211> LENGTH: 27500
<212> TYPE: DNA
<213> ORGANISM: Avian infectious bronchitis virus

<400> SEQUENCE: 1

```
acttaagata gatattaata tatatctatc acactagcct tgcgctagat ttccaactta      60
acaaaacgga cttaaatacc tacagctggt cctcataggt gttccattgc agtgcacttt     120
agtgccctgg atggcacctg gccacctgtc aggttttgt tattaaaatc ttattgttgc      180
tggtatcact gcttgttttg ccgtgtctca ctttatacat ccgttgcttg ggctacctag     240
tatccagcgt cctacgggcg ccgtggctgg ttcgagtgcg aagaacctct ggttcatcta     300
gcggtaggcg ggtgtgtgga agtagcactt cagacgtacc ggttctgttg tgtgaaatac     360
ggggtcacct cccccacat acctctaagg gcttttgagc ctagcgttgg gctacgttct      420
cgcataaggt cggctatacg acgtttgtag ggggtagtgc caaacaaccc ctgaggtgac     480
aggttctggt ggtgtttagt gagcagacat acaatagaca gtgacaacat ggcttcaagc     540
ctaaaacagg gagtatctcc caaactaagg gatgtcattc ttgtatccaa agacattcct     600
gaacaacttt gtgacgcttt gttttttctat acgtcacaca accctaagga ttacgctgat     660
gcttttgcag ttaggcagaa gtttgatcgt aatctgcaga ctgggaaaca gttcaaatt     720
gaaactgtgt gtggtctctt cctcttgaag ggagttgaca aaataacacc tggcgtccca     780
gcaaaagtct taaaagccac ttctaagttg gcagatttag aagacatctt tggtgtctct     840
cccttttgcaa gaaaatatcg tgaacttttg aagacagcat gccagtggtc tcttactgta     900
gaaacactgg atgctcgtgc acaaactctt gatgaaattt ttgaccctac tgaaatactt     960
tggcttcagg tggcagcaaa atccaagtt tcggctatgg cgatgcgcag gcttgttgga    1020
gaagtaactg caaagtcat ggatgctttg ggctcaaata tgagtgctct tttccagatt     1080
tttaaacaac aaatagtcag aattttttcaa aaagcgctgg ctattttga gaatgtgagt     1140
gaattaccac agcgtattgc agcacttaag atggcttttg ctaagtgtgc caagtccatt    1200
actgttgtgg ttatggagag gactctagtt gttagagagt cgcaggaac ttgtcttgca     1260
agcattaatg gtgctgttgc aaaattcttt gaagaactcc caaatggttt catgggtgct    1320
aaaattttca ctacacttgc cttctttagg gaggctgcag tgaaaattgt ggataacata    1380
ccaaatgcac cgagaggcac taagggttt gaagtcgttg gtaatgccaa aggtacacaa    1440
gttgttgtgc gtggcatgcg aaatgactta acactgcttg accaaaaagc tgaaattcct    1500
gtggagtcag aaggttggtc tgcaattttg ggtggacatc tttgctatgt ctttaagagt    1560
ggtgatcgct tttacgcggc acctctttca ggaaattttg cattgcatga tgtgcattgt    1620
tgtgagcgtg ttgtctgtct ttctgatggt gtaacaccgg agataaatga tggacttatt    1680
cttgcagcaa tctactcttc ttttagtgtc gcagaacttg tggcagccat taaaaggggt    1740
gaaccattta gtttctggg tcataaattt gtgtatgcaa aggatgcagc agtttctttt    1800
acattagcga aggctgctac tattgcagat gtttttgaagc tgtttcaatc agcgcgtgtg    1860
aaagtagaag atgtttggtc ttcacttact gaaaagtctt ttgaattctg gaggcttgca    1920
tatgaaaaag tcgtaatct cgaagaattt gttaagactt gttttttgtaa ggctcaaatg    1980
gcgattgtga ttttagcgac agtgcttgga gagggcattt ggcatcttgt tcgcaagtc    2040
atctataaag taggtggtct ttttactaaa gttgttgact tttgtgaaaa atattggaaa    2100
ggttttgtg cacagttgaa aagagctaag ctcattgtca ctgaaccct ctgtgttttg     2160
aaaggagttg cacagcattg ttttcaacta ttgctggatg caatacagtt tatgtataaa    2220
```

```
agttttaaga agtgtgcact tggtagaatc catggagact tgctcttctg gaaaggaggt    2280
gtgcacaaaa ttattcaaga gggcgatgaa atttggtttg acgccattga tagtattgat    2340
gttgaagatc tgggtgttgt tcaagaaaaa ttgattgatt ttgatgtttg tgataatgtg    2400
acacttccag agaaccaacc cggtcatatg gttcaaatcg aggatgacgg aaagaactac    2460
atgttcttcc gcttcaaaaa ggatgagaac atttattata caccaatgtc acagcttggt    2520
gctattaatg tggtttgcaa agcaggcggt aaaactgtca cctttggaga aactactgtg    2580
caagaaatac caccacctga tgttgtgttt attaaggtta gcattgagtg ttgtggtgaa    2640
ccatggaata caatcttcaa aaaggcttat aaggagccca ttgaagtaga cagacctc     2700 acagttgaac aattgctctc tgtggtctat gagaaaatgt gtgatgatct caagctgttt    2760
ccggaggctc cagaaccacc accatttgag aatgtcacac ttgttgataa gaatggtaaa    2820
gatttggatt gcataaaatc atgccatctg atctatcgtg attatgagag cgatgatgac    2880
atcgaggaag aagatgcaga agaatgtgac acggattcag gtgatgctga ggagtgtgac    2940
actaattcag aatgtgaaga agaagatgag gatactaaag tgttggctct tatacaagac    3000
ccggcaagta acaaatatcc tctgcctctt gatgatgatt atagcgtcta caatggatgt    3060
attgttcata aggacgctct cgatgttgtg aatttaccat ctggtgaaga aacctttgtt    3120
gtcaataact gctttgaagg ggctgttaaa gctcttccgc agaaagttat tgatgttcta    3180
ggtgactggg gtgaggctgt tgatgcgcaa gaacaattgt gtcaacaaga atcaactcgg    3240
gtcatatctg agaaatcagt tgagggtttt actggtagtt gtgatgcaat ggctgaacaa    3300
gctattgttg aagagcagga atagtacct gttgttgaac aaagtcagga tgtagttgtt    3360
tttacacctg cagacctaga agttgttaaa gaaacagcag aagaggttga tgagtttatt    3420
ctcatttctg ctgtccctaa agaagaagtt gtgtctcagg agaaagagga gccacaggtt    3480
gagcaagagc ctaccctagt tgttaaagca caacgtgaga agaaggctaa aaagttcaaa    3540
gttaaaccag ctacatgtga aaacccaaa ttttggagt acaaacatg tgtgggtgat     3600 ttggctgttg taattgccaa agcattggat gagtttaaag agttctgcat tgtaaacgct    3660
gcaaatgagc acatgtcgca tggtggtggc gttgcaaagg caattgcaga cttttgtgga    3720
ccggactttg ttgaatattg cgcggactat gttaagaaac atggtccaca gcaaaaactt    3780
gtcacacctt catttgttaa aggcattcaa tgtgtgaata tgttgtagg acctcgccat    3840 ggagacagca acttgcgtga agcttgtt gctgcttaca agagtgttct tgtaggtgga    3900
gtggttaact atgttgtgcc agttctctca tcagggattt ttggtgtaga ttttaaaata    3960
tcaatagatg ctatgcgcga agcttttaaa ggttgtgcca tacgcgttct tttattttct    4020
ctgagtcaag aacacatcga ttatttcgat gcaacttgta agcagaagac aatttatctt    4080
acggaggatg gtgttaaata ccgctctgtt gttttaaaac ctggtgattc tttgggtcaa    4140
tttggacagg tttttgcaag aaataaggta gtcttttcgg ctgatgatgt tgaggataaa    4200
gaaatcctct ttatacccac aactgacaag actattcttg aatattatgg tttagatgcg    4260
caaaagtatg taacatattt gcaaacgctt gcgcagaaat gggatgttca atatagagac    4320
aattttgtta tattagagtg gcgtgacgga aattgctgga ttagttcagc aatagttctc    4380
cttcaagctg ctaaaattag atttaaaggt tttcttgcag aagcatgggc taaactgttg    4440
ggtggagatc ctacagactt tgttgcctgg tgttatgcaa gttgcaatgc taaagtaggt    4500
gatttttcag atgctaattg gctttggcc aatttagcag aacattttga cgcagattac    4560
```

```
acaaatgcac ttcttaagaa gtgtgtgtcg tgcaattgtg gtgttaagag ttatgaactt    4620
aggggtcttg aagcctgtat tcagccagtt cgagcaccta atcttctaca ttttaaaacg    4680
caatattcaa attgcccaac ctgtggtgca agtagtacgg atgaagtaat agaagcttca    4740
ttaccgtact tattgctttt tgctactgat ggtcctgcta cagttgattg tgatgaaaat    4800
gctgtaggga ctgttgtttt cattggctct actaatagtg gccattgtta tacacaagcc    4860
gatggtaagg cttttgacaa tcttgctaag gatagaaaat ttggaaggaa gtcgccttac    4920
attacagcaa tgtatacacg ttttttctctt aggagtgaaa atcccctact tgttgttgaa    4980
catagtaagg gtaaagctaa agtagtaaaa gaagatgttt ctaaccttgc tactagttct    5040
aaagccagtt ttgacgatct tactgacttt gaacagtggt atgatagcaa catctatgag    5100
agtcttaaag tgcaggagac acctgataat cttgatgaat atgtgtcatt tacgacaaag    5160
gaagattcta agttgccact gacacttaaa gttagaggta tcaaatcagt tgttgactttt    5220 aggtctaagg atggttttac ttataagtta acacctgata ctgatgaaaa ttcaaaaaca    5280
ccagtctact acccagtctt ggattctatt agtcttaggg caatatgggt tgaaggcagt    5340
gctaattttg ttgttgggca tccaaattat tatagtaagt ctctccgaat tcccacgttt    5400
tgggaaaatg ccgagagctt tgttaaaatg ggttataaaa ttgatggtgt aactatgggc    5460
ctttggcgtg cagaacacct taataaacct aatttggaga aattttttaa cattgctaag    5520
aaagctattg ttgatctag tgttgttact acgcagtgtg gtaaaatact agttaaagca    5580
gctacatacg ttgccgataa agtaggtgat ggtgtagttc gcaatattac agatagaatt    5640
aagggtcttt gtggattcac acgtggccat tttgaaaaga aaatgtccct acaatttcta    5700
aagacacttg tgttctttttt cttttatttc ttaaaggcta gtgctaagag tttagtttct    5760
agctataaga ttgtgttatg taaggtggtg tttgctacct tacttatagt gtggtttata    5820
tacacaagta atccagtagt gtttactgga atacgtgtgc tagacttcct atttgaaggt    5880
tctttatgtg gtcccttataa tgactacggt aaagattctt ttgatgtgtt acgctattgt    5940
gcaggtgatt ttacttgtcg tgtgtgttta catgatagag attcacttca tctgtacaaa    6000
catgcttata gcgtagaaca aatttataag gatgcagctt ctggcattaa ctttaattgg    6060
aattggcttt atttggtctt tctaatatta tttgttaagc cagtggcagg ttttgttatt    6120
atttgttatt gtgttaagta tttggtattg agttcaactg tgttgcaaac tggtgtaggt    6180
tttctagatt ggtttgtaaa aacagttttt acccatttta attttatggg agcgggattt    6240
tatttctggc tcttttacaa gatatacgta caagtgcatc atatattgta ctgtaaggat    6300
gtaacatgtg aagtgtgcaa gagagttgca cgcagcaaca ggcaagaggt tagcgttgta    6360
gttggtggac gcaagcaaat agtgcatgtt tacactaatt ctggctataa ctttttgtaag    6420 agacataatt ggtattgtag aaattgtgat gattatggtc accaaaatac atttatgtcc    6480
cctgaagttg ctggcgagct ttctgaaaag cttaagcgcc atgttaaacc tacagcatat    6540
gcttaccacg ttgtgtatga ggcatgcgtg gttgatgatt ttgttaattt aaaatataag    6600
gctgcaattc ctggtaagga taatgcatct tctgctgtta agtgtttcag tgttacagat    6660
ttttttaaga agctgttttt tcttaaggag gcattgaaat gtgaacaaat atctaatgat    6720
ggttttatag tgtgtaatac acagagtgcg catgcactag aggaagcaaa gaatgcagcc    6780
gtctattatg cgcaatatct gtgtaagcca atacttatac ttgaccaggc actttatgag    6840
caattaatag tagagcctgt gtctaagagt gttatagata agtgtgtag cattttgtct    6900 aatataatat ctgtagatac tgcagcttta aattataagg caggcacact tcgtgatgct    6960
```

```
ctgctttcta ttactaaaga cgaagaagcc gtagatatgg ctatcttctg ccacaatcat    7020
gaagtggaat acactggtga cggttttact aatgtgatac cgtcatatgg tatggacact    7080
gataagttga cacctcgtga tagagggttt ttgataaatg cagatgcttc tattgctaat    7140
ttaagagtca aaaatgctcc tccggtagta tggaagtttt ctgatcttat taaattgtct    7200
gacagttgcc ttaaatattt aatttcagct actgtcaagt caggaggtcg tttctttata    7260
acaaagtctg gtgctaaaca agttatttct tgtcataccc agaaactgtt ggtagagaaa    7320
aaggcaggtg gtgttattaa taacactttt aaatggttta tgagttgttt taaatggctt    7380
tttgtctttt atatactttt tacagcatgt tgtttgggtt actactatat ggagatgaat    7440
aaaagttttg ttcaccccat gtatgatgta aactccacac tgcatgttga agggttcaaa    7500
gttatagaca aaggtgttat tagagagatt tgtgtcagaag ataattgttt ctctaataag    7560
tttgttaatt ttgacgcctt ttggggtaaa tcatatgaaa ataataaaaa ctgtccaatt    7620
gttacagttg ttatagatgg tgacgggaca gtagctgttg gtgttcctgg ttttgtatca    7680
tgggttatgg atggtgttat gtttgtgcat atgacacaga ctgatcgtag accttggtac    7740
attcctacct ggtttaatag agaaattgtt ggttacactc aggattcaat tatcactgag    7800
ggtagttttt atacatctat agcattattt tctgctagat gtttatattt aacagccagc    7860
aatacacctc aattgtattg ttttaatggc gacaatgatg cacctggagc cttaccattt    7920
ggtagtatta ttcctcatag agtatacttc aacctaatg gtgttaggct tatagttcca    7980
caacaaatac tgcatacacc ctacatagtg aagtttgttt cagacagcta ttgtagaggt    8040
agtgtatgtg agtatactaa accaggttac tgtgtgtcac tagactccca atgggttttg    8100
tttaatgatg aatacattag taaacctggc gttttctgtg gttctactgt tagagaactt    8160
atgtttaata tggttagtac attctttact ggtgtcaacc ctaatatta tattcagcta    8220 gcaactatgt ttttaatact agttgttatt gtgttaattt ttgcaatggt tataaagttt    8280
caaggtgttt ttaaagctta tgcgaccatt gtgtttacaa taatgttagt ttgggttatt    8340
aatgcatttg ttttgtgtgt acatagttat aatagtgttt tagctgttat attattagta    8400
ctctattgct atgcatcatt ggttacaagt cgcaatactg ctataataat gcattgttgg    8460
cttgttttta cctttggttt aatagtaccc acatggttgg cttgttgcta tctgggattt    8520 attcttata tgtacacacc gttggttttc tggtgttacg gtactactaa aaatactcgt    8580
aagttgtatg atggcaacga gtttgttggt aattatgacc ttgctgcgaa gagcacttt    8640 gttattcgtg gtactgaatt tgttaagctt acgaatgaga taggtgataa atttgaagcc    8700
tatctttctg cgtatgctag acttaaatac tattcaggca ctggtagtga gcaagattac    8760
ttgcaagctt gtcgtgcatg gttagcttat gctttggacc aatatagaaa tagtggtgtt    8820
gaggttgttt ataccccacc gcgttactct attggtgtta gtagactaca cgctggtttt    8880
aaaaaactag tttctcctag tagtgctgtt gagaagtgca ttgttagtgt ctcttataga    8940
ggcaataatc ttaatggact gtggctgggt gattctattt actgcccacg ccatgtgtta    9000 ggtaagtta gtggtgacca gtggggtgac gtactaaacc ttgctaataa tcatgagttt    9060
gaagttgtaa ctcaaaatgg tgttactttg aatgttgtca gcaggcggct taaaggagca    9120
gttttaattt tacaaactgc agttgccaat gctgaaactc taagtataaa gtttgttaaa    9180
gctaattgtg gtgatagttt cactatagct tgttcttatg gtgtacagt tataggactt    9240 taccctgtca ctatgcgttc taatggtact attagagcat ctttcctagc aggagcctgt    9300
```

```
ggctcagttg gttttaatat agaaaagggt gtagttaatt tcttttatat gcaccatctt      9360
gagttaccta atgcattaca cactggaact gacctaatgg gtgagtttta tggtggttat      9420
gtagatgaag aggttgcgca aagagtgcca ccagataatc tagttactaa caatattgta      9480
gcatggctct atgcggcaat tattagtgtt aaagaaagta gtttttcaca acctaaatgg      9540
ttggagagta ctactgtttc tattgaagat tacaataggt gggctagtga taatggtttt      9600
actccatttt ccactagtac tgctattact aaattaagtg ctataactgg ggttgatgtt      9660
tgtaaactcc ttcgcactat tatggtaaaa agtgctcaat ggggtagtga tcccatttta      9720
ggacaatata attttgaaga cgaattgaca ccagaatctg tatttaatca agttggtggt      9780
gttaggttac agtcttcttt tgtaagaaaa gctacatctt ggttttggag tagatgtgta      9840
ttagcttgct tcttgtttgt gttgtgtgct attgtcttat ttacggcagt gccacttaag      9900
ttttatgtac atgcagctgt tattttgttg atggctgtgc tctttatttc ttttactgtt      9960
aaacatgtta tggcatacat ggacacttt ctattgccta cattgattac agttattatt      10020
ggagtttgtg ctgaagtccc tttcatatac aatactctaa ttagtcaagt tgttatttc      10080 ttaagccaat ggtatgatcc tgtagtcttt gatactatgg taccatggat gttattgcca      10140
ttagtgttgt acactgcttt taagtgtgta caaggctgct atatgaattc tttcaatact      10200
tctttgttaa tgctgtatca gtttatgaag ttaggttttg ttatttacac ctcttcaaac      10260
actcttactg catatacaga aggtaattgg gagttattct ttgagttggt tcacactatt      10320
gtgttggcta atgttagtag taattcctta attggtttaa ttgttttaa gtgtgctaag      10380 tggattttat attattgcaa tgcaacatac tttaataatt atgtgttaat ggcagtcatg      10440
gttaatggca taggctggct ttgcacctgt tactttggat tgtattggtg ggttaataaa      10500 gttttttggtt taaccttagg taatacaat tttaaagttt cagtagatca atataggtat      10560
atgtgtttgc ataaggtaaa tccacctaaa actgtgtggg aggtctttac tacaaatata      10620
cttatacaag gaattggagg cgatcgtgtg ttgcctatag ctacagtgca atctaaattg      10680
agtgatgtaa agtgtacaac tgttgtttta atgcagcttt tgactaagct taatgttgaa      10740
gcaaattcaa aaatgcatgc ttatcttgtt gagttacaca ataaaatcct cgcatctgat      10800
gatgttggag agtgcatgga taatttattg gtatgctta taacactatt ttgtatagat      10860
tctactattg atttgggtga gtattgtgat gatatactta gaggtcaac tgtattacaa      10920 tcggttactc aagagttttc gcacataccc tcgtatgctg aatatgaaag agctaagagt      10980 attttatgaaa aggttttagc cgattctaaa aatggtggtg taacacagca agagcttgct      11040
gcatatcgta agctgccaa tattgcaaag tcagttttg atagagactt ggctgttcaa      11100
aagaagttag atagcatggc agaacgtgct atgacaacaa tgtataaaga ggcgcgtgta      11160
actgatagaa gagcaaaatt agtttcatca ttacatgcac tactttttc aatgcttaag      11220 aaaatagatt ctgagaagct taatgtctta tttgaccagg cgaatagtgg tgttgtaccc      11280
ctagcaactg ttccaattgt ttgtagtaat aagcttaccc ttgttatacc agacccagag      11340
acgtgggtca agtgtgtgga gggtgtgcat gttacatatt caacagttgt ttggaatata      11400
gactgtgtta ctgatgccga tggcacagag ttacaccca cttctacagg tagtggattg      11460
acttactgta aagtggtga taatatagca tggcctttaa aggttaactt gactaggaat      11520
gggcataata aggttgatgt tgccttgcaa aataatgagc ttatgcctca cggtgtaaag      11580
acaaaggctt gcgtagcagg tgtagatcaa gcacattgta gcgttgagtc taatgttat      11640 tatacaagta ttagtggcag ttcagttgta gctgctatta cctcttcaaa tcctaatctg      11700
```

```
aaagtagcct ctttttttgaa tgaggcaggt aatcagattt atgtagactt agacccacca   11760
tgtaaatttg gtatgaaagt gggtgataag gttgaagttg tttacctgta ttttataaaa   11820
aatacgaggt ctattgtaag aggtatggta cttggtgcta tatctaatgt tgttgtgtta   11880
caatctaaag gtcatgagac agaggaagtg gatgctgtag gcattctctc actttgttct   11940
tttgcagtag atcctgcgga tacatattgt aaatatgtgg cagcaggtaa tcaacctta   12000 ggtaactgtg ttaaaatgtt gacagtacat aatggtagtg ttttgcaat aacatcaaag   12060 ccaagtccaa ctccggatca ggattcttat ggaggagctt ctgtgtgtct ttattgtaga   12120
gcacatatag cacaccctgg cggagcagga aatttagatg gacgctgtca atttaaaggt   12180
tcttttgtgc aaataccta tacggagaaa gatcctgttg gattctgtct acgtaacaag   12240
gtttgcactg tttgtcagtg ttggattggt tatggatgtc agtgtgattc acttagacaa   12300
cctaaacctt ctgttcagtc agttgctgtt gcatctggtt ttgataagaa ttatttaaac   12360
gggtacgggg tagcagtgag gctcggctga taccccctagc taatgatgt gaccccgatg   12420 ttgtaaagcg agcctttgat gtttgtaata aggaatcagc cggtatgttt caaaatttga   12480
agcgtaactg tgcacgattc caagaagtac gtgatactga agatggaaat cttgagtatt   12540
gtgattctta ttttgtggtt aaacaaacca ctcctagtaa ttatgaacat gagaaagctt   12600
gttatgaaga cttaaagtca gaagtaacag ctgatcatga tttctttgtg ttcaataaga   12660
acatttataa tattagtagg cagaggctta ctaagtatac tatgatggat ttttgctatg   12720
ctttgcggca ctttgaccca aaggattgcg aagttcttaa agaaatactt gtcacttatg   12780
gttgtataga agattatcac cctaagtggt ttgaagagaa taaggattgg tacgacccaa   12840
tagaaaaccc taaatattat gccatgttgg ctaaaatggg acctattgta cgacgtgctt   12900
tattgaatgc tattgagttc ggaaacctca tggttgaaaa aggttatgtt ggtgttatta   12960
cacttgataa ccaagatctt aatggcaaat tttatgattt tggtgatttt cagaagacag   13020
cgcctggtgc tggtgttcct gttttttgata cgtattattc ttacatgatg cccatcatag   13080
ccatgactga tgcgttggca cctgagaggt attttgaata tgatgtgcat aagggttata   13140
aatcttatga tctcctcaag tatgattata ctgaggagaa acaagatttg tttcagaagt   13200
actttaagta ttgggatcaa gagtatcacc ctaactgtcg cgactgtagt gatgacaggt   13260
gtttgataca ttgtgcaaac ttcaacatct tgttttctac acttgtaccg cagacttctt   13320
tcggtaattt tgtgtagaaag gttttttgttg atggtgtacc atttatagct acttgtggct   13380
atcattctaa ggaacttgg gttattatga atcaagataa caccatgtca ttttcaaaaa   13440
tgggtttgag tcaactcatg cagtttgttg gagatcctgc cttgttagtg gggacatcca   13500
ataaattagt ggatcttaga acgtcttgtt ttagtgtttg tgctttagcg tctggtatta   13560
ctcatcaaac ggtaaaacca ggtcacttta caaggatttt ctacgatttt gcagagaagg   13620
ctggtatgtt taaggaaggt tcttctatac cacttaaaca tttcttctac ccacagactg   13680
gtaatgctgc tataaacgat tatgattatt atcgttataa caggcctacc atgtttgata   13740
tacgtcaact tttatttttgt ttagaagtga cttctaaata ttttgaatgt tatgaaggcg   13800
gctgtatacc agcaagccaa gttgtagtta acaatttaga taagagtgca ggttatccgt   13860
tcaataagtt tggaaaggcc cgtctctatt atgaaatgag tctagaggag caggaccaac   13920
tctttgagag tacaaagaag aacgtcctgc ctactataac tcagatgaat ttaaaatatg   13980
ccatatccgc gaaaaataga gcgcgtacag tggcaggtgt gtctatcctt tctactatga   14040
```

```
ctaataggca gtttcatcag aagattctta agtctatagt caacactaga aacgctcctg    14100
tagttattgg aacaaccaag ttttatggcg gttgggataa catgttgaga aaccttattc    14160
agggtgttga agacccgatt cttatgggtt gggattatcc aaagtgtgat agagcaatgc    14220
ctaatttgtt gcgtatagca gcatctttag tactcgctcg taaacacact aattgttgta    14280
cttggtctga acgcgtttat aggttgtata atgaatgcgc tcaggtttta tctgaaactg    14340
tcttagctac aggtggtata tatgtgaaac ctggtggtac tagcagtgga gatgctacta    14400
ctgcttatgc aaacagtgtt ttcaacataa tacaagccac atctgctaat gttgcgcgtc    14460
ttttgagtgt tataacgcgt gatattgtat atgatgacat taagagcttg cagtatgaat    14520
tgtaccagca ggtttatagg cgagtcaatt ttgacccagc atttgttgaa aagttttatt    14580
cttatttgtg taagaatttc tcattgatga tcttgtctga cgacggtgtt gtttgttata    14640
acaacacatt agccaaacaa ggtcttgtag cagatatttc tggttttaga gaagttctct    14700
actatcagaa caatgttttt atggctgatt ctaaatgttg ggttgaacca gatttagaaa    14760
aaggcccaca tgaattttgt tcacagcaca caatgttagt ggaggttgat ggtgagccta    14820
gatacttgcc atatccagac ccatcacgta ttttgtgtgc atgtgttttt gtagatgatt    14880
tggataagac agaatctgtg ctgttatgg agcgttatat cgctcttgcc atagatgcgt    14940
acccactagt acatcatgaa aatgaggagt acaagaaggt attctttgtg cttctttcat    15000
acatcagaaa actctatcaa gagctttctc agaatatgct tatggactac tcttttgtaa    15060
tggatataga taagggtagt aaattttggg aacaggagtt ctatgaaaat atgtatagag    15120
cccctacaac attacagtct tgtggcgttt gtgtagtgtg taatagtcaa actatattgc    15180
gctgtggtaa ttgtattcgc aaaccatttt tgtgttgtaa gtgttgctat gaccatgtca    15240
tgcacacaga ccacaaaaat gttttgtcta taaatcctta catttgctca cagccaggtt    15300
gtggtgaagc agatgttact aaattgtacc tcggaggtat gtcatacttc tgcggtaatc    15360
ataaaccaaa gttatcaata ccgttagtat ctaatgtac agtgtttgga atttacaggg    15420
ctaattgtgc aggtagcgaa aatgttgatg attttaatca actagctact actaattggt    15480
ctactgtgga accttatatt ttggcaaatc gttgtgtaga ttcgttgaga cgcttttgct    15540
cagagacagt aaaagctaca gaagaattac ataagcaaca atttgctagt gcagaagtga    15600
gagaagtact ctcagatcgt gaattgattc tgtcttggga gccaggtaaa accaggcctc    15660
cattgaatag aaattatgtt ttcactggct ttcactttac tagaactagt aaagttcagc    15720
tcggtgattt tacatttgaa aaaggtgaag gtaaggacgt tgtctattat cgagcgacgt    15780
ctactgctaa attgtctgtt ggagacattt ttgttttaac ctcacacaat gttgtttctc    15840
ttatagcgcc aacgttgtgt cctcagcaaa ccttttctag gtttgtgaat ttaagaccta    15900
atgtgatggt acctgcgtgt tttgtaaata cattccatt gtaccattta gtaggcaagc    15960
agaagcgtac tacagtacaa ggccctcctg gcagtggtaa atcccatttt gctataggat    16020
tggcggctta ctttagtaac gcccgtgtcg ttttttactg catgctctcat gcagctgttg    16080
atgctttatg tgaaaaagct tttaagtttc ttaaagtaga tgattgcact cgtatagtac    16140
ctcaaaggac tactatcgat tgcttctcta gtttaaagc taatgacaca ggcaaaaagt    16200
acatttttag tactattaat gccttgccag aagttagttg tgacattctt ttggttgacg    16260
aggttagtat gttgaccaat tacgaattgt ctttattaa tggtaagata aactatcaat    16320
atgttgtgta tgtaggtgat cctgctcaat taccggcgcc tcgtacgttg cttaacggtt    16380
cactctctcc aaaggattat aatgttgtca caaaccttat ggtttgtgtt aaacctgaca    16440
```

```
ttttccttgc aaagtgttac cgttgtccta aagaaattgt agatactgtt tctactcttg  16500
tatatgatgg aaagtttatt gcaaataacc cggaatcacg tcagtgtttc aaggttatag  16560
ttaataatgg taattctgat gtaggacatg aaagtggctc agcctacaac ataactcaat  16620
tagaatttgt gaaagatttt gtctgtcgca ataaggaatg gcgggaagca acattcattt  16680
caccttataa tgctatgaac cagagagcct accgtatgct tggacttaat gttcagacag  16740
tagactcgtc tcaaggttcg gagtatgatt atgttatctt ttgtgttact gcagattcgc  16800
agcatgcact gaatattaac agattcaatg tagcgcttac aagagccaag cgtggtatac  16860
tagttgtcat gcgtcagcgt gatgaactat attcagctct taagtttata gagcttgata  16920
gtgtagcaag tctgcaaggt acaggcttgt ttaaaatttg caacaaagag tttagtggtg  16980
ttcacccagc ttatgcagtc acaactaagg ctcttgctgc aacttataaa gttaatgatg  17040
aacttgctgc acttgttaac gtggaagctg gttcagaaat aacatataaa catcttattt  17100
ctttgttagg gttaagatg agtgttaatg ttgaaggctg ccacaacatg tttataacac  17160
gtgatgaggc tatccgcaac gtaagaggtt gggtaggttt tgatgtagaa gcaacacatg  17220
cttgcggtac taacattggt actaacctgc ctttccaagt aggtttctct actggtgcag  17280
actttgtagt tacgcctgag ggacttgtag atacttcaat aggcaataat tttgagcctg  17340
tgaattctaa agcacctcca ggtgaacaat ttaatcactt gagagcgtta ttcaaaagtg  17400
ctaaaccttg gcatgttgta aggccaagga ttgtgcaaat gttagcggat aacctgtgca  17460
acgtttcaga ttgtgtagtg tttgtcacgt ggtgtcatgg cctagaacta accactttgc  17520
gctattttgt taaaataggc aaggaccaag tttgttcttg cggttctaga gcaacaactt  17580
ttaattctca tactcaggct tatgcttgtt ggaagcattg cttgggtttt gattttgttt  17640
ataatccact cttagtggat attcaacagt ggggttattc tggtaaccta caatttaacc  17700
atgatttgca ttgtaatgtg catggacacg cacatgtagc ttctgcggat gctattatga  17760
cgcgttgtct tgcaattaat aatgcatttt gtcaagatgt caactgggat ttaacttacc  17820
ctcatatagc aaatgaggat gaagtcaatt ctagctgtag atatttacaa cgcatgtatc  17880
ttaatgcatg tgttgatgct cttaaagtta acgttgtcta tgatataggc aaccctaaag  17940
gtataaaatg tgttagacgt ggagacttaa atttagatt ctatgataag aatccaatag  18000
tacccaatgt caagcagttt gagtatgact ataatcagca caagataag tttgctgatg  18060 gtctttgtat gttttggaat tgtaatgtgg attgttatcc cgacaattcc ttagtttgta  18120
ggtacgacac acgaaatttg agtgtgttta acctacctgg ttgtaatggt ggtagcttgt  18180
atgttaacaa gcatgcattc cacacaccta aatttgatcg cactagcttt cgtaatttga  18240
aagctatgcc attctttttc tatgactcat cgccttgcga gaccattcaa ttggatggag  18300
ttgcgcaaga ccttgtgtca ttagctacga aagattgtat cacaaaatgc aacataggcg  18360
gtgctgtttg taaaaagcac gcacaaatgt atgcagattt tgtgacttct tataatgcag  18420
ctgttactgc tggttttact ttttgggtta ctaataattt aacccatat aatttgtgga  18480 aaagttttc agctctccag tctatcgaca atattgctta atatgtat aagggtggtc  18540 attatgatgc tattgcagga gaaatgccca ctatcgtaac tggagataaa gttttgtta  18600 tagatcaagg cgtagaaaaa gcagtttttt ttaatcaaac aattctgcct acatctgtag  18660
cgtttgagct gtatgcgaag agaaatattc gcacactgcc aaacaaccgt attttgaaag  18720
gtttgggtgt agatgtgact aatggatttg taatttggga ttacacgaac caaacaccac  18780
```

```
tataccgtaa tactgttaag gtatgtgcat atacagacat agaaccaaat ggcctaatag    18840
tgctgtatga tgatagatat ggtgattacc agtcttttct agctgctgat aatgctgttt    18900
tagtttctac acagtgttac aagcggtatt cgtatgtaga aataccgtca aacctgcttg    18960
ttcagaacgg tattccgtta aaagatggag cgaacctgta tgtttataag cgtgttaatg    19020
gtgcgtttgt tacgctacct aacacattaa acacacaggg tcgcagttat gaaacttttg    19080
aacctcgtag tgatgttgag cgtgattttc tcgacatgtc tgaggagagt tttgtagaaa    19140
agtatggtaa agaattaggt ctacagcaca tactgtatgg tgaagttgat aagccccaat    19200
taggtggttt acacactgtt ataggtatgt gcagactttt acgtgcgaat aagttgaacg    19260
caaagtctgt tactaattct gattctgatg tcatgcaaaa ttattttgta ttggcagaca    19320
atggttccta caagcaagtg tgtactgttg tggatttgct gcttgatgat ttcttagaac    19380
ttcttaggaa catactgaaa gagtatggta ctaataagtc taaagttgta acagtgtcaa    19440
ttgattacca tagcataaat tttatgactt ggtttgaaga tggcattatt aaaacatgtt    19500
atccacagct tcaatcagca tggacgtgtg gttataatat gcctgaactt tataaagttc    19560
agaattgtgt tatggaacct tgcaacattc ctaattatgg tgttggaata gcgttgccaa    19620
gtggtattat gatgaatgtg gcaaagtata cacaactctg tcaataccct tcgaaaacaa    19680
caatgtgtgt accgcataat atgcgagtaa tgcattttgg agctggaagt gacaaaggag    19740
tggctccagg tagtactgtt cttaaacaat ggctcccaga agggacactc cttgtcgata    19800
atgatattgt agactatgtg tctgatgcac atgtttctgt gctttcagat tgcaataaat    19860
ataagacaga gcacaagttt gatcttgtga tatctgatat gtatacagac aatgattcaa    19920
aaagaaagca tgaaggcgtg atagccaata tggcaatga tgacgttttc atatatctct    19980
caagttttct tcgtaataat ttggctctag gtggtagttt tgctgtaaaa gtgacagaga    20040
caagttggca cgaagtttta tatgacattg cacaggattg tgcatggtgg acaatgtttt    20100
gtacagcagt gaatgcctct tcttcagaag cattcttggt tggtgttaat tatttgggtg    20160
caagtgaaaa ggttaaggtt agtggaaaaa cgctgcacgc aaattatata ttttggagga    20220
attgtaatta tttacaaacc tctgcttata gtatatttga cgttgctaag tttgatttga    20280
gattgaaagc aacaccagtt gttaatttga aaactgaaca aaagacagac ttagtcttta    20340
atttaattaa gtgtggtaag ttactggtaa gagatgttgg taacacctct tttactagtg    20400
actcttttgt gtgtactatg tagtgctgct ttgtatgaca gtagttctta cgtttactac    20460
taccaaagtg cctttagacc acctaatggt tggcatttac acggggtgc ttatgcggta    20520 gttaatattt ctagcgaatc taataatgca ggctcttcac ctgggtgtat tgttggtact    20580
attcatggtg gtcgtgttgt taatgcttct tctatagcta tgacggcacc gtcatcaggt    20640
atggcttggt ctagcagtca gttttgtact gcacactgta acttttcaga tactacagtg    20700
tttgttacac attgttataa atatgatggg gtgtcctataa ctggcatgct tcaaaagaat    20760 ttttacgtg tttctgctat gaaaaatggc cagcttttct ataatttaac agttagtgta    20820
gctaagtacc ctactttttaa atcatttcag tgtgttaata atttaacatc cgtatattta    20880
aatggtgatc ttgtttacac ctctaatgag accacagatg ttcatctgc aggtgtttat    20940 tttaaagctg gtggacctat aacttataaa gttatgagag aagttaaagc cctggcttat    21000
tttgttaatg gtactgcaca agatgttatt ttgtgtgatg gatcacctag aggcttgtta    21060
gcatgccagt ataatactgg caattttttca gatggctttt atccttttat taatagtagt    21120
ttagttaagc agaagtttat tgtctatcgt gaaaatagtg ttaatactac ttttacgtta    21180
```

```
cacaatttca cttttcataa tgagactggc gccaaccta atcctagtgg tgttcagaat    21240
attcaaactt accaaacaca aacagctcag agtggttatt ataattttaa tttttccttt    21300
ctgagtagtt ttgttataa ggagtctaat tttatgtatg gatcttatca cccaagttgt    21360
aattttagac tagaaactat taataatggc ttgtggttta attcactttc agtttcaatt    21420
gcttacggtc ctcttcaagg tggttgcaag caatctgtct ttagtggtag agcaacttgt    21480
tgttatgctt attcatatgg aggtccttcg ctgtgtaaag gtgtttattc aggtgagtta    21540
gatcttaatt ttgaatgtgg actgttagtt tatgttacta agagcggtgg ctctcgtata    21600
caaacagcca ctgaaccgcc agttataact cgacacaatt ataataatat tactttaaat    21660
acttgtgttg attataatat atatggcaga actggccaag gttttattac taatgtaacc    21720
gactcagctg ttagttataa ttatctagca gacgcaggtt tggctatttt agatacatct    21780
ggttccatag acatctttgt tgtacaaggt gaatatggtc ttacttatta taaggttaac    21840
ccttgcgaag atgtcaacca gcagtttgta gtttctggtg gtaaattagt aggtattctt    21900
acttcacgta atgagactgg ttctcagctt cttgagaacc agttttacat taaaatcact    21960
aatggaacac gtcgttttag acgttctatt actgaaaatg ttgcaaattg cccttatgtt    22020
agttatggta agttttgtat aaaacctgat ggttcaattg ccacaatagt accaaaacaa    22080
ttggaacagt tgtggcacc tttacttaat gttactgaaa atgtgctcat acctaacagt    22140
tttaatttaa ctgttacaga tgagtacata caaacgcgta tggataaggt ccaaattaat    22200
tgtctgcagt atgtttgtgg caattctctg gattgtagag atttgtttca acaatatggg    22260
cctgtttgtg acaacatatt gtctgtagta aatagtattg gtcaaaaaga agatatggaa    22320
cttttgaatt tctattcttc tactaaaccg gctggtttta ataccattt tcttagtaat    22380 gttagcactg gtgagtttaa tatttctctt ctgttaacaa ctcctagtag tcctagaagg    22440
cgttctttta ttgaagacct tctatttaca agcgttgaat ctgttggatt accaacagat    22500
gacgcataca aaaattgcac tgcaggacct ttaggttttc ttaaggacct tgcgtgtgct    22560
cgtgaatata atggtttgct tgtgttgcct cccattataa cagcagaaat gcaaattttg    22620
tatactagtt ctcagtagc ttctatggct tttggtggta ttactgcagc tggtgctata    22680
ccttttgcca cacaactgca ggctagaatt aatcacttgg gtattaccca gtcacttttg    22740
ttgaagaatc aagaaaaaat tgctgcttcc tttaataagg ccattggtcg tatgcaggaa    22800
ggttttagaa gtacatctct agcattacaa caaattcaag atgttgttaa taagcagagt    22860
gctattctta ctgagactat ggcatcactt aataaaaatt ttggtgctat ttcttctatg    22920
attcaagaaa tctaccagca acttgacgcc atacaagcaa atgctcaagt ggatcgtctt    22980
ataactggta gattgtcatc actttctgtt ttagcatctg ctaagcaggc ggagcatatt    23040
agagtgtcac aacagcgtga gttagctact cagaaaatta atgagtgtgt taagtcacag    23100
tctattaggt actcctttg tggtaatgga cgacatgttc taaccatacc gcaaaatgca    23160
cctaatggta tagtgtttat acacttttct tatactccag atagttttgt taatgttact    23220
gcaatagtgg ttttgtgt aaagccagct aatgctagtc agtatgcaat agtacccgct    23280
aatggtaggg tattttat acaagttaat ggtagttact acatcacagc acgagatatg    23340
tatatgccaa gagctattac tgcaggagat atagttacgc ttacttcttg tcaagcaaat    23400
tatgtaagtg taaataagac cgtcattact acattcgtag acaatgatga ttttgatttt    23460
aatgacgaat tgtcaaaatg gtggaatgac actaagcatg agctaccaga ctttgacaaa    23520
```

```
ttcaattaca cagtacctat acttgacatt gatagtgaaa ttgatcgtat tcaaggcgtt    23580
atacagggtc ttaatgactc tttaatagac cttgaaaaac tttcaatact caaaacttat    23640
attaagtggc cttggtatgt gtggttagcc atagcttttg ccactattat cttcatctta    23700
atactaggat gggttttctt catgactgga tgttgtggtt gttgttgtgg atgctttggc    23760
attatgcctc taatgagtaa gtgtggtaag aaatcttctt attacacgac ttttgataac    23820
gatgtggtaa cttaacaata cagacctaaa agtctgtttt aatgattcaa gtcccacgt    23880 ccttcctaat agtattaatt tttctttggt gtaaacttgt actaagttgt tttagagagt    23940
ttattatagc gctccaacaa ctaatacaag ttttactcca aattatcaat agtaacttac    24000
agcctagact gacccttttgt cacagtctag actaatgtta aacttagaag caattattga    24060
aactggtgag caagtgattc aaaaaatcag tttcaattta cagcatattt caagtgtatt    24120
aaacacagaa gtatttgacc cctttgacta ttgttattac agaggaggta atttttggga    24180
aatagagtca gctgaagatt gttcaggtga tgatgaattt attgaataag tcgctagagg    24240
aaaatggaag ttttctaaca gcgctttata tatttgtagg attttttagca ctttatcttc    24300 taggtagagc acttcaagca tttgtacagg ctgctgatgc ttgttgttta ttttggtata    24360
catgggtagt aattccagga gctaagggta cagccttttgt atataagtat acatatggta    24420
gaaaacttaa caatccggaa ttagaagcag ttattgtcaa cgagttcct aagaacggtt    24480 ggaataataa aaatccagca aatttttcaag atgtccaacg agacaaattg tactcttgac    24540
tttgaacagt cagttgagct ttttaaagag tataatttat ttataactgc attcttgttg    24600
ttcttaacca taatacttca gtatggctat gcaacaagaa gtaagtttat ttatatactg    24660
aaaatgatag tgttatggtg ctttttggccc cttaacattg cagtaggtgt aatttcatgt    24720
atatacccac caaacacagg aggtcttgtc gcagcgataa tacttacagt gtttgcgtgt    24780
ctgtcttttg taggttattg gatccagagt attagactct ttaagcggtg taggtcatgg    24840
tggtcattta acccagaatc taatgccgta ggttcaatac tcctaactaa tggtcaacaa    24900
tgtaattttg ctatagagag tgtgccaatg gtgctttctc caattataaa gaatggtgtt    24960
ctttattgtg agggtcagtg gcttgctaag tgtgaaccag accacttgcc taaagatata    25020
tttgtttgta caccggatag acgtaatatc taccgtatgg tgcagaaata tactggtgac    25080
caaagcggaa ataagaaacg gtttgctacg tttgtctatg caaagcagtc agtagatact    25140
ggcgagctag aaagtgtagc aacaggaggg agtagtcttt acacctaaat gtgtgtgtgt    25200
agagagtatt taaaattatt ctttaatagt gcctctattt taagagcgca taatagtatt    25260
atttttgagg atattaatat aaatcctctc tgtttttatac tctcttttca agagctatta    25320 tttaaaaac agttttttcca ctctttttgtg ccaaaaacta ttgttgttaa tggtgtaacc    25380
tttcaagtag ataatggaaa agtctactac gaaggaaaac caatttttca gaaaggttgt    25440
tgtaggttgt ggttgagtta taaaaaagat taaactacct actacactta tttttataag    25500
aggcgtttta tcttacaagc gcttaataaa tacggacgat gaaatggctg actagttttg    25560
taagggcagt tatttcatgt tataaacccc tattattaac tcaattaaga gtattagata    25620
ggttaatctt agatcatgga ccaaaacaca tcttaacgtg tgttaggtgc gtgatttgt    25680 ttcaattaga tttagtttat aggttggcgt atacgcctac tcaatcgctg gtatgaataa    25740
tagtaaagat aatcctttt gcggagcaat agcaagaaaa gcgcgaattt atctgagaga    25800
aggattagat tgtgttact ttcttaacaa agcaggacaa gcagagtctt gtcccgcgtg    25860
tacctctcta gtattccagg ggaaaacttg tgaggaacac aaatataata ataatctttt    25920
```

```
gtcatggcaa gcggtaaggc aactggaaag acagatgccc cagctccagt catcaaacta    25980
ggaggaccaa agccacctaa agttggttct tctggaaatg tatcttggtt tcaagcaata    26040
aaagccaaga agttaaattc acctccgcct aagtttgaag gtagcggtgt tcctgataat    26100
gaaaatctaa aaccaagtca gcagcatgga tattggagac gccaagctag gtttaagcca    26160
ggtaaaggtg aagaaaacc agtcccagat gcttggtatt tttactatac tggaacagga    26220
ccagccgcta acctgaattg gggtgatagc caagatggta tagtgtgggt tgctggtaag    26280
ggtgctgata ctaaatttag atctaatcag ggtactcgtg actctgacaa gtttgaccaa    26340
tatccgctac ggttttcaga cggaggacct gatggtaatt ccgttgggga tttcattcct    26400
ctgaatcgtg gcaggagtgg gagatcaaca gcagcttcat cagcagcatc tagtagagca    26460
ccatcacgtg aagtttcgcg tggtcgcagg agtggttctg aagatgatct tattgctcgt    26520
gcagcaagga taattcagga tcagcagaag aagggttctc gcattacaaa ggctaaggct    26580
gatgaaatgg ctcaccgccg gtattgcaag cgcactattc cacctaatta taaggttgat    26640
caagtgtttg gtccccgtac taaaggtaag gagggaaatt ttggtgatga caagatgaat    26700
gaggaaggta ttaaggatgg gcgcgttaca gcaatgctca acctagttcc tagcagccat    26760
gcttgtcttt tcggaagtag agtgacgccc agacttcaac cagatgggct gcacttgaaa    26820
tttgaattta ctactgtggt cccacgtgat gatccgcagt ttgataatta tgtaaaaatt    26880
tgtgatcagt gtgttgatgg tgtaggaaca cgtccaaaag atgatgaacc aagaccaaag    26940
tcacgctcaa gttcaagacc tgcaacaaga ggaaattctc cagcgccaag acagcagcgc    27000
cctaagaagg agaaaaagcc aaagaagcag gatgatgaag tggataaagc attgacctca    27060
gatgaggaga ggaacaatgc acagctggaa tttgatgatg aacccaaggt aattaactgg    27120
ggggattcag ccctaggaga gaatgaactt tgagtaaaat tcaatagtaa gagttaagga    27180
agataggcat gtagcttgat tacctacatg tctatcgcca gggaaatgtc taatttgtct    27240
acttagtagc ctggaaacga acggtagacc cttagatttt aattttagttt aatttttagt    27300 ttagtttaag ttagtttaga gtaggtataa agatgccagt gccggggcca cgcggagtac    27360
gaccgagggt acagcactag gacgcccatt aggggaagag ctaaatttta gtttaagtta    27420
agtttaattg gctatgtata gttaaaattt ataggctagt atagagttag agcaaaaaaa    27480
aaaaaaaaaa aaaaaaaaaa                                                27500

<210> SEQ ID NO 2
<211> LENGTH: 709
<212> TYPE: DNA
<213> ORGANISM: Avian infectious bronchitis virus

<400> SEQUENCE: 2
cttaacaata cagacctaaa aagtctgttt aatgattcaa agtcccacgt ccttcctaat        60
agtattaatt tttctttggt gtaaacttgt actaagttgt tttagagagt ttattatagc       120
gctccaacaa ctaatacaag ttttactcca aattatcaat agtaacttac agcctagact       180 gacccctttgt cacagtctag actaatgtta aacttagaag caattattga aactggtgag       240
caagtgattc aaaaaatcag tttcaattta cagcatattt caagtgtatt aaacacagaa       300
gtatttgacc cctttgacta ttgttattac agaggaggta attttttggga aatagagtca       360 gctgaagatt gttcaggtga tgatgaattt attgaataag tcgctagagg aaaatggaag       420
ttttctaaca gcgctttata tatttgtagg attttttagca ctttatcttc taggtagagc       480
```

```
acttcaagca tttgtacagg ctgctgatgc ttgttgttta ttttggtata catgggtagt    540
aattccagga gctaagggta cagcctttgt atataagtat acatatggta gaaaacttaa    600
caatccggaa ttagaagcag ttattgtcaa cgagtttcct aagaacggtt ggaataataa    660
aaatccagca aattttcaag atgtccaacg agacaaattg tactcttga               709
```

<210> SEQ ID NO 3
<211> LENGTH: 57
<212> TYPE: PRT
<213> ORGANISM: Avian infectious bronchitis virus

<400> SEQUENCE: 3

```
Met Ile Gln Ser Pro Thr Ser Phe Leu Ile Val Leu Ile Phe Leu Trp
1               5                   10                  15

Cys Lys Leu Val Leu Ser Cys Phe Arg Glu Phe Ile Ile Ala Leu Gln
            20                  25                  30

Gln Leu Ile Gln Val Leu Leu Gln Ile Ile Asn Ser Asn Leu Gln Pro
        35                  40                  45

Arg Leu Thr Leu Cys His Ser Leu Asp
    50                  55
```

<210> SEQ ID NO 4
<211> LENGTH: 64
<212> TYPE: PRT
<213> ORGANISM: Avian infectious bronchitis virus

<400> SEQUENCE: 4

```
Met Leu Asn Leu Glu Ala Ile Ile Glu Thr Gly Glu Gln Val Ile Gln
1               5                   10                  15

Lys Ile Ser Phe Asn Leu Gln His Ile Ser Ser Val Leu Asn Thr Glu
            20                  25                  30

Val Phe Asp Pro Phe Asp Tyr Cys Tyr Tyr Arg Gly Gly Asn Phe Trp
        35                  40                  45

Glu Ile Glu Ser Ala Glu Asp Cys Ser Gly Asp Asp Glu Phe Ile Glu
    50                  55                  60
```

<210> SEQ ID NO 5
<211> LENGTH: 4782
<212> TYPE: DNA
<213> ORGANISM: Avian infectious bronchitis virus

<400> SEQUENCE: 5

```
ggtaaaactg tcacctttgg agaaactact gtgcaagaaa taccaccacc tgatgttgtg    60
tttattaagg ttagcattga gtgttgtggt gaaccatgga atacaatctt caaaaaggct   120
tataaggagc ccattgaagt agagacagac ctcacagttg aacaattgct ctctgtggtc   180
tatgagaaaa tgtgtgatga tctcaagctg tttccggagg ctccagaacc accaccattt   240
gagaatgtca cacttgttga taagaatggt aaagatttgg attgcataaa atcatgccat   300
ctgatctatc gtgattatga gagcgatgat gacatcgagg aagaagatgc agaagaatgt   360
gacacggatt caggtgatgc tgaggagtgt gacactaatt cagaatgtga agaagaagat   420
gaggatacta aagtgttggc tcttatacaa gacccggcaa gtaacaaata tcctctgcct   480
cttgatgatg attatagcgt ctacaatgga tgtattgttc ataaggacgc tctcgatgtt   540
gtgaatttac catctggtga agaaccttt gttgtcaata actgctttga gggggtgtt   600 aaagctcttc cgcagaaagt tattgatgtt ctaggtgact ggggtgaggc tgttgatgcg   660
caagaacaat tgtgtcaaca agaatcaact cgggtcatat ctgagaaatc agttgagggt   720
```

```
tttactggta gttgtgatgc aatggctgaa caagctattg ttgaagagca ggaaatagta    780
cctgttgttg aacaaagtca ggatgtagtt gttttacac ctgcagacct agaagttgtt     840
aaagaaacag cagaagaggt tgatgagttt attctcattt ctgctgtccc taaagaagaa    900
gttgtgtctc aggagaaaga ggagccacag gttgagcaag agcctaccct agttgttaaa    960
gcacaacgtg agaagaaggc taaaaagttc aaagttaaac cagctacatg tgaaaaaccc   1020
aaattttttgg agtacaaaac atgtgtgggt gatttggctg ttgtaattgc caaagcattg   1080
gatgagttta aagagttctg cattgtaaac gctgcaaatg agcacatgtc gcatggtggt   1140
ggcgttgcaa aggcaattgc agactttgt ggaccggact tgttgaata ttgcgcggac      1200
tatgttaaga acatggtcc acagcaaaaa cttgtcacac cttcatttgt taaaggcatt    1260
caatgtgtga ataatgttgt aggacctcgc catggagaca gcaacttgcg tgagaagctt   1320
gttgctgctt acaagagtgt tcttgtaggt ggagtggtta actatgttgt gccagttctc   1380
tcatcaggga tttttggtgt agatttaaa atatcaatag atgctatgcg cgaagctttt    1440
aaaggttgtg ccatacgcgt tctttattt tctctgagtc aagaacacat cgattatttc    1500
gatgcaactt gtaagcagaa gacaatttat cttacggagg atggtgttaa ataccgctct   1560
gttgttttaa aacctggtga ttctttgggt caatttggac aggttttgc aagaaataag     1620
gtagtctttt cggctgatga tgttgaggat aaagaaatcc tcttatacc cacaactgac    1680
aagactattc ttgaatatta tggtttagat gcgcaaaagt atgtaacata tttgcaaacg   1740
cttgcgcaga aatgggatgt tcaatataga gacaattttg ttatattaga gtggcgtgac   1800
ggaaattgct ggattagttc agcaatagtt ctccttcaag ctgctaaaat tagatttaaa   1860
ggttttcttg cagaagcatg ggctaaactg ttgggtggag atcctacaga ctttgttgcc   1920
tggtgttatg caagttgcaa tgctaaagta ggtgatttt cagatgctaa ttggctttg    1980
gccaatttag cagaacattt tgacgcagat tacacaaatg cacttcttaa gaagtgtgtg   2040
tcgtgcaatt gtggtgttaa gagttatgaa cttaggggtc ttgaagcctg tattcagcca   2100
gttcgagcac taatcttct acattttaaa acgcaatatt caaattgccc aacctgtggt    2160
gcaagtagta cggatgaagt aatagaagct tcattaccgt acttattgct tttgctact    2220
gatggtcctg ctacagttga ttgtgatgaa aatgctgtag gactgttgt tttcattggc   2280
tctactaata gtgggccattg ttatacacaa gccgatggta aggcttttga caatcttgct   2340
aaggatagaa aatttggaag gaagtcgcct tacattacag caatgtatac acgtttttct   2400
cttaggagtg aaaatccct acttgttgtt gaacatagta agggtaaagc taagtagta     2460
aaagaagatg tttctaacct tgctactagt tctaaagcca gttttgacga tcttactgac   2520
tttgaacagt ggtatgatag caacatctat gagagtctta agtgcagga gacacctgat   2580
aatcttgatg aatatgtgtc atttacgaca aaggaagatt ctaagttgcc actgacactt   2640
aaagttagag gtatcaaatc agttgttgac tttaggtcta aggatggttt tacttataag   2700
ttaacacctg atactgatga aaattcaaaa acaccagtct actacccagt cttggattct   2760
attagtctta gggcaatatg ggttgaaggc agtgctaatt tgttgttgg gcatccaaat   2820
tattatagta agtctctccg aattcccacg ttttgggaaa atgccgagag ctttgttaaa   2880
atgggttata aaattgatgg tgtaactatg ggcctttggc gtgcagaaca ccttaataaa   2940
cctaattttgg agagaattt taacattgct aagaaagcta ttgttggatc tagtgttgtt   3000
actacgcagt gtggtaaaat actagttaaa gcagctacat acgttgccga taaagtaggt   3060
```

```
gatggtgtag ttcgcaatat tacagataga attaagggtc tttgtggatt cacacgtggc    3120
cattttgaaa agaaaatgtc cctacaattt ctaaagacac ttgtgttctt tttcttttat    3180
ttcttaaagg ctagtgctaa gagtttagtt tctagctata agattgtgtt atgtaaggtg    3240
gtgtttgcta ccttacttat agtgtggttt atatacacaa gtaatccagt agtgtttact    3300
ggaatacgtg tgctagactt cctatttgaa ggttctttat gtggtcctta taatgactac    3360
ggtaaagatt cttttgatgt gttacgctat tgtgcaggtg attttacttg tcgtgtgtgt    3420
ttacatgata gagattcact tcatctgtac aaacatgctt atagcgtaga acaaatttat    3480
aaggatgcag cttctggcat taactttaat tggaattggc tttatttggt ctttctaata    3540
ttatttgtta agccagtggc aggttttgtt attatttgtt attgtgttaa gtatttggta    3600
ttgagttcaa ctgtgttgca aactggtgta ggttttctag attggtttgt aaaaacagtt    3660
tttacccatt ttaattttat gggagcggga ttttatttct ggctctttta caagatatac    3720
gtacaagtgc atcatatatt gtactgtaag gatgtaacat gtgaagtgtg caagagagtt    3780
gcacgcagca acaggcaaga ggttagcgtt gtagttggtg acgcaagca aatagtgcat    3840 gtttacacta attctggcta taacttttgt aagagacata attggtattg tagaaattgt    3900
gatgattatg gtcaccaaaa tacatttatg tcccctgaag ttgctggcga gctttctgaa    3960
aagcttaagc gccatgttaa acctacagca tatgcttacc acgttgtgta tgaggcatgc    4020
gtggttgatg attttgttaa tttaaaatat aaggctgcaa ttcctggtaa ggataatgca    4080
tcttctgctg ttaagtgttt cagtgttaca gatttttaa agaaagctgt ttttcttaag    4140
gaggcattga aatgtgaaca aatatctaat gatggtttta tagtgtgtaa tacacagagt    4200
gcgcatgcac tagaggaagc aaagaatgca gccgtctatt atgcgcaata tctgtgtaag    4260
ccaatactta tacttgacca ggcactttat gagcaattaa tagtagagcc tgtgtctaag    4320
agtgttatag ataaagtgtg tagcattttg tctaatataa tatctgtaga tactgcagct    4380
ttaaattata aggcaggcac acttcgtgat gctctgcttt ctattactaa agacgaagaa    4440
gccgtagata tggctatctt ctgccacaat catgaagtgg aatacactgg tgacggtttt    4500
actaatgtga taccgtcata tggtatggac actgataagt tgacacctcg tgatagaggg    4560 ttttgataa atgcagatgc ttctattgct aatttaagag tcaaaatgc tcctccggta    4620 gtatggaagt tttctgatct tattaaattg tctgacagtt gccttaaata tttaattca    4680 gctactgtca agtcaggagg tcgtttcttt ataacaaagt ctggtgctaa acaagttatt    4740
tcttgtcata cccagaaact gttggtagag aaaaaggcag gt                       4782
```

<210> SEQ ID NO 6
<211> LENGTH: 1594
<212> TYPE: PRT
<213> ORGANISM: Avian infectious bronchitis virus

<400> SEQUENCE: 6

```
Gly Lys Thr Val Thr Phe Gly Glu Thr Thr Val Gln Glu Ile Pro Pro
1               5                   10                  15

Pro Asp Val Val Phe Ile Lys Val Ser Ile Glu Cys Cys Gly Glu Pro
            20                  25                  30

Trp Asn Thr Ile Phe Lys Lys Ala Tyr Lys Glu Pro Ile Glu Val Glu
        35                  40                  45

Thr Asp Leu Thr Val Glu Gln Leu Leu Ser Val Val Tyr Glu Lys Met
    50                  55                  60

Cys Asp Asp Leu Lys Leu Phe Pro Glu Ala Pro Glu Pro Pro Pro Phe
```

-continued

```
                65                  70                  75                  80
Glu Asn Val Thr Leu Val Asp Lys Asn Gly Lys Asp Leu Asp Cys Ile
                    85                  90                  95

Lys Ser Cys His Leu Ile Tyr Arg Asp Tyr Glu Ser Asp Asp Ile
                100                 105                 110

Glu Glu Glu Asp Ala Glu Cys Asp Thr Asp Ser Gly Asp Ala Glu
                115                 120                 125

Glu Cys Asp Thr Asn Ser Glu Cys Glu Glu Asp Glu Asp Thr Lys
                130                 135                 140

Val Leu Ala Leu Ile Gln Asp Pro Ala Ser Asn Lys Tyr Pro Leu Pro
145                 150                 155                 160

Leu Asp Asp Asp Tyr Ser Val Tyr Asn Gly Cys Ile Val His Lys Asp
                    165                 170                 175

Ala Leu Asp Val Val Asn Leu Pro Ser Gly Glu Glu Thr Phe Val Val
                180                 185                 190

Asn Asn Cys Phe Glu Gly Ala Val Lys Ala Leu Pro Gln Lys Val Ile
                195                 200                 205

Asp Val Leu Gly Asp Trp Gly Glu Ala Val Asp Ala Gln Glu Gln Leu
210                 215                 220

Cys Gln Gln Glu Ser Thr Arg Val Ile Ser Glu Lys Ser Val Glu Gly
225                 230                 235                 240

Phe Thr Gly Ser Cys Asp Ala Met Ala Glu Gln Ala Ile Val Glu Glu
                    245                 250                 255

Gln Glu Ile Val Pro Val Val Glu Gln Ser Gln Asp Val Val Phe
                260                 265                 270

Thr Pro Ala Asp Leu Glu Val Val Lys Glu Thr Ala Glu Glu Val Asp
                275                 280                 285

Glu Phe Ile Leu Ile Ser Ala Val Pro Lys Glu Val Val Ser Gln
                290                 295                 300

Glu Lys Glu Glu Pro Gln Val Glu Gln Glu Pro Thr Leu Val Val Lys
305                 310                 315                 320

Ala Gln Arg Glu Lys Lys Ala Lys Lys Phe Lys Val Lys Pro Ala Thr
                    325                 330                 335

Cys Glu Lys Pro Lys Phe Leu Glu Tyr Lys Thr Cys Val Gly Asp Leu
                340                 345                 350

Ala Val Val Ile Ala Lys Ala Leu Asp Glu Phe Lys Glu Phe Cys Ile
                355                 360                 365

Val Asn Ala Ala Asn Glu His Met Ser His Gly Gly Gly Val Ala Lys
                370                 375                 380

Ala Ile Ala Asp Phe Cys Gly Pro Asp Phe Val Glu Tyr Cys Ala Asp
385                 390                 395                 400

Tyr Val Lys Lys His Gly Pro Gln Gln Lys Leu Val Thr Pro Ser Phe
                    405                 410                 415

Val Lys Gly Ile Gln Cys Val Asn Asn Val Val Gly Pro Arg His Gly
                420                 425                 430

Asp Ser Asn Leu Arg Glu Lys Leu Val Ala Ala Tyr Lys Ser Val Leu
                435                 440                 445

Val Gly Gly Val Val Asn Tyr Val Val Pro Val Leu Ser Ser Gly Ile
                450                 455                 460

Phe Gly Val Asp Phe Lys Ile Ser Ile Asp Ala Met Arg Glu Ala Phe
465                 470                 475                 480

Lys Gly Cys Ala Ile Arg Val Leu Leu Phe Ser Leu Ser Gln Glu His
                    485                 490                 495
```

```
Ile Asp Tyr Phe Asp Ala Thr Cys Lys Gln Lys Thr Ile Tyr Leu Thr
            500                 505                 510

Glu Asp Gly Val Lys Tyr Arg Ser Val Val Leu Lys Pro Gly Asp Ser
            515                 520                 525

Leu Gly Gln Phe Gly Gln Val Phe Ala Arg Asn Lys Val Val Phe Ser
            530                 535                 540

Ala Asp Asp Val Glu Asp Lys Glu Ile Leu Phe Ile Pro Thr Thr Asp
545                 550                 555                 560

Lys Thr Ile Leu Glu Tyr Tyr Gly Leu Asp Ala Gln Lys Tyr Val Thr
                565                 570                 575

Tyr Leu Gln Thr Leu Ala Gln Lys Trp Asp Val Gln Tyr Arg Asp Asn
            580                 585                 590

Phe Val Ile Leu Glu Trp Arg Asp Gly Asn Cys Trp Ile Ser Ser Ala
            595                 600                 605

Ile Val Leu Leu Gln Ala Ala Lys Ile Arg Phe Lys Gly Phe Leu Ala
            610                 615                 620

Glu Ala Trp Ala Lys Leu Leu Gly Gly Asp Pro Thr Asp Phe Val Ala
625                 630                 635                 640

Trp Cys Tyr Ala Ser Cys Asn Ala Lys Val Gly Asp Phe Ser Asp Ala
                645                 650                 655

Asn Trp Leu Leu Ala Asn Leu Ala Glu His Phe Asp Ala Asp Tyr Thr
            660                 665                 670

Asn Ala Leu Leu Lys Lys Cys Val Ser Cys Asn Cys Gly Val Lys Ser
            675                 680                 685

Tyr Glu Leu Arg Gly Leu Glu Ala Cys Ile Gln Pro Val Arg Ala Pro
            690                 695                 700

Asn Leu Leu His Phe Lys Thr Gln Tyr Ser Asn Cys Pro Thr Cys Gly
705                 710                 715                 720

Ala Ser Ser Thr Asp Glu Val Ile Glu Ala Ser Leu Pro Tyr Leu Leu
                725                 730                 735

Leu Phe Ala Thr Asp Gly Pro Ala Thr Val Asp Cys Asp Glu Asn Ala
            740                 745                 750

Val Gly Thr Val Val Phe Ile Gly Ser Thr Asn Ser Gly His Cys Tyr
            755                 760                 765

Thr Gln Ala Asp Gly Lys Ala Phe Asp Asn Leu Ala Lys Asp Arg Lys
770                 775                 780

Phe Gly Arg Lys Ser Pro Tyr Ile Thr Ala Met Tyr Thr Arg Phe Ser
785                 790                 795                 800

Leu Arg Ser Glu Asn Pro Leu Leu Val Val Glu His Ser Lys Gly Lys
                805                 810                 815

Ala Lys Val Val Lys Glu Asp Val Ser Asn Leu Ala Thr Ser Ser Lys
            820                 825                 830

Ala Ser Phe Asp Asp Leu Thr Asp Phe Glu Gln Trp Tyr Asp Ser Asn
            835                 840                 845

Ile Tyr Glu Ser Leu Lys Val Gln Glu Thr Pro Asp Asn Leu Asp Glu
            850                 855                 860

Tyr Val Ser Phe Thr Thr Lys Glu Asp Ser Lys Leu Pro Leu Thr Leu
865                 870                 875                 880

Lys Val Arg Gly Ile Lys Ser Val Val Asp Phe Arg Ser Lys Asp Gly
                885                 890                 895

Phe Thr Tyr Lys Leu Thr Pro Asp Thr Asp Glu Asn Ser Lys Thr Pro
            900                 905                 910
```

-continued

Val Tyr Tyr Pro Val Leu Asp Ser Ile Ser Leu Arg Ala Ile Trp Val
            915                 920                 925

Glu Gly Ser Ala Asn Phe Val Val Gly His Pro Asn Tyr Tyr Ser Lys
930                 935                 940

Ser Leu Arg Ile Pro Thr Phe Trp Glu Asn Ala Glu Ser Phe Val Lys
945                 950                 955                 960

Met Gly Tyr Lys Ile Asp Gly Val Thr Met Gly Leu Trp Arg Ala Glu
            965                 970                 975

His Leu Asn Lys Pro Asn Leu Glu Arg Ile Phe Asn Ile Ala Lys Lys
            980                 985                 990

Ala Ile Val Gly Ser Ser Val Val Thr Thr Gln Cys Gly Lys Ile Leu
        995                 1000                1005

Val Lys Ala Ala Thr Tyr Val Ala Asp Lys Val Gly Asp Gly Val
        1010                1015                1020

Val Arg Asn Ile Thr Asp Arg Ile Lys Gly Leu Cys Gly Phe Thr
        1025                1030                1035

Arg Gly His Phe Glu Lys Lys Met Ser Leu Gln Phe Leu Lys Thr
        1040                1045                1050

Leu Val Phe Phe Phe Phe Tyr Phe Leu Lys Ala Ser Ala Lys Ser
        1055                1060                1065

Leu Val Ser Ser Tyr Lys Ile Val Leu Cys Lys Val Val Phe Ala
        1070                1075                1080

Thr Leu Leu Ile Val Trp Phe Ile Tyr Thr Ser Asn Pro Val Val
        1085                1090                1095

Phe Thr Gly Ile Arg Val Leu Asp Phe Leu Phe Glu Gly Ser Leu
        1100                1105                1110

Cys Gly Pro Tyr Asn Asp Tyr Gly Lys Asp Ser Phe Asp Val Leu
        1115                1120                1125

Arg Tyr Cys Ala Gly Asp Phe Thr Cys Arg Val Cys Leu His Asp
        1130                1135                1140

Arg Asp Ser Leu His Leu Tyr Lys His Ala Tyr Ser Val Glu Gln
        1145                1150                1155

Ile Tyr Lys Asp Ala Ala Ser Gly Ile Asn Phe Asn Trp Asn Trp
        1160                1165                1170

Leu Tyr Leu Val Phe Leu Ile Leu Phe Val Lys Pro Val Ala Gly
        1175                1180                1185

Phe Val Ile Ile Cys Tyr Cys Val Lys Tyr Leu Val Leu Ser Ser
        1190                1195                1200

Thr Val Leu Gln Thr Gly Val Gly Phe Leu Asp Trp Phe Val Lys
        1205                1210                1215

Thr Val Phe Thr His Phe Asn Phe Met Gly Ala Gly Phe Tyr Phe
        1220                1225                1230

Trp Leu Phe Tyr Lys Ile Tyr Val Gln Val His His Ile Leu Tyr
        1235                1240                1245

Cys Lys Asp Val Thr Cys Glu Val Cys Lys Arg Val Ala Arg Ser
        1250                1255                1260

Asn Arg Gln Glu Val Ser Val Val Gly Gly Arg Lys Gln Ile
        1265                1270                1275

Val His Val Tyr Thr Asn Ser Gly Tyr Asn Phe Cys Lys Arg His
        1280                1285                1290

Asn Trp Tyr Cys Arg Asn Cys Asp Asp Tyr Gly His Gln Asn Thr
        1295                1300                1305

Phe Met Ser Pro Glu Val Ala Gly Glu Leu Ser Glu Lys Leu Lys

-continued

```
              1310                1315                1320
Arg His Val Lys Pro Thr Ala Tyr Ala Tyr His Val Val Tyr Glu
    1325                1330                1335
Ala Cys Val Val Asp Asp Phe Val Asn Leu Lys Tyr Lys Ala Ala
    1340                1345                1350
Ile Pro Gly Lys Asp Asn Ala Ser Ser Ala Val Lys Cys Phe Ser
    1355                1360                1365
Val Thr Asp Phe Leu Lys Lys Ala Val Phe Leu Lys Glu Ala Leu
    1370                1375                1380
Lys Cys Glu Gln Ile Ser Asn Asp Gly Phe Ile Val Cys Asn Thr
    1385                1390                1395
Gln Ser Ala His Ala Leu Glu Glu Ala Lys Asn Ala Ala Val Tyr
    1400                1405                1410
Tyr Ala Gln Tyr Leu Cys Lys Pro Ile Leu Ile Leu Asp Gln Ala
    1415                1420                1425
Leu Tyr Glu Gln Leu Ile Val Glu Pro Val Ser Lys Ser Val Ile
    1430                1435                1440
Asp Lys Val Cys Ser Ile Leu Ser Asn Ile Ile Ser Val Asp Thr
    1445                1450                1455
Ala Ala Leu Asn Tyr Lys Ala Gly Thr Leu Arg Asp Ala Leu Leu
    1460                1465                1470
Ser Ile Thr Lys Asp Glu Glu Ala Val Asp Met Ala Ile Phe Cys
    1475                1480                1485
His Asn His Glu Val Glu Tyr Thr Gly Asp Gly Phe Thr Asn Val
    1490                1495                1500
Ile Pro Ser Tyr Gly Met Asp Thr Asp Lys Leu Thr Pro Arg Asp
    1505                1510                1515
Arg Gly Phe Leu Ile Asn Ala Asp Ala Ser Ile Ala Asn Leu Arg
    1520                1525                1530
Val Lys Asn Ala Pro Pro Val Val Trp Lys Phe Ser Asp Leu Ile
    1535                1540                1545
Lys Leu Ser Asp Ser Cys Leu Lys Tyr Leu Ile Ser Ala Thr Val
    1550                1555                1560
Lys Ser Gly Gly Arg Phe Phe Ile Thr Lys Ser Gly Ala Lys Gln
    1565                1570                1575
Val Ile Ser Cys His Thr Gln Lys Leu Leu Val Glu Lys Lys Ala
    1580                1585                1590
Gly
```